(12) United States Patent
Kurokawa et al.

(10) Patent No.: US 9,738,656 B2
(45) Date of Patent: Aug. 22, 2017

(54) PYRANODIPYRIDINE COMPOUND

(71) Applicant: Eisai R&D Management Co., Ltd., Bunkyo-ku, Tokyo (JP)

(72) Inventors: Toshiki Kurokawa, Tsukuba (JP); Yu Yoshida, Tsukuba (JP); Kogyoku Shin, Tokyo (JP); Yoshihisa Kobayashi, Tokyo (JP); Hironori Fukumoto, Tsukuba (JP); Kunitoshi Takeda, Tsukuba (JP); Yoshiaki Ohashi, Tsukuba (JP); Makoto Kotake, Tsukuba (JP); Tomoyuki Shibuguchi, Tsukuba (JP); Toru Watanabe, Tsukuba (JP); Yoichi Kita, Tsukuba (JP); Shinsuke Hirota, Tsukuba (JP); Takashi Fukuyama, Tsukuba (JP); Yasuaki Kamada, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/346,912

(22) Filed: Nov. 9, 2016

(65) Prior Publication Data

US 2017/0137436 A1 May 18, 2017

(30) Foreign Application Priority Data

Nov. 13, 2015 (JP) ................. 2015-222805

(51) Int. Cl.
*C07D 491/147* (2006.01)
*C07D 491/052* (2006.01)

(52) U.S. Cl.
CPC ..... *C07D 491/147* (2013.01); *C07D 491/052* (2013.01)

(58) Field of Classification Search
CPC .................................................. C07D 491/147
See application file for complete search history.

(56) References Cited

U.S. PATENT DOCUMENTS 6,949,571 B2    9/2005 Nagato et al.

FOREIGN PATENT DOCUMENTS

EP        1319659        6/2003
JP      S59-059665       4/1984
(Continued)

OTHER PUBLICATIONS

Search Report in International Patent Application No. PCT/JP2016/083211, dated Jan. 24, 2017, 10 pages.
(Continued)

*Primary Examiner* — Noble Jarrell
*Assistant Examiner* — John S Kenyon
(74) *Attorney, Agent, or Firm* — Fish & Richardson P.C.

(57) ABSTRACT

Compounds represented by formulae (I) to (XXII) or pharmaceutically acceptable salts thereof:

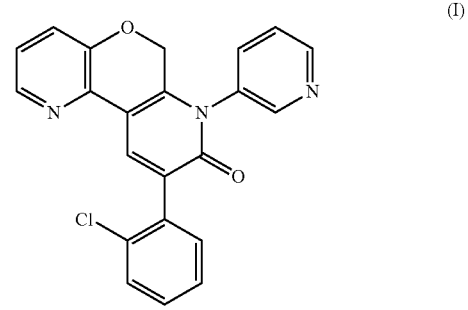

(I)

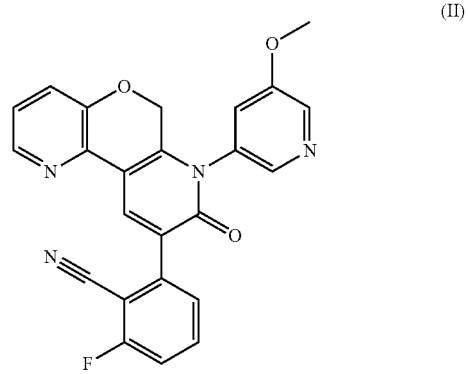

(II)

(III)

(IV)

(Continued)

(V)
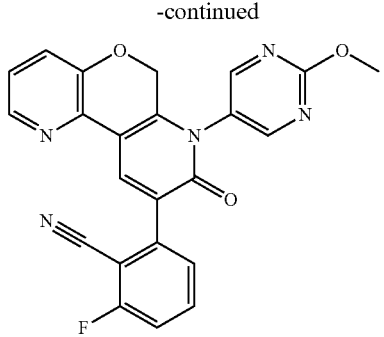
(X)
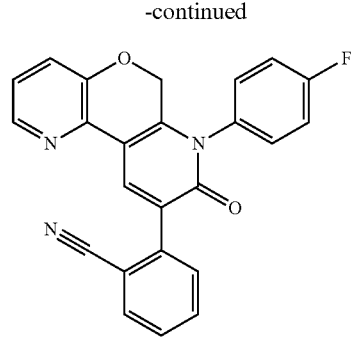
(VI)
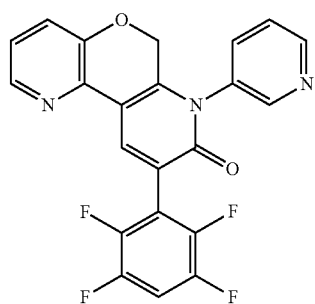
(XI)
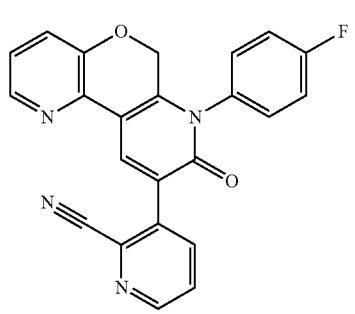
(VII)
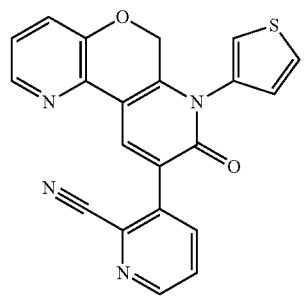
(XII)
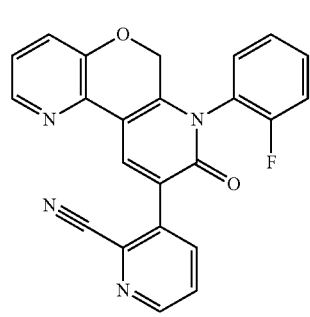
(VIII)
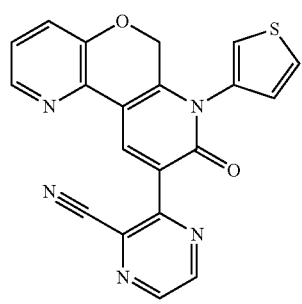
(XIII)
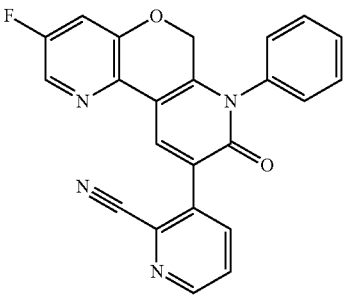
(IX)
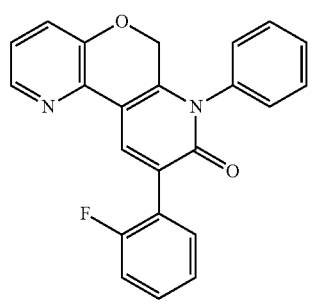
(XIV)
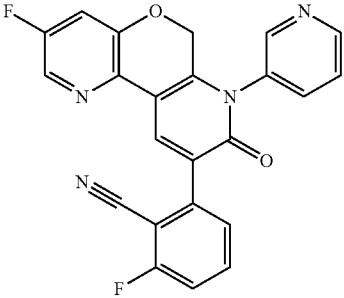

-continued (XV)
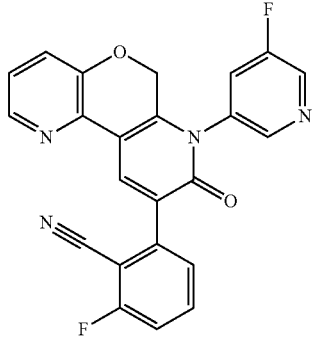

(XVI)
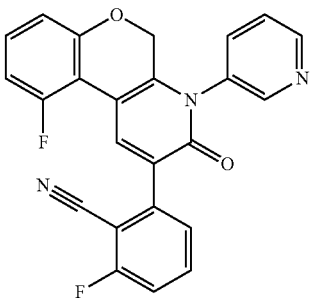

(XVII)
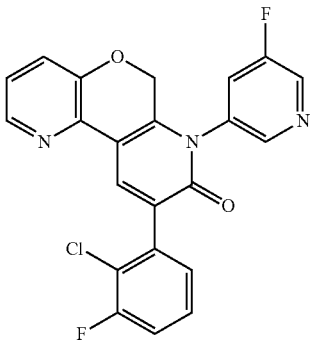

(XVIII)
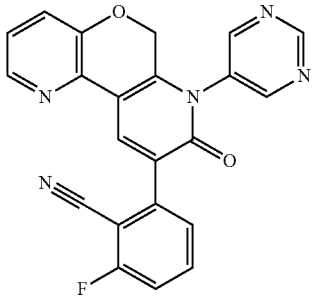

(XIX)
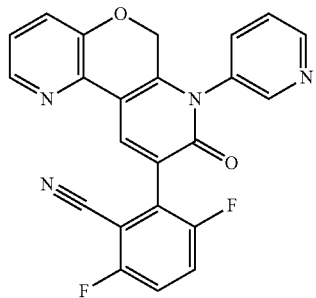

-continued (XX)
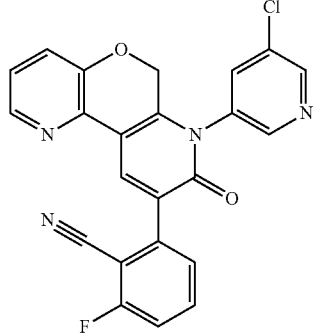

(XXI)
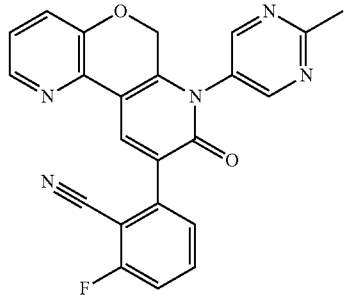

(XXII)
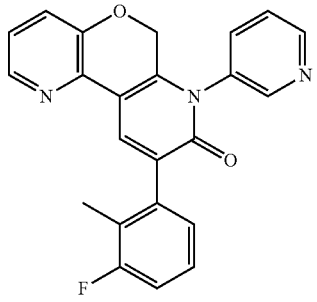

14 Claims, 2 Drawing Sheets

(56) References Cited

FOREIGN PATENT DOCUMENTS

| | | |
|---|---|---|
| JP | S62-142180 | 6/1987 |
| JP | H09-510730 | 10/1997 |
| WO | WO 02/22587 | 3/2002 |

OTHER PUBLICATIONS

Barton et al., "Pharmacological characterization of the 6 Hz psychomotor seizure model of partial epilepsy," Epilepsy Research 47:217-227 (2001).

Catarzi et al., "Competitive AMPA Receptor Antagonists," Medicinal Research Reviews, 27(2):239-278 (2007).

De Sarro et al., "AMPA Receptor Antagonists as Potential Anticonvulsant Drugs," Current Topics in Medicinal Chemistry, 5(1):31-42 (2005).

Fritsch et al., "Treatment of early and late kainic acid-induced status epilepticus with the noncompetitive AMPA receptor antagonist GYKI 52466," Epilepsia 51(1):108-117 (2010).

(56) References Cited

OTHER PUBLICATIONS

Hanada, "The discovery and development of perampanel for the treatment of epilepsy," Expert Opinion on Drug Discovery, 9(4):449-458 (Feb. 2014).
Hosford et al., "Increased AMPA-Sensitive Quisqualate Receptor Binding and Reduced NMDA Receptor Binding in Epileptic Human Hippocampus," The Journal of Neuroscience, 11:428-434 (1991).
Rogawski et al., "AMPA receptors as a molecular target in epilepsy therapy," Acta Neurol Scand., 127(Suppl. 197):p9-p18 (2013).
Russo et al., "New AMPA antagonists in epilepsy," Expert Opinion on Investigational Drugs, 21(9):1371-1389 (2012).
Tortorella et al., "A Crucial Role of the a-Amino-3-Hydroxy-5-methylisoxazole-4-Propionic Acid Subtype of Glutamate Receptors in Piriform and Perirhinal Cortex for the Initiation and Propagation of Limbic Motor Seizures," The Journal of Pharmacology and Experimental Therapeutics, 280(3):1401-1405 (1997).
Yamaguchi et al., "Anticonvulsant activity of AMPA/kainate antagonists: comparison of GYKI 52466 and NBQX in maximal electroshock and chemoconvulsant seizure models," Epilepsy Research, 15:179-184 (1993).
Hibi et al., "Discovery of 2-(2-Oxo-1-phenyl-5-pyridin-2-yl-1,2-dihydropyridin-3-yl)benzonitrile (Perampanel): A Novel, Noncompetitive α-Amino-3-hydroxy-5-methyl-4-isoxazolepropanoic Acid (AMPA) Receptor Antagonist" Journal of Medicinal Chemistry, 2012; 55:10584-10600.

PYRANODIPYRIDINE COMPOUND

TECHNICAL FIELD

The present invention relates to pyranodipyridine compounds having α-amino-3-hydroxy-5-methyl-4-isoxazolepropionic acid (AMPA) receptor inhibitory action and pharmaceutically acceptable salts thereof.

BACKGROUND

It is known that glutamic acid released from the presynaptic region plays an important role in excitatory signaling in the central nervous system. This action is brought about when glutamic acid binds to glutamate receptors present in the postsynaptic region, and the glutamate receptors are classified into ionotropic receptors and G-protein-coupled receptors, with the former being further classified into α-amino-3-hydroxy-5-methyl-4-isoxazolepropionic acid (AMPA) receptor, N-methyl-D-aspartic acid (NMDA) receptor, kainate receptor, and the like. Among the above, the AMPA receptor is a receptor that is widely expressed in the brain, and plays a key role in the regulation of fast excitatory synaptic transmission or synaptic plasticity.

Since the AMPA receptor thus plays a physiologically important role, its dysfunction is known to be involved in various diseases, for example, by causing abnormal excitability of neurons where the AMPA receptor is present. Examples of such diseases include epilepsy, various pains (peripheral nerve pain, central nerve pain, and nociceptive pain (each including chronic, acute, or intermittent pain)), various demyelinating diseases such as multiple sclerosis, various neurodegenerative diseases such as Parkinson's disease, Alzheimer's disease, amyotrophic lateral sclerosis (ALS), Huntington's chorea, and AIDS neuropathy, various psychiatric diseases such as anxiety, depression, bipolar mood disorder, dependency, drug abuse, and schizophrenia, motor dysfunction such as cerebral ischemia, head trauma, cerebrospinal injury, tremor, dystonia, and dyskinesia, and a developmental disorder such as autism. Inhibitors of the AMPA receptor (AMPA inhibitors) are therefore expected to lead to the treatment of these diseases, and are particularly known to be useful in treating epilepsy (Non Patent Literature 1).

Epilepsy is one of the most frequent central nerve diseases, and there are about 50 million or more epileptic patients worldwide. According to the World Health Organization, epilepsy is defined as "a chronic disorder of the brain caused by various causes; it is mainly characterized by recurrent seizures (epileptic seizures) derived from excessive electrical discharges in cerebral neurons, and the seizures involve manifestations of clinical and examination findings that vary greatly".

Examples of known epileptic seizures include partial seizures such as simple partial seizure, complex partial seizure, and secondary generalized seizure, absence seizure, myoclonic seizure, clonic seizure, tonic seizure, tonic-clonic seizure, atonic seizure, tuberous sclerosis complex, Dravet syndrome, progressive myoclonic epilepsy, Lafora disease, Unverricht-Lundborg disease, dentatorubral-pallidoluysian atrophy, fragile X syndrome, West syndrome, and Lennox-Gastaut syndrome. Epilepsy treatment is based on pharmacotherapy with anti-epileptic drugs. The goal of epilepsy treatment is to eliminate epileptic seizures, and avoid the development of side effects caused by the treatment. Treatment with anti-epileptic drugs begins with a single drug in principle. Generally, single-drug treatment is carried out by sequentially using two or three different drugs, and if this is not successful, multiple drug treatment is attempted. Amelioration of seizures through the treatment with anti-epileptic drugs can be expected in about 70% of patients with new onset of epilepsy. It is known, however, that in the remaining about 30% of patients, epileptic seizures are difficult to suppress even with drug treatment including multiple drug therapy.

An epileptic seizure is believed to be caused when abnormal excitability of some neurons develops into abnormal synchronization of firing in an entire population of neurons, and there have been many reports that glutamate neurons, in particular, the AMPA receptor, play a key role in the occurrence and propagation of an epileptic seizure. For example, it has been reported that AMPA inhibitors suppress the occurrence and propagation of convulsions in rat bicuculline-induced convulsion models (Non Patent Literatures 2 and 3); additionally, it is well known that AMPA inhibitors exhibit potent anticonvulsant action in a wide range of convulsion models (Non Patent Literatures 4 and 5). Further, it is known that AMPA inhibitors also have seizure-stopping action in status epilepticus models that experience extremely serious and continuous seizures, and thus, AMPA inhibitors are also expected to be applied to status epilepticus (Non Patent Literature 6).

It has been reported that similarly in humans, the expression of the AMPA receptor was increased in hippocampal neurons containing an epileptic focus, which were sampled from epileptic patients (Non Patent Literature 7). Further, because AMPA receptor inhibitors have been reported to have anticonvulsant action in humans, they are expected to have efficacy particularly as agents for treating epilepsy (Non Patent Literature 5).

As described above, AMPA inhibitors are expected to become therapeutic drugs for various central nerve diseases such as epilepsy; however, they are known to cause central nervous system depressant action such as sedation or loss of coordination, at a dose substantially equivalent to or lower than that showing main effect (Non Patent Literature 8). It has been reported that in humans, the central nervous system depressant action is reduced if the dose is gradually increased (Non Patent Literature 9); however, central nervous system depressant action is observed at a middle to high dose, which has become a problem that lowers the quality of life of epileptic patients in need of long-term administration, and also leads to the restriction of the dose.

The following compound is known as a compound having AMPA receptor inhibitory action (Patent Literature 1):

[Chemical Formula 1]

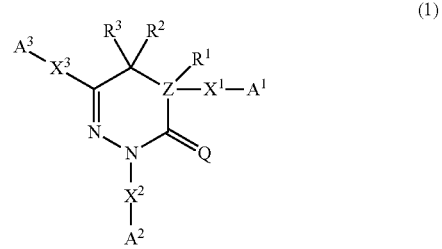

(1)

wherein $A^1$, $A^2$, and $A^3$ may each independently be a $C_{6-14}$ aromatic hydrocarbon cyclic group or 5- to 14-membered aromatic heterocyclic group; $X^1$, $X^2$, and $X^3$ may each independently be a single bond; Q may be an oxygen atom;

Z may be a carbon atom; $R^1$ and $R^2$ may be attached to each other such that $CR^2$—$ZR^1$ forms a carbon-carbon double bond represented by C=C; and $R^3$ may be attached to any atom on $A^3$, and together with the atom, may form an optionally substituted 5- to 8-membered heterocyclic ring.

In particular, Patent Literature 1 discloses as Example 9 a compound having a tricyclic skeleton represented by the formula:

[Chemical Formula 2]

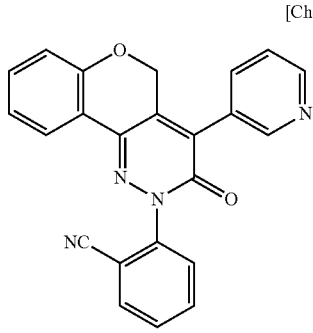

CITATION LIST

Patent Literature

[Patent Literature 1] WO02/22587

Non Patent Literature

[Non Patent Literature 1] Daniela Catarzi et al. *Medicinal Research Reviews*, vol. 27, No. 2, pp. 239-278, 2007
[Non Patent Literature 2] Rogawski M A et al. *Acta Neurol Scand Suppl.* 2013; (197): 9-18
[Non Patent Literature 3] Alfonso Tortorella et al. *JPET* 280: 1401-1405, 1997
[Non Patent Literature 4] De Sarro et al. *Curr Top Med Chem.* 2005; 5 (1): 31-42
[Non Patent Literature 5] Russo E et al. *Expert Opin Investig Drugs.* September 2012; 21(9): 1371-89.
[Non Patent Literature 6] Brita Fritsch et al. *Epilepsia*, 51 (1): 108-117, 2010
[Non Patent Literature 7] Hosford D A et al. *J Neurosci* 1991; 11: 428-434
[Non Patent Literature 8] Shun-ichi Yamaguchi et al. *Epilepsy Research*, 15 (1993) 179-184
[Non Patent Literature 9] Hanada T. *Expert Opin Drug Discov.* 2014 Feb. 24, 9(4): 449-458

SUMMARY

An object of the present invention is to provide a novel compound having potential use for treating epilepsy, which has AMPA receptor inhibitory action, and reduced central nervous system depressant action, or a pharmaceutically acceptable salt thereof.

The present inventors have continued vigorous research to achieve the above-described object, and consequently have found novel pyranodipyridine compounds having AMPA receptor inhibitory action and reduced central nervous system depressant action, or pharmaceutically acceptable salts thereof.

In summary, the present invention relates to <1> to <19> set forth below.

<1> A compound selected from the group consisting of:
9-(2-chlorophenyl)-7-(pyridin-3-yl)-6H-pyrano[3,2-b:5,4-b']dipyridin-8(7H)-one:

[Chemical Formula 3]

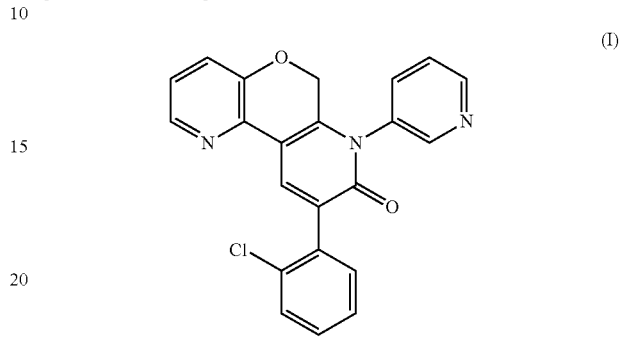

(I)

2-fluoro-6-(7-(5-methoxypyridin-3-yl)-8-oxo-7,8-dihydro-6H-pyrano[3,2-b:5,4-b']dipyridin-9-yl)benzonitrile:

[Chemical Formula 4]

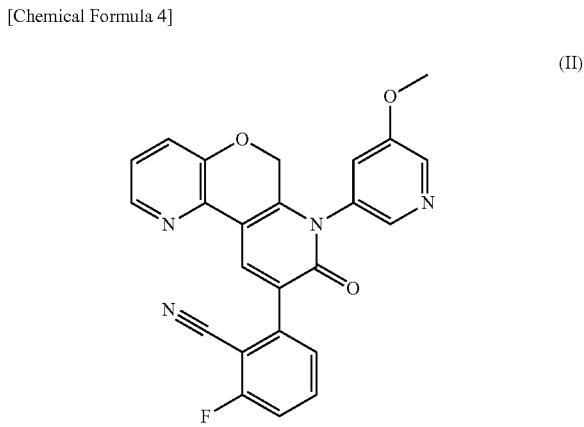

(II)

2-fluoro-6-(7-(6-methylpyridin-3-yl)-8-oxo-7,8-dihydro-6H-pyrano[3,2-b:5,4-b']dipyridin-9-yl)benzonitrile:

[Chemical Formula 5]

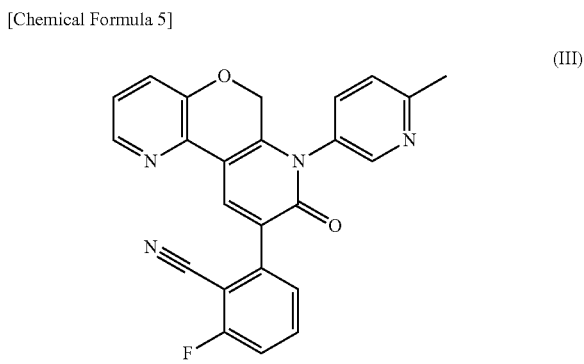 [SMILES: Cc1ccc(-n2c3c(cc(-c4cccc(F)c4Cl)c2=O)-c2ncccc2OC3)cn1]

(III)

9-(2-chloro-3-fluorophenyl)-7-(6-methylpyridin-3-yl)-6H-pyrano[3,2-b:5,4-b']dipyridin-8(7H)-one:

[Chemical Formula 6]

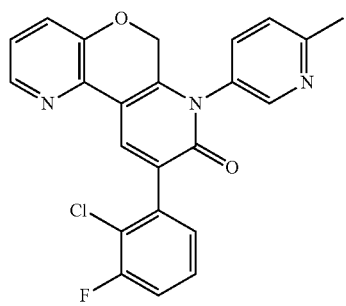

(IV)

2-fluoro-6-(7-(2-methoxypyrimidin-5-yl)-8-oxo-7,8-dihydro-6H-pyrano[3,2-b:5,4-b']dipyridin-9-yl)benzonitrile:

[Chemical Formula 7]

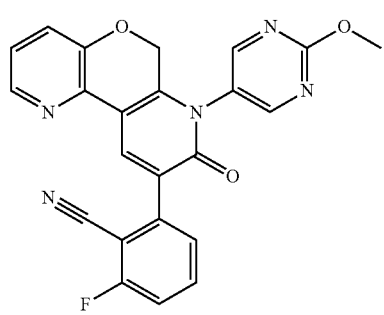

(V)

7-(pyridin-3-yl)-9-(2,3,5,6-tetrafluorophenyl)-6H-pyrano[3,2-b:5,4-b']dipyridin-8(7H)-one:

[Chemical Formula 8]

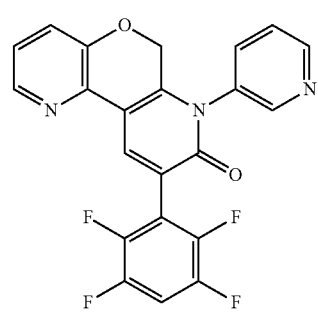

(VI)

3-(8-oxo-7-(thiophen-3-yl)-7,8-dihydro-6H-pyrano[3,2-b:5,4-b']dipyridin-9-yl)picolinonitrile:

[Chemical Formula 9]

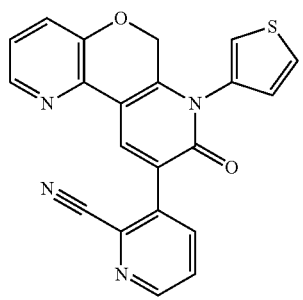

(VII)

3-(8-oxo-7-(thiophen-3-yl)-7,8-dihydro-6H-pyrano[3,2-b:5,4-b']dipyridin-9-yl)pyrazine-2-carbonitrile:

[Chemical Formula 10]

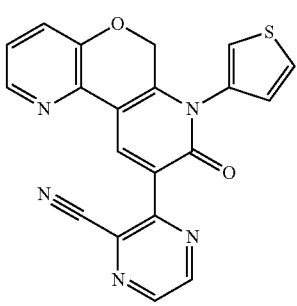

(VIII)

9-(2-fluorophenyl)-7-phenyl-6H-pyrano[3,2-b:5,4-b']dipyridin-8(7H)-one:

[Chemical Formula 11]

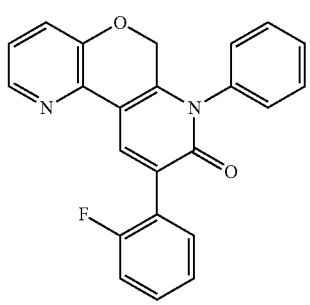

(IX)

2-(7-(4-fluorophenyl)-8-oxo-7,8-dihydro-6H-pyrano[3,2-b:5,4-b']dipyridin-9-yl)benzonitrile:

[Chemical Formula 12]

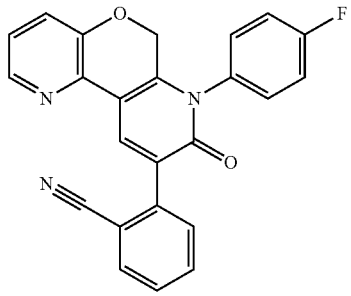

(X)

3-(7-(4-fluorophenyl)-8-oxo-7,8-dihydro-6H-pyrano[3,2-b:5,4-b']dipyridin-9-yl)picolinonitrile:

[Chemical Formula 13]

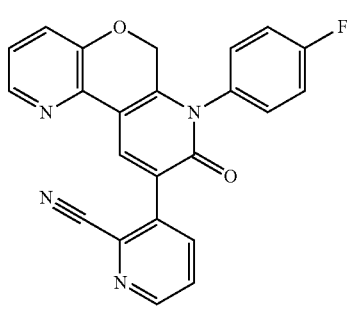

(XI)

3-(7-(2-fluorophenyl)-8-oxo-7,8-dihydro-6H-pyrano[3,2-b:5,4-b']dipyridin-9-yl)picolinonitrile:

[Chemical Formula 14]

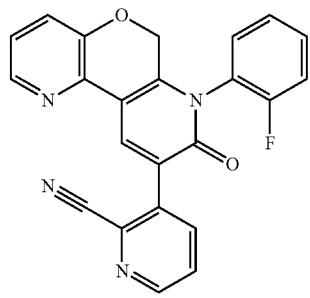

(XII)

3-(3-fluoro-8-oxo-7-phenyl-7,8-dihydro-6H-pyrano[3,2-b:5,4-b']dipyridin-9-yl)picolinonitrile:

[Chemical Formula 15]

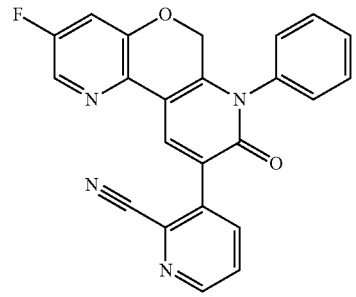

(XIII)

2-fluoro-6-(3-fluoro-8-oxo-7-(pyridin-3-yl)-7,8-dihydro-6H-pyrano[3,2-b:5,4-b']dipyridin-9-yl)benzonitrile:

[Chemical Formula 16]

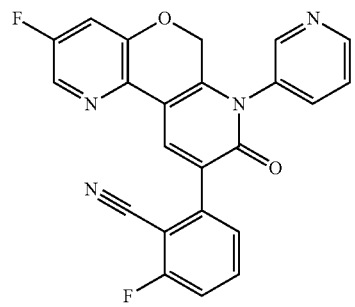

(XIV)

2-fluoro-6-(7-(5-fluoropyridin-3-yl)-8-oxo-7,8-dihydro-6H-pyrano[3,2-b:5,4-b']dipyridin-9-yl)benzonitrile:

[Chemical Formula 17]

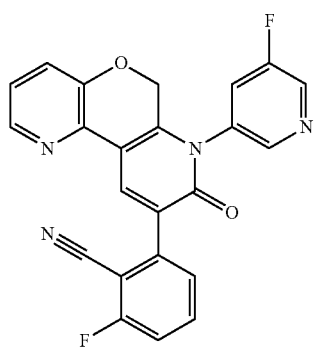

(XV)

2-fluoro-6-(10-fluoro-3-oxo-4-(pyridin-3-yl)-4,5-dihydro-3H-chromeno[3,4-b]pyridin-2-yl)benzonitrile:

[Chemical Formula 18]

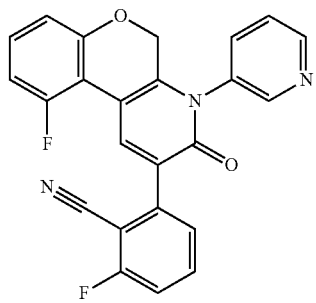

(XVI)

9-(2-chloro-3-fluorophenyl)-7-(5-fluoropyridin-3-yl)-6H-pyrano[3,2-b']dipyridin-8(7H)-one:

[Chemical Formula 19]

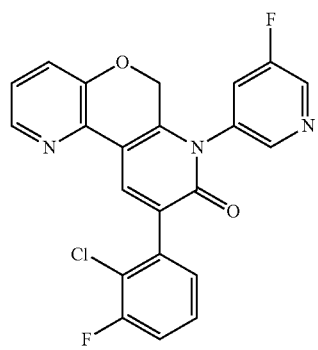

(XVII)

2-fluoro-6-(8-oxo-7-(pyrimidin-5-yl)-7,8-dihydro-6H-pyrano[3,2-b:5,4-b']dipyridin-9-yl)benzonitrile:

[Chemical Formula 20]

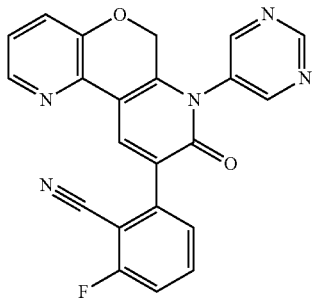

(XVIII)

3,6-difluoro-2-(8-oxo-7-(pyridin-3-yl)-7,8-dihydro-6H-pyrano[3,2-b:5,4-b']dipyridin-9-yl)benzonitrile:

[Chemical Formula 21]

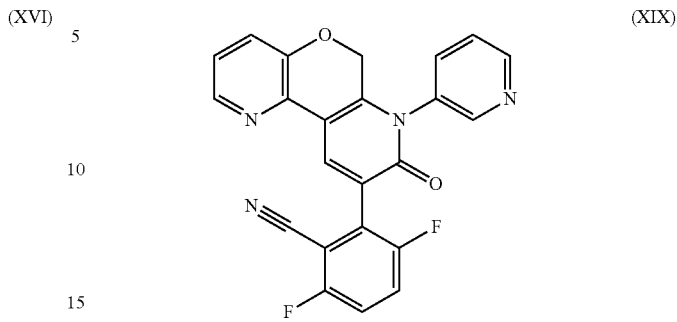

(XIX)

2-(7-(5-chloropyridin-3-yl)-8-oxo-7,8-dihydro-6H-pyrano[3,2-b:5,4-b']dipyridin-9-yl)-6-fluorobenzonitrile:

[Chemical Formula 22]

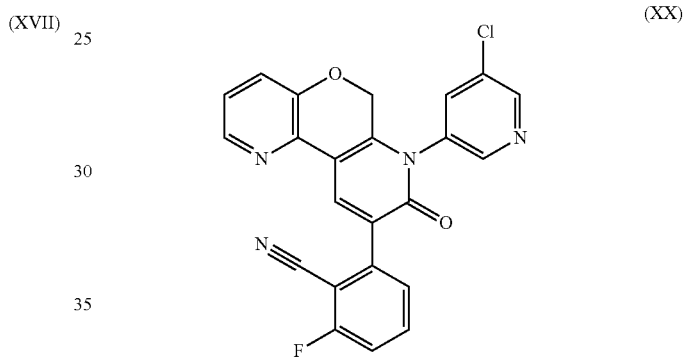

(XX)

2-fluoro-6-(7-(2-methylpyrimidin-5-yl)-8-oxo-7,8-dihydro-6H-pyrano[3,2-b:5,4-b']dipyridin-9-yl)benzonitrile:

[Chemical Formula 23]

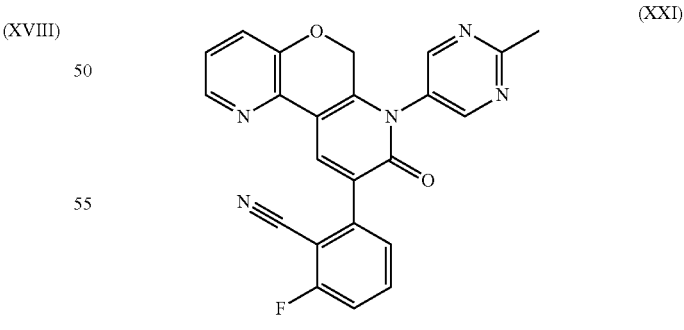

(XXI)

and 9-(3-fluoro-2-methylphenyl)-7-(pyridin-3-yl)-6H-pyrano[3,2-b:5,4-b']dipyridin-8(7H)-one:

[Chemical Formula 24]

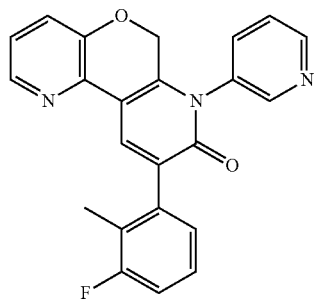
(XXII)

or a pharmaceutically acceptable salt thereof.

<2> A compound selected from the group consisting of:
9-(2-chlorophenyl)-7-(pyridin-3-yl)-6H-pyrano[3,2-b:5,4-b']dipyridin-8(7H)-one:

[Chemical Formula 25]

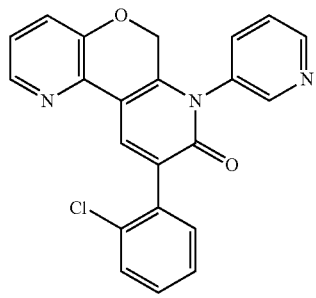
(I)

2-fluoro-6-(7-(5-methoxypyridin-3-yl)-8-oxo-7,8-dihydro-6H-pyrano[3,2-b:5,4-b']dipyridin-9-yl)benzonitrile:

[Chemical Formula 26]

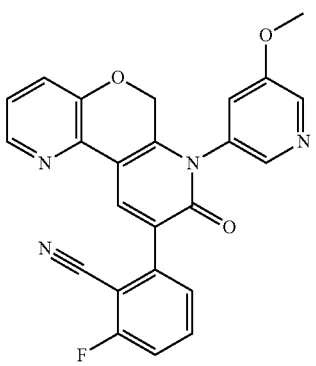
(II)

2-fluoro-6-(7-(6-methylpyridin-3-yl)-8-oxo-7,8-dihydro-6H-pyrano[3,2-b']dipyridin-9-yl)benzonitrile:

[Chemical Formula 27]

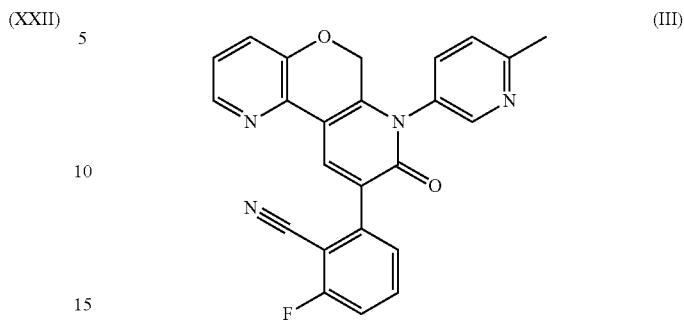
(III)

9-(2-chloro-3-fluorophenyl)-7-(6-methylpyridin-3-yl)-6H-pyrano[3,2-b:5,4-b']dipyridin-8(7H)-one:

[Chemical Formula 28]

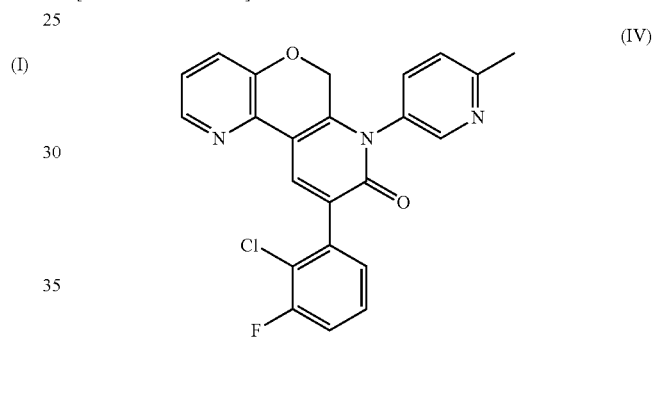
(IV)

2-fluoro-6-(7-(2-methoxypyrimidin-5-yl)-8-oxo-7,8-dihydro-6H-pyrano[3,2-b']dipyridin-9-yl)benzonitrile:

[Chemical Formula 29]

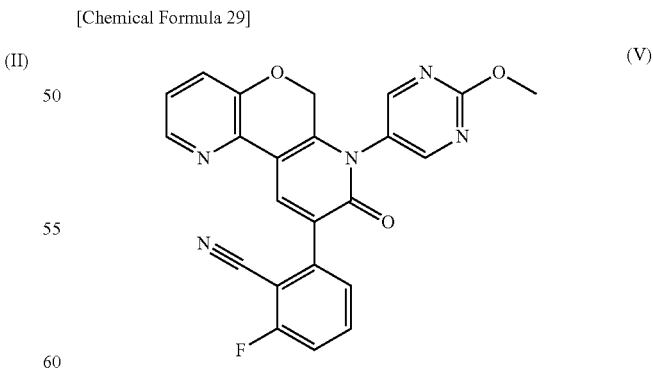
(V)

7-(pyridin-3-yl)-9-(2,3,5,6-tetrafluorophenyl)-6H-pyrano[3,2-b:5,4-b']dipyridin-8(7H)-one:

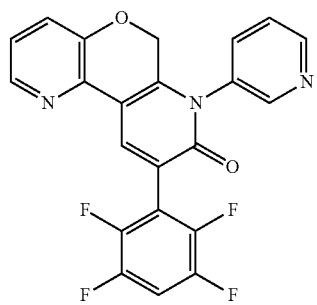

(VI)

3-(8-oxo-7-(thiophen-3-yl)-7,8-dihydro-6H-pyrano[3,2-b:5,4-b']dipyridin-9-yl)picolinonitrile:

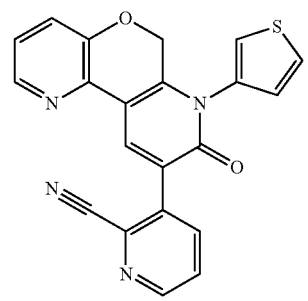

(VII)

3-(8-oxo-7-(thiophen-3-yl)-7,8-dihydro-6H-pyrano[3,2-b:5,4-b']dipyridin-9-yl)pyrazine-2-carbonitrile:

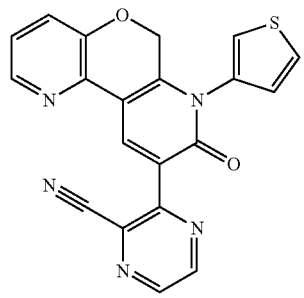

(VIII)

9-(2-fluorophenyl)-7-phenyl-6H-pyrano[3,2-b:5,4-b']dipyridin-8(7H)-one:

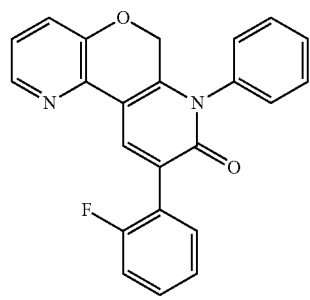

(IX)

2-(7-(4-fluorophenyl)-8-oxo-7,8-dihydro-6H-pyrano[3,2-b:5,4-b']dipyridin-9-yl)benzonitrile:

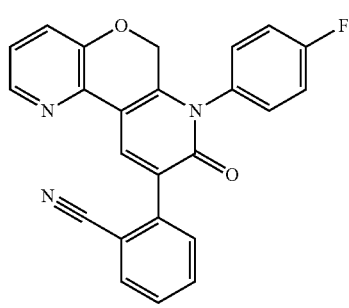

(X)

3-(7-(4-fluorophenyl)-8-oxo-7,8-dihydro-6H-pyrano[3,2-b:5,4-b']dipyridin-9-yl)picolinonitrile:

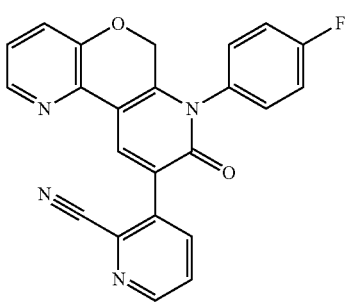

(XI)

3-(7-(2-fluorophenyl)-8-oxo-7,8-dihydro-6H-pyrano[3,2-b:5,4-b']dipyridin-9-yl)picolinonitrile:

[Chemical Formula 36]

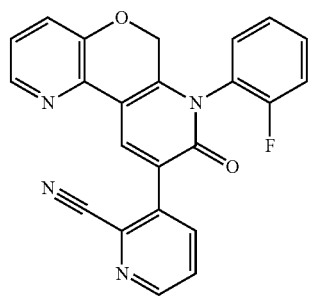
(XII)

3-(3-fluoro-8-oxo-7-phenyl-7,8-dihydro-6H-pyrano[3,2-b:5,4-b']dipyridin-9-yl)picolinonitrile:

[Chemical Formula 37]

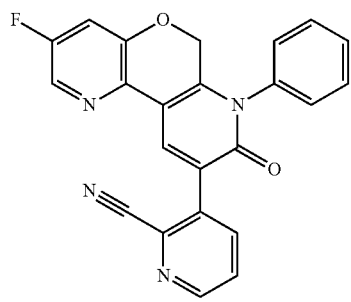
(XIII)

2-fluoro-6-(3-fluoro-8-oxo-7-(pyridin-3-yl)-7,8-dihydro-6H-pyrano[3,2-b:5,4-b']dipyridin-9-yl)benzonitrile:

[Chemical Formula 38]

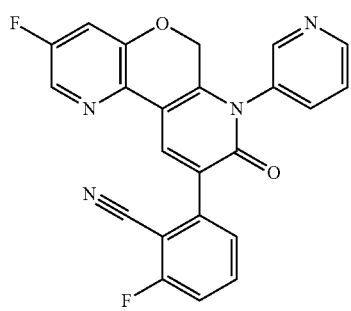
(XIV)

2-fluoro-6-(7-(5-fluoropyridin-3-yl)-8-oxo-7,8-dihydro-6H-pyrano[3,2-b:5,4-b']dipyridin-9-yl)benzonitrile:

[Chemical Formula 39]

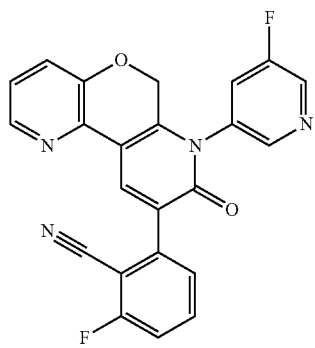
(XV)

2-fluoro-6-(10-fluoro-3-oxo-4-(pyridin-3-yl)-4,5-dihydro-3H-chromeno[3,4-b]pyridin-2-yl)benzonitrile:

[Chemical Formula 40]

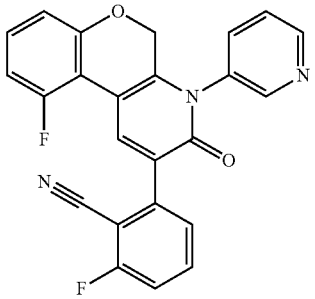
(XVI)

9-(2-chloro-3-fluorophenyl)-7-(5-fluoropyridin-3-yl)-6H-pyrano[3,2-b:5,4-b']dipyridin-8(7H)-one:

[Chemical Formula 41]

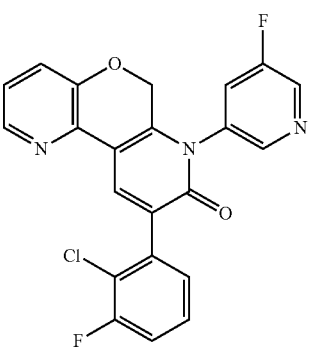
(XVII)

2-fluoro-6-(8-oxo-7-(pyrimidin-5-yl)-7,8-dihydro-6H-pyrano[3,2-b:5,4-b']dipyridin-9-yl)benzonitrile:

[Chemical Formula 42]

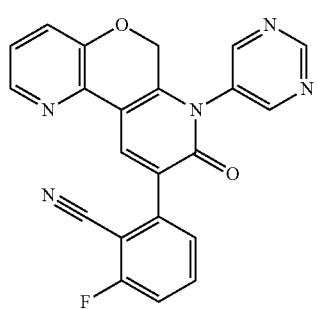

(XVIII)

3,6-difluoro-2-(8-oxo-7-(pyridin-3-yl)-7,8-dihydro-6H-pyrano[3,2-b:5,4-b']dipyridin-9-yl)benzonitrile:

[Chemical Formula 43]

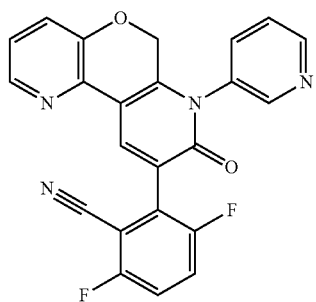

(XIX)

2-(7-(5-chloropyridin-3-yl)-8-oxo-7,8-dihydro-6H-pyrano[3,2-b:5,4-b']dipyridin-9-yl)-6-fluorobenzonitrile:

[Chemical Formula 44]

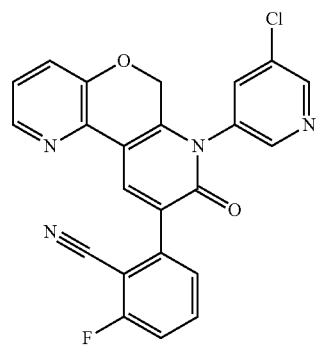

(XX)

and
2-fluoro-6-(7-(2-methylpyrimidin-5-yl)-8-oxo-7,8-dihydro-6H-pyrano[3,2-b:5,4-b']dipyridin-9-yl)benzonitrile:

[Chemical Formula 45]

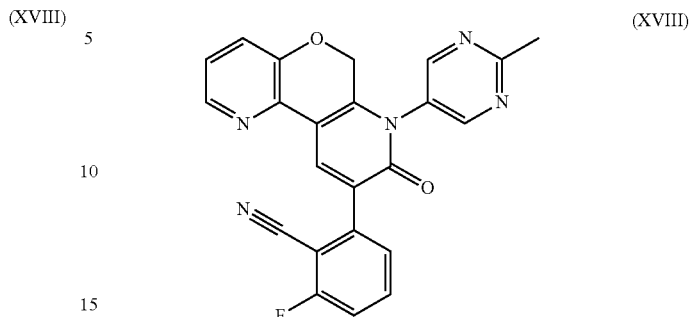

(XVIII)

or a pharmaceutically acceptable salt thereof.

<3> 9-(2-Chlorophenyl)-7-(pyridin-3-yl)-6H-pyrano[3,2-b:5,4-b']dipyridin-8(7H)-one:

[Chemical Formula 46]

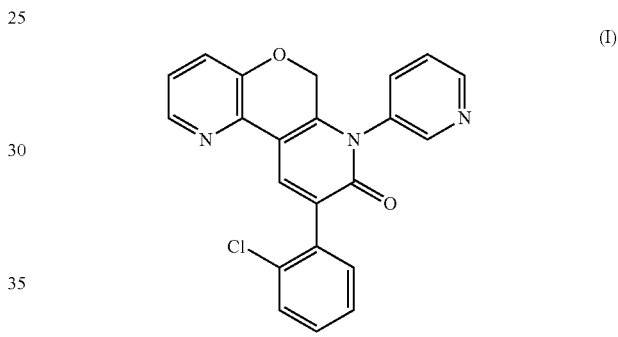

(I)

or a pharmaceutically acceptable salt thereof.

<4> 2-Fluoro-6-(7-(6-methylpyridin-3-yl)-8-oxo-7,8-dihydro-6H-pyrano[3,2-b:5,4-b']dipyridin-9-yl)benzonitrile:

[Chemical Formula 47]

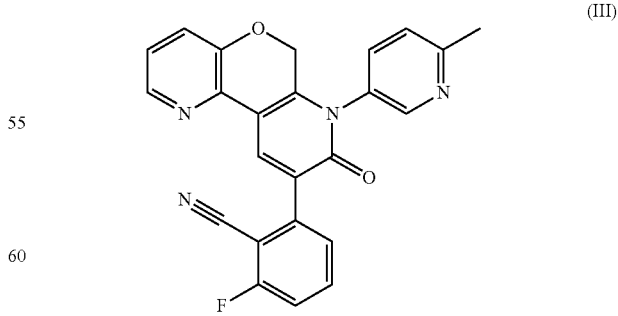

(III)

or a pharmaceutically acceptable salt thereof.

<5> 9-(2-Chloro-3-fluorophenyl)-7-(6-methylpyridin-3-yl)-6H-pyrano[3,2-b:5,4-b']dipyridin-8(7H)-one:

[Chemical Formula 48]

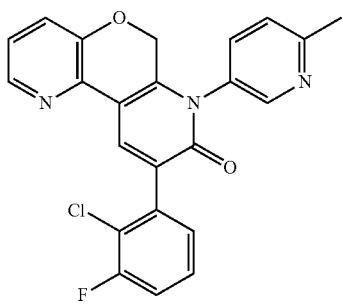

(IV)

or a pharmaceutically acceptable salt thereof.

<6> 2-Fluoro-6-(7-(2-methoxypyrimidin-5-yl)-8-oxo-7,8-dihydro-6H-pyrano[3,2-b:5,4-b']dipyridin-9-yl)benzonitrile:

[Chemical Formula 49]

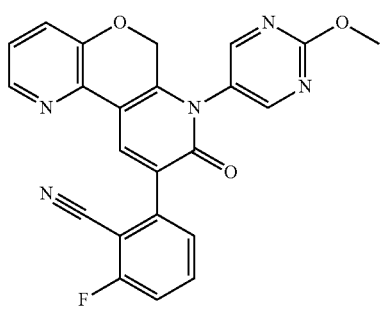

(V)

or a pharmaceutically acceptable salt thereof.

<7> 3-(7-(4-Fluorophenyl)-8-oxo-7,8-dihydro-6H-pyrano[3,2-b:5,4-b']dipyridin-9-yl)picolinonitrile:

[Chemical Formula 50]

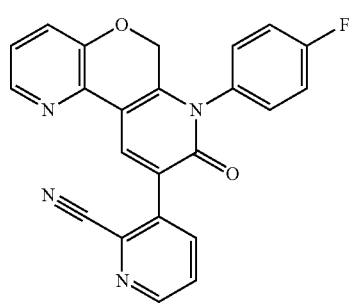

(XI)

or a pharmaceutically acceptable salt thereof.

<8> 3-(3-Fluoro-8-oxo-7-phenyl-7,8-dihydro-6H-pyrano[3,2-b:5,4-b']dipyridin-9-yl)picolinonitrile:

[Chemical Formula 51]

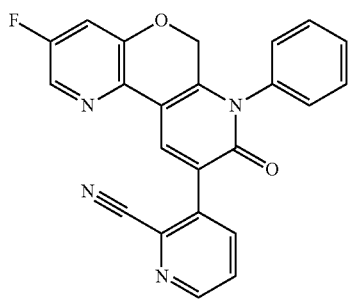

(XIII)

or a pharmaceutically acceptable salt thereof.

<9> 2-Fluoro-6-(3-fluoro-8-oxo-7-(pyridin-3-yl)-7,8-dihydro-6H-pyrano[3,2-b:5,4-b']dipyridin-9-yl)benzonitrile:

[Chemical Formula 52]

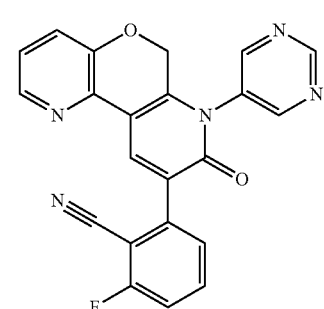

(XIV)

or a pharmaceutically acceptable salt thereof.

<10> 2-Fluoro-6-(8-oxo-7-(pyrimidin-5-yl)-7,8-dihydro-6H-pyrano[3,2-b:5,4-b']dipyridin-9-yl)benzonitrile:

[Chemical Formula 53]

(XVIII)

or a pharmaceutically acceptable salt thereof.

<11> 3,6-Difluoro-2-(8-oxo-7-(pyridin-3-yl)-7,8-dihydro-6H-pyrano[3,2-b:5,4-b']dipyridin-9-yl)benzonitrile:

[Chemical Formula 54]

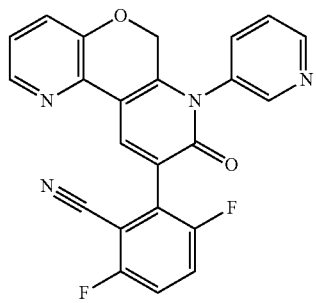

(XIX)

or a pharmaceutically acceptable salt thereof.

<12> 2-Fluoro-6-(7-(2-methylpyrimidin-5-yl)-8-oxo-7,8-dihydro-6H-pyrano[3,2-b:5,4-b']dipyridin-9-yl)benzonitrile:

[Chemical Formula 55]

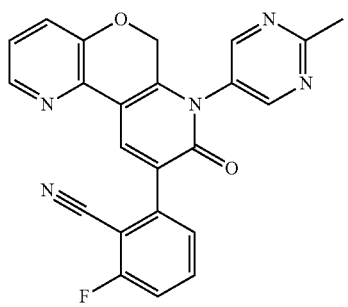

(XXI)

or a pharmaceutically acceptable salt thereof.

<13> A pharmaceutical composition comprising, as an active ingredient, the compound according to any one of <1> to <12> or a pharmaceutically acceptable salt thereof.

<14> The pharmaceutical composition according to <13>, which is an AMPA receptor inhibitor.

<15> The pharmaceutical composition according to <13> for treating epilepsy.

<16> The pharmaceutical composition according to <15> wherein epilepsy is partial epilepsy.

<17> An agent for treating epilepsy, comprising the compound according to any one of <1> to <12> or a pharmaceutically acceptable salt thereof.

<18> The agent according to <17> wherein epilepsy is partial epilepsy.

<19> A method for treating epilepsy, comprising administering to a patient the compound according to any one of <1> to <12> or a pharmaceutically acceptable salt thereof.

<20> The method according to <19> wherein epilepsy is partial epilepsy,

<21> The compound according to any one of <1> to <12> or a pharmaceutically acceptable salt thereof, used for treating epilepsy.

<22> The compound according to <21> wherein epilepsy is partial epilepsy.

<23> Use of the compound according to any one of <1> to <12> or a pharmaceutically acceptable salt thereof for producing an agent for treating epilepsy.

<24> Use of the compound according to <23> wherein epilepsy is partial epilepsy.

The pyranodipyridine compounds represented by formulae (I) to (XXII) according to the present invention (hereinafter referred to as compounds (I) to (XXII)) or pharmaceutically acceptable salts thereof have AMPA receptor inhibitory action, as shown in activity data in the Pharmacological Test Example described below, and convulsion-suppressing action and central nervous system depressant action are separated from each other. The compounds (I) to (XXII) of the present invention have AMPA receptor inhibitory action, and hence, can be expected to suppress abnormal excitability caused by glutamic acid in the brain, which leads to suppression of epileptic seizures, and moreover, the compounds (I) to (XXII) of the present invention have safety margins with respect to the central nervous system depressant action, and hence, have applicability as agents for treating epilepsy.

DETAILED DESCRIPTION

Figure 1:
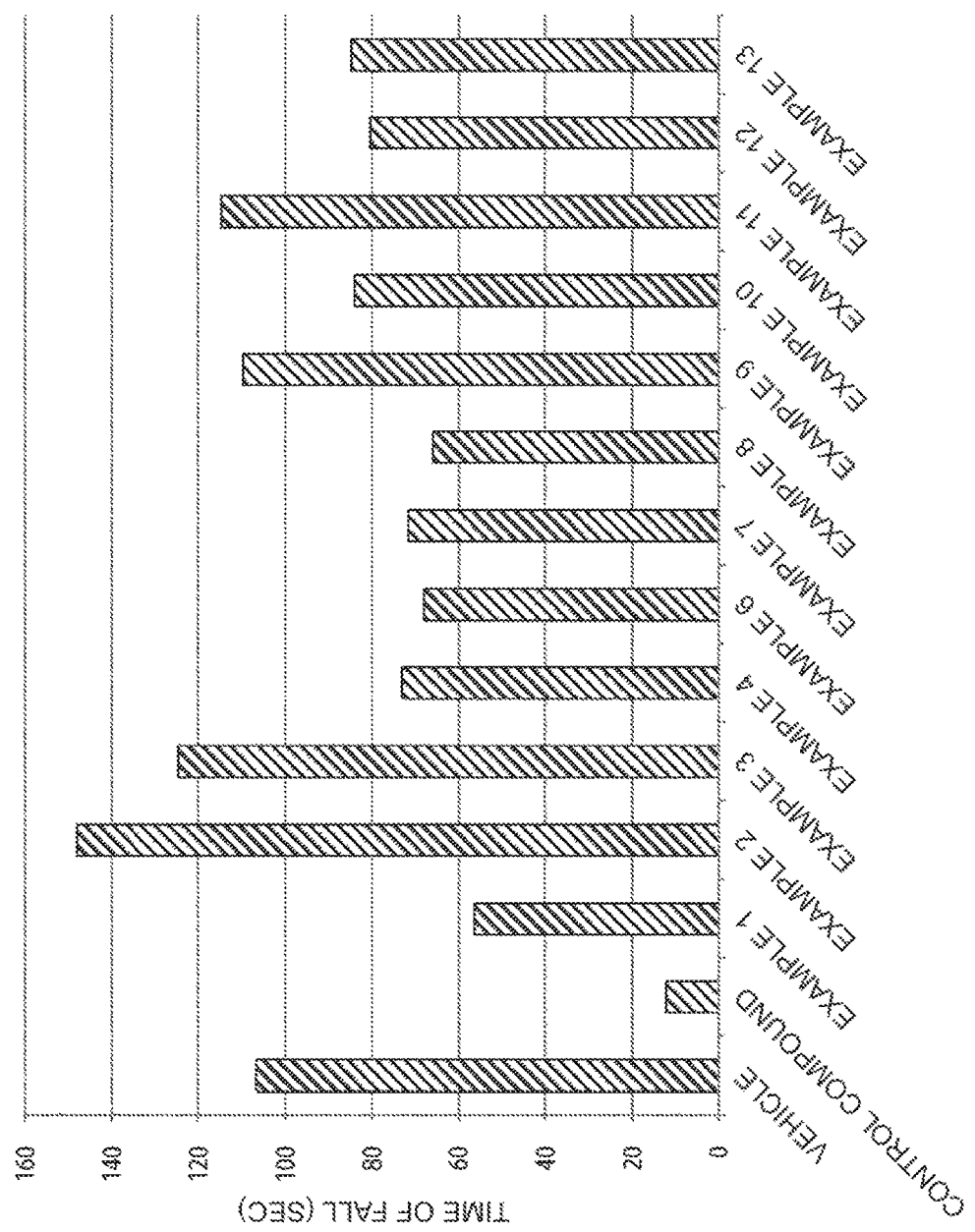
FIG. 1 is a diagram showing the results of rotarod performance tests on compounds of Examples 1 to 4 and 6 to 13 and a control compound.

The present invention will be hereinafter described in detail.

In the compounds of the present specification, the structural formula may represent a certain isomer for convenience sake; however, the compound is not limited to the formula shown for convenience sake, and includes all the structurally possible isomers and isomeric mixtures of the compound, such as geometrical isomers, optical isomers, rotamers, stereoisomers and tautomers, and may be either one of the isomers, or a mixture containing each of the isomers at a given ratio. Thus, optical isomers and a racemate, for example, may be present for the compound in the present specification; however, it is not limited to any of them in the present specification, and the compound in the present specification may be a racemate, any of the optically active substances, or a mixture containing each of the optically active substances at a given ratio.

Further, crystalline polymorphs may also be present, although the present invention is similarly not limited to any of them, and the compound of the present invention may be in a single form of any of the crystal forms, or a mixture thereof, and the present invention also includes amorphous forms. The compound of the present invention also encompasses anhydrides and solvates (in particular, a hydrate).

The present invention also includes compounds obtained by isotopic labeling of compounds (I) to (XXII). Such isotopically labeled compounds are identical to the compounds (I) to (XXII) except that one or more atoms have been replaced with atoms having an atomic mass or mass number different from those generally found in nature. Examples of isotopes that can be incorporated into the compounds of the present invention include isotopes of hydrogen, carbon, nitrogen, oxygen, fluorine, phosphorus, sulfur, iodine, and chlorine, such as $^2H$, $^3H$, $^{11}C$, $^{14}C$, $^{15}N$, $^{18}O$, $^{18}F$, and $^{35}S$.

The above-described isotopically labeled compounds, for example, compounds into which radioactive isotopes such as $^3H$ and/or $^{14}C$ have been incorporated, are useful in a topographic assay of pharmaceuticals and/or substrates. $^3H$ and $^{14}C$ are considered to be useful because they are readily prepared and detected. Isotopes $^{11}C$ and $^{18}F$ are considered to be useful for PET (positron emission tomography), and all of these isotopes are useful for brain imaging. Substitution with a heavier isotope such as $^2H$ provides certain therapeutic benefits such as an increase in the in vivo half-life or a reduction in the required dose because of its higher metabolic stability, and hence, is considered to be useful under certain circumstances. The above-described isotopically labeled compounds can be uniformly prepared by performing the procedures disclosed in the Examples below, using readily available isotopically labeled reagents instead of reagents that are not isotopically labeled.

As used herein, the "pharmaceutically acceptable salt" is not particularly limited as long as it is a salt formed with any of the compounds of the present invention, and may specifically be, for example, an acid addition salt such as an inorganic acid salt, an organic acid salt, or an acidic amino acid salt.

With regard to the "pharmaceutically acceptable salt" herein, unless otherwise indicated, the number of molecules of the acid relative to one molecule of the compound in the formed salt is not particularly limited as long as a salt with an appropriate ratio is formed; however, the number of molecules of the acid relative to one molecule of the compound is preferably about 0.1 to about 5, more preferably about 0.5 to about 2, and still more preferably about 0.5, about 1, or about 2.

Preferable examples of inorganic acid salts include hydrochloride, hydrobromide, sulfate, nitrate, and phosphate, and preferable examples of organic acid salts include acetate, succinate, fumarate, maleate, tartrate, citrate, lactate, stearate, benzoate, methanesulfonate, p-toluenesulfonate, and benzenesulfonate.

Preferable examples of acidic amino acid salts include aspartate and glutamate.

When the compounds (I) to (XXII) according to the present invention are obtained in the free form, they can be converted to salts that may be formed by the compounds (I) to (XXII) described above or hydrates thereof, in accordance with a conventional method.

When the compounds (I) to (XXII) according to the present invention are obtained as salts or hydrates of the compounds (I) to (XXII), they can be converted to the free form of the compounds (I) to (XXII) described above, in accordance with a conventional method.

Moreover, various isomers obtained for the compounds in the present specification (for example, geometrical isomers, optical isomers, rotamers, stereoisomers, and tautomers) can be purified and isolated using common separation means, for example, recrystallization, a diastereomeric salt formation method, an enzymatic resolution method, and various types of chromatography (for example, thin layer chromatography, column chromatography, and gas chromatography).

[Preparation]

A pharmaceutical composition of the invention could be prepared by mixing pharmaceutically acceptable additives with a compound selected from the group of compounds (I) to (XXII) or a pharmaceutically acceptable salt thereof. A pharmaceutical composition of the invention could be prepared according to the known method such as a method described in the General Rules for Preparations of the Japanese Pharmacopoeia 16th Edition.

A pharmaceutical composition of the invention could be administered to patients appropriately depending on the dosage form.

The dose of each of the compounds (I) to (XXII) according to the present invention or a pharmaceutically acceptable salt thereof will vary depending on the severity of the condition, age, sex, body weight, type of the dosage form or salt, specific type of the disease, and the like; generally, however, for an adult, in the case of oral administration, the daily dose is about 30 µg to 10 g, preferably 100 µg to 5 g, and more preferably 100 µg to 1 g, and in the case of administration by injection, the daily dose is about 30 µg to 1 g, preferably 100 µg to 500 mg, and more preferably 100 µg to 300 mg, each administered in single or several divided doses.

The compounds of the present invention can be used as chemical probes for capturing target proteins of bioactive low-molecular-weight compounds. Specifically, the compounds of the present invention can be converted to affinity chromatography probes, photoaffinity probes, or the like, by introducing labeling groups, linkers, or the like into portions of the compounds different from their structural portions essential for the expression of activities, using a technique described in *J. Mass Spectrum. Soc. Jpn.* Vol. 51, No. 5 2003, p 492-498 or WO 2007/139149, for example.

Examples of labeling groups, linkers, and the like used for chemical probes include groups shown in the group consisting of (1) to (5) below:

(1) protein labeling groups such as photoaffinity labeling groups (for example, a benzoyl group, a benzophenone group, an azido group, a carbonylazido group, a diaziridine group, an enone group, a diazo group, and a nitro group) and chemical affinity groups (for example, a ketone group in which the alpha-carbon atom has been substituted with a halogen atom, a carbamoyl group, an ester group, an alkylthio group, an α,β-unsaturated ketone, an ester, or other Michael receptors, and an oxirane group);

(2) cleavable linkers such as —S—S—, —O—Si—O—, monosaccharides (such as a glucose group and a galactose group) or disaccharides (such as lactose), and oligopeptide linkers cleavable by enzymatic reactions;

(3) fishing tag groups such as biotin and a 3-(4,4-difluoro-5,7-dimethyl-4H-3a,4a-diaza-4-bora-s-indacen-3-yl)propionyl group;

(4) detectable markers, for example, radiolabeling groups such as $^{125}I$, $^{32}P$, $^3H$ and $^{14}C$; fluorescent labeling groups such as fluorescein, rhodmine, dansyl, umbelliferone, 7-nitrofurazanyl, and a 3-(4,4-difluoro-5,7-dimethyl-4H-3a,4a-diaza-4-bora-s-indacen-3-yl)propionyl group; chemiluminescent groups such as luciferin and luminol; and heavy metal ions such as lanthanoid metal ions and radium ions; or (5) groups bound to solid phase carriers such as glass beads, glass beds, microtiter plates, agarose beads, agarose beds, polystyrene beads, polystyrene beds, nylon beads, and nylon beds.

Probes prepared by introducing labeling groups or the like selected from the group consisting of (1) to (5) above into the compounds of the present invention in accordance with a method described in the above-mentioned documents or the like can be used as chemical probes for identification of labeled proteins useful for searching for novel drug targets, etc.

EXAMPLES

The compounds (I) to (XXII) of the present invention can be produced, for example, using the methods described in the following Examples, and the effects of the compounds can be confirmed using the methods described in the following Test Example. It should be noted, however, that these examples are illustrative, and the present invention is in any case not limited to the following specific examples, and modifications may be made thereto without departing from the scope of the present invention.

Compounds for which document names or the like are noted were produced in accordance with the document or the like.

The abbreviations used herein are conventional abbreviations well known to those skilled in the art. The following abbreviations will be used herein:

AIBN: 2,2'-azobis(isobutyronitrile)
(Ataphos)$_2$PdCl$_2$: bis(di-t-butyl(4-dimethylaminophenyl)phosphine)dichloropalladium(II)
DCM: dichloromethane
DIAD: diisopropyl azodicarboxylate
diglyme: 1-methoxy-2-(2-methoxyethoxy)ethane
DME: 1,2-dimethoxyethane
DMEAD: di-2-methoxyethyl azodicarboxylate
DMF: N,N-dimethylformamide
DMSO: dimethylsulfoxide
EDC: 1-ethyl-3-(3-dimethylaminopropyl)carbodiimide hydrochloride
IPA: isopropyl alcohol
mCPBA: 3-chloroperbenzoic acid
MTBE: 2-methoxy-2-methylpropane
n-: normal
NBS: N-bromosuccinimide
NMP: N-methyl-2-pyrrolidinone
Pd(PPh$_3$)$_4$: tetrakis(triphenylphosphine) palladium(0)
Pd(dppf)Cl$_2$: (1,1'-bis(diphenylphosphino)ferrocene)dichloropalladium(II)
t-: tertiary
TBAF: tetrabutylammonium fluoride
TFA: trifluoroacetic acid
THF: tetrahydrofuran
$^1$H-NMR: proton nuclear magnetic resonance spectrometry
MS: mass spectrometry In the following examples, referential examples, and production examples, the "room temperature" generally refers to about 10° C. to about 35° C. "%" refers to percent by weight, unless otherwise specified.

Chemical shifts in proton nuclear magnetic resonance spectra are recorded in δ units (ppm) relative to tetramethylsilane, and coupling constants are recorded in hertz (Hz). Abbreviations for splitting patterns are as follows:

s: singlet, d: doublet, t: triplet, q: quartet, m: multiplet, br.s: broad singlet.

For reactions using a microwave reactor in the production examples, referential examples, and examples, Initiator™ or Initiator+™ from Biotage Corporation was used.

For chromatography, as the silica gel, Silica Gel60 (70-230 mesh ASTM) from Merck Corporation or PSQ60B from Fuji Silysia Chemical Ltd. was used, or a pre-packed column {column: Hi-Flash™ Column (Silicagel) from Yamazen Corporation, size: any of S (16×60 mm), M (20×75 mm), L (26×100 mm), 2 L (26×150 mm), and 3 L (46×130 mm); or Biotage™ SNAP Ultra Silica Cartridge from Biotage Corporation, size: any of 10 g, 25 g, and 50 g} was used.

As the NH silica gel, CHROMATOREX NH-DM2035 from Fuji Silysia Chemical Ltd. was used, or a pre-packed column (column: Hi-Flash™ Column (Amino) from Yamazen Corporation, size: any of S (16×60 mm), M (20×75 mm), L (26×100 mm), 2 L (26×150 mm), and 3 L (46×130 mm); or Presep™ (Luer Lock) NH2 (HC) from Wako Pure Chemical Industries, Ltd., size: any of type M (14 g/25 mL), type L (34 g/70 mL), type 2L (50 g/100 mL), and type 3L (110 g/200 mL)} was used.

As neutral alumina, Aluminium oxide 90 active neutral, 70-230 mesh, Merck, E6NXX was used.

As the names of the compounds shown below, those displayed on the "E-Notebook" Version 12 (PerkinElmer Co., Ltd.) were used, except for commonly used reagents.

Production Example 1

Synthesis of 6H-pyrano[3,2-b:5,4-b']dipyridin-8(7H)-one

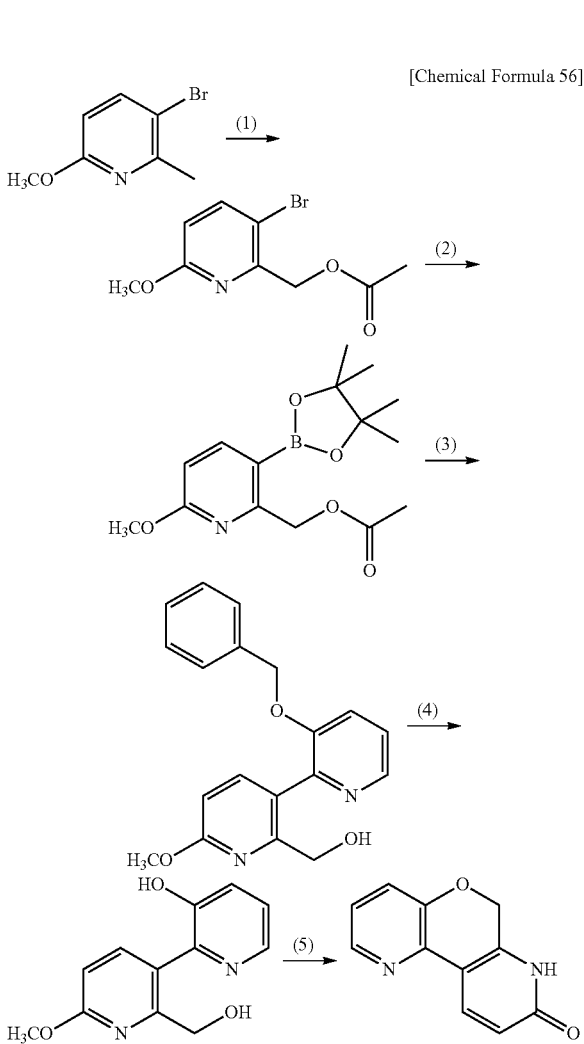

[Chemical Formula 56]

(1) Synthesis of (3-bromo-6-methoxypyridin-2-yl)methyl acetate

3-Bromo-6-methoxy-2-methylpyridine (CAS No. 126717-59-7) (4.87 kg, 24.1 mol, 1 equivalent) was dissolved in chloroform (25 L) and cooled to 0-10° C. To the solution was added 65% mCPBA (8.32 kg, 31.3 mol, 1.3 equivalents), and the resulting suspension was heated at 40-50° C. for 10 hours. The reaction mixture was cooled to 10° C. and stirred for 15 minutes. This suspension was filtered, and the residue was washed with chloroform (20 L).

The combined filtrates were dried over anhydrous sodium sulfate, and filtered. To the resulting filtrate was added acetic anhydride (12.2 L, 129 mol, 5.4 equivalents) at room temperature, and the mixture was heated and stirred at 65-70° C. for 12 hours. After completion of the reaction, the reaction mixture was cooled to room temperature. To the reaction mixture was added methanol (35 L), and the mixture was stirred for 2 hours. This reaction mixture was concentrated under reduced pressure. To the residue were added n-hexane (40 L) and water (30 L), and the mixture was stirred for 30 minutes. It was filtered, and the residue was washed with n-hexane (15 L). All the filtrates were combined, and the aqueous layer was separated. The organic layer was washed sequentially with water (2×30 L) and a 10% aqueous sodium hydrogen carbonate solution (25 L). The organic layer was dried over anhydrous sodium sulfate, and the filtered solution was concentrated under reduced pressure. The residue was purified with silica gel column chromatography (10% ethyl acetatein-hexane) to afford the title compound (2.34 kg).

(2) Synthesis of (6-methoxy-3-(4,4,5,5-tetramethyl-1,3,2-dioxaborolan-2-yl)pyridin-2-yl)methyl acetate A mixed solution of (3-bromo-6-methoxypyridin-2-yl)methyl acetate (1.0 kg, 3.85 mol, 1 equivalent), bis(pinacolato)diborane (1.47 kg, 5.79 mol, 1.5 equivalents) and potassium acetate (1.14 kg, 11.6 mol, 3 equivalents) in DMSO (200 mL) and 1,4-dioxane (10 L) was bubbled with argon for 20 minutes. To the solution was added Pd(dppf)Cl$_2$ (141 g, 193 mmol, 0.05 equivalents), and argon was bubbled through the solution for another 10 minutes. The reaction mixture was heated to reflux for 16 hours before being cooled down to room temperature. The reaction mixture was concentrated under reduced pressure. To the residue were added water and n-hexane, and the mixture was filtered through Celite™. The organic and aqueous layers of the filtrate were separated, and the aqueous layer was extracted again with n-hexane. The combined organic layers were dried over anhydrous sodium sulfate, and the filtered solution was concentrated under reduced pressure to afford the title compound (1.80 kg) as a crude product. This crude product was used for the next reaction without further purification.

(3) Synthesis of (3-(benzyloxy)-6'-methoxy-[2,3'-bipyridin]-2'-yl)methanol

A mixture of 3-(benzyloxy)-2-bromopyridine (CAS No. 132330-98-4) (900 g, 3410 mmol), (6-methoxy-3-(4,4,5,5-tetramethyl-1,3,2-dioxaborolan-2-yl)pyridin-2-yl)methyl acetate (1.80 kg), cesium carbonate (2.22 kg, 6.81 mol), DME (18 L) and water (1.8 L) was bubbled with argon for 20 minutes. To the solution was added Pd(PPh$_3$)$_4$ (80 g, 69.2 mmol), and argon was bubbled through the solution for another 10 minutes. The reaction mixture was heated to reflux for 18 hours before being cooled down to 60° C., and water (5 L) and a 6 N aqueous sodium hydroxide solution (5 L) were added. This solution was stirred at 50-60° C. for 2 hours and cooled down to room temperature. To the reaction mixture was added ethyl acetate (10 L), and the organic and aqueous layers were separated. The organic layer was extracted with 2 M hydrochloric acid (2×5 L). This aqueous layer was basified with a 6 N aqueous sodium hydroxide solution (5 L), and extracted with ethyl acetate (3×5 L). The organic layer was dried over anhydrous sodium sulfate and filtered, before the resulting solution was concentrated under reduced pressure to about one half of the original solution volume. To this solution was added activated carbon, and the mixture was heated to reflux for 30 minutes and cooled down to room temperature before being filtered through Celite™. The filtrate was concentrated under reduced pressure. The resulting residue was stirred in a solution of 2% MTBE in n-hexane overnight, and the resulting solids were collected by filtration to afford the title compound (760 g).

(4) Synthesis of 2'-(hydroxymethyl)-6'-methoxy-[2,3'-bipyridin]-3-ol

A 5 L stainless steel pressure reactor was charged with a suspension of 10% palladium on carbon (water content, 50%) (33.0 g) in ethanol (3.3 L) under a nitrogen atmosphere. To the suspension was slowly added (3-(benzyloxy)-6'-methoxy-[2,3'-bipyridin]-2'-yl)methanol (330 g, 1020 mmol). The reaction mixture was hydrogenated at room temperature under a pressure of 150 psi for 20 hours. After completion of the reaction, the reaction vessel was purged with nitrogen. The reaction mixture was filtered through Celite™, and the residue was washed with methanol (2.5 L). The combined filtrates were concentrated under reduced pressure, and the resulting residue was suspended in n-hexane, and the resultant was filtered and dried to afford the title compound (225 g).

(5) Synthesis of 6H-pyrano[3,2-b:5,4-b']dipyridin-8(7H)-one

To a solution of 2'-(hydroxymethyl)-6'-methoxy-[2,3'-bipyridin]-3-ol (225 g, 969 mmol, 1 equivalent) and triphenylphosphine (308 g, 1170 mmol, 1.2 equivalents) in DCM (4.5 L) was added dropwise DIAD (230 mL, 1180 mmol, 1.2 equivalents) at 0-10° C. The reaction mixture was stirred at room temperature overnight before DCM and water were added, and the organic layer was separated. The aqueous layer was extracted again with DCM. The combined organic layers were dried over sodium sulfate, filtered, and the filtrate was concentrated under reduced pressure. To the residue were added 1,4-dioxane (2.25 L) and concentrated hydrochloric acid (1.13 L). The reaction mixture was heated to reflux overnight before being stirred at room temperature for 30 minutes, and the precipitate was collected by filtration. To the resulting solid were added water (2.5 L) and an aqueous ammonia solution (250 mL), and the mixture was stirred at room temperature for 30 minutes, and the precipitate was collected by filtration. The resulting solid was stirred in acetone (1 L) at room temperature for 30 minutes, and the precipitate was collected by filtration. The resulting solid was dried to afford the title compound (160 g).

$^1$H-NMR (400 MHz, DMSO-d$_6$) δ (ppm): 5.15 (s, 2H), 6.35-6.55 (m, 1H), 7.12-7.18 (m, 1H), 7.25-7.32 (m, 1H), 8.03-8.13 (m, 1H), 8.13-8.21 (m, 1H), 11.82 (br, s, 1H).

Production Example 2

Synthesis of 9-bromo-7-(pyridin-3-yl)-6H-pyrano[3,2-b:5,4-b']dipyridin-8(7H)-one

[Chemical Formula 57]

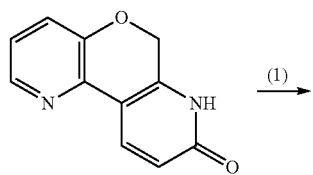

(1)

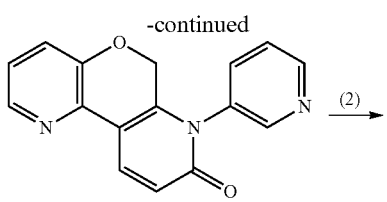

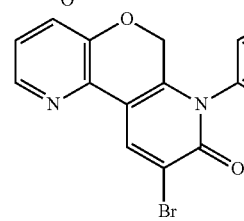

(1) Synthesis of 7-(pyridin-3-yl)-6H-pyrano[3,2-b:5,4-b']dipyridin-8(7H)-one To a mixture of 6H-pyrano[3,2-b:5,4-b']dipyridin-8(7H)-one obtained in Production Example 1 (4 g, 20.0 mmol, 1 equivalent), silver carbonate (6.61 g, 24.0 mmol, 1.2 equivalents), copper(I) iodide (2.28 g, 12.0 mmol, 0.6 equivalents), pyridine (9.7 mL, 120 mmol, 6 equivalents) and DMF (100 mL) was slowly added a suspension of pyridine-3-boronic acid 1,3-propanediol cyclic ester (CAS No. 131534-65-1) (9.77 g, 59.9 mmol, 3 equivalents) in DMF (100 mL) at 65° C. under an oxygen atmosphere. The reaction mixture was stirred at 65° C. overnight. The reaction solution was cooled down to room temperature, and NH silica gel was added. The mixture was filtered through Celite™, and the residue was washed with chloroform. The resulting filtrate was concentrated under reduced pressure. The resulting residue was purified with silica gel column chromatography (NH silica gel on silica gel, 10%-100% ethyl acetate/n-heptane, 5% methanol/ethyl acetate) to afford the title compound (610 mg).

$^1$H-NMR (400 MHz, CDCl$_3$) δ (ppm): 4.65 (d, J=15.4 Hz, 1H), 4.79 (d, J=15.4 Hz, 1H), 6.74-6.81 (m, 1H), 7.06-7.18 (m, 2H), 7.49-7.59 (m, 1H), 7.64-7.74 (m, 1H), 8.21-8.30 (m, 1H), 8.32-8.38 (m, 1H), 8.51-8.56 (m, 1H), 8.75-8.82 (m, 1H),

(2) Synthesis of 9-bromo-7-(pyridin-3-yl)-6H-pyrano[3,2-b:5,4-b']dipyridin-8(7H)-one A mixture of 7-(pyridin-3-yl)-6H-pyrano[3,2-b:5,4-b']dipyridin-8(7H)-one (300 mg, 1.08 mmol, 1 equivalent), NBS (231 mg, 1.30 mmol, 1.2 equivalents) and DMF (9 mL) was stirred at room temperature for 4 hours. To the reaction mixture was added water, and the mixture was extracted with ethyl acetate. The organic layer was washed with a saturated aqueous sodium chloride solution, and concentrated under reduced pressure. The residue was purified with silica gel column chromatography (silica gel, 5%-100% ethyl acetate/n-heptane) to afford the title compound (277 mg).

$^1$H-NMR (400 MHz, CDCl$_3$) δ (ppm): 4.59-4.66 (m, 1H), 4.72-4.79 (m, 1H), 7.10-7.14 (m, 1H), 7.15-7.19 (m, 1H), 7.53-7.58 (m, 1H), 7.66-7.71 (m, 1H), 8.26 (dd, J=4.6, 1.7 Hz, 1H), 8.52-8.55 (m, 1H), 8.78 (s, 1H), 8.80 (dd, J=4.8, 1.7 Hz, 1H).

Production Example 3

Synthesis of 9-bromo-7-(thiophen-3-yl)-6H-pyrano[3,2-b:5,4-b']dipyridin-8(7H)-one

[Chemical Formula 58]

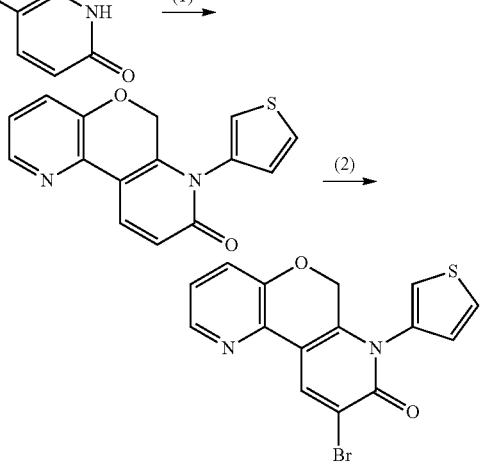

(1) Synthesis of 7-(thiophen-3-yl)-6H-pyrano[3,2-b:5,4-b']dipyridin-8(7H)-one A mixture of 6H-pyrano[3,2-b:5,4-b']dipyridin-8(7H)-one obtained in Production Example 1 (1 g, 5.00 mmol, 1 equivalent), thiophene-3-boronic acid (CAS No. 6165-69-1) (1.28 g, 9.99 mmol, 2 equivalents), silver carbonate (1.65 g, 5.99 mmol, 1.2 equivalents), copper(I) iodide (571 mg, 3.00 mmol, 0.6 equivalents), pyridine (2.42 mL, 30.0 mmol, 6 equivalents) and DMF (40 mL) was stirred at 70° C. for 3 days. The reaction mixture was allowed to return to room temperature before being applied to silica gel pad (NH silica gel and silica gel) and elated with ethyl acetate. The resulting solution was concentrated under reduced pressure, and the residue was purified with silica gel column chromatography (NH silica gel on silica gel, 10%400% ethyl acetate/n-heptane) to afford the title compound (129 mg).

$^1$H-NMR (400 MHz, CDCl$_3$) δ (ppm): 4.79 (br. s, 2H), 6.71-6.77 (m, 1H), 7.04-7.07 (m, 1H), 7.07-7.10 (m, 1H), 7.11-7.17 (m, 1H), 7.28-7.32 (m, 1H), 7.50-7.56 (m, 1H), 8.21-8.25 (m, 1H), 8.26-8.31 (m, 1H).

MS [M+H]$^+$=283

(2) Synthesis of 9-bromo-7-(thiophen-3-yl)-6H-pyrano[3,2-b:5,4-b']dipyridin-8(7H)-one A mixture of 7-(thiophen-3-yl)-6H-pyrano[3,2-b:5,4-b']dipyridin-8(7H)-one (129 mg, 0.457 mmol, 1 equivalent), NBS (98 mg, 0.548 mmol, 1.2 equivalents) and DMF (3 mL) was stirred at room temperature for 15 hours. To the reaction mixture was added ice and water. The mixture was stirred at room temperature for 1 hour, before the precipitate was collected by filtration. The resulting solid was washed with water and n-heptane to afford the title compound (132 mg).

$^1$H-NMR (400 MHz, CDCl$_3$) δ (ppm): 4.77 (br. s, 2H), 7.03-7.06 (m, 1H), 7.08-7.12 (m, 1H), 7.13-7.17 (m, 1H), 7.29-7.33 (m, 1H), 7.51-7.56 (m, 1H), 8.21-8.26 (m, 1H), 8.72 (s, 1H).

MS [M+Na]$^+$=383

Production Example 4

Synthesis of 9-bromo-7-(4-fluorophenyl)-6H-pyrano[3,2-b:5,4-b']dipyridin-8(7H)-one

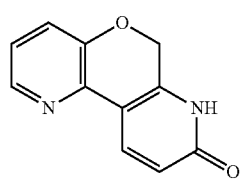

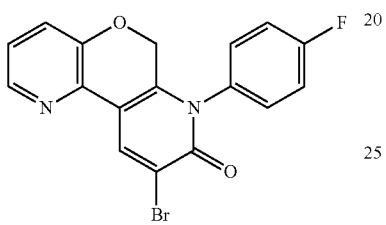

(1) Synthesis of 9-bromo-7-(4-fluorophenyl)-6H-pyrano[3,2-b:5,4-b']dipyridin-8(7H)-one A mixture of 6H-pyrano[3,2-b:5,4-b']dipyridin-8(7H)-one obtained in Production Example 1 (5 g, 25.0 mmol, 1 equivalent), 4-fluorobenzeneboronic acid (CAS No. 1765-93-1) (8.39 g, 59.9 mmol, 2.4 equivalents), silver carbonate (8.26 g, 30.0 mmol, 1.2 equivalents), copper(I) iodide (2.85 g, 15.0 mmol, 0.6 equivalents), pyridine (12.1 mL, 150 mmol, 6 equivalents) and DMF (200 mL) was stirred at 70° C. under an oxygen atmosphere for 3 days. The reaction mixture was directly applied to silica gel pad (NH silica gel), and eluted with ethyl acetate. The resulting solution was concentrated under reduced pressure. The residue was dissolved in chloroform. To the solution was added NH silica gel, and the mixture was concentrated under reduced pressure. The residue was purified with silica gel column chromatography (NH silica gel, 10%-100% ethyl acetate in heptane). The resulting compound was dissolved in DMF (50 mL). To the solution was added NBS (4.01 g, 22.5 mmol, 0.9 equivalents), and the reaction mixture was stirred at room temperature overnight. To the reaction mixture were added ice and water. The mixture was stirred at room temperature for 2 hours, and then the precipitate was collected by filtration. The resulting solid was washed with water and n-heptane to afford the title compound (4.81 g).

$^1$H-NMR (400 MHz, CDCl$_3$) δ (ppm): 4.68 (s, 2H), 7.08-7.13 (m, 1H), 7.13-7.17 (m, 1H), 7.23-7.27 (m, 4H), 8.25 (dd, J=4.7, 1.6 Hz, 1H), 8.75 (s, 1H).

MS [M+Na]$^+$=395

Production Example 5

Synthesis of tributyl(2,6-difluorophenyl)stannane

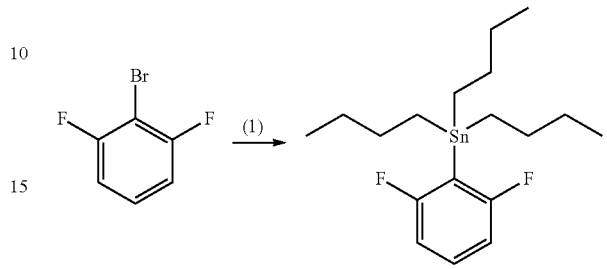

(1) Synthesis of tributyl(2,6-difluorophenyl)stannane

To a solution of 1-bromo-2,6-difluorobenzene (CAS No. 64248-56-2) (5.15 g, 26.7 mmol, 1 equivalent) in THF (100 mL) was added n-butyllithium (2.65 M solution in n-hexane, 11.6 mL, 30.7 mmol, 1.15 equivalents) at −78° C. The reaction mixture was stirred at −78° C. for 30 minutes. To the reaction mixture was added tri-n-butyltin chloride (8.69 mL, 32.0 mmol, 1.2 equivalents). The reaction mixture was allowed to warm up to room temperature over 2 hours. The reaction mixture was concentrated under reduced pressure. To the residue was added water, and the mixture was extracted with DCM. The organic layer was concentrated under reduced pressure, and the residue was purified with silica gel column chromatography (NH silica gel, n-heptane) to afford the title compound (9.38 g).

$^1$H-NMR (400 MHz, CDCl$_3$) δ (ppm): 0.83-0.93 (m, 9H), 1.08-1.24 (m, 6H), 1.27-1.38 (m, 6H), 1.46-1.62 (m, 6H), 6.77-6.84 (m, 2H), 7.21-7.30 (m, 1H).

Production Example 6

Synthesis of tributyl(2,3,5,6-tetrafluorophenyl)stannane

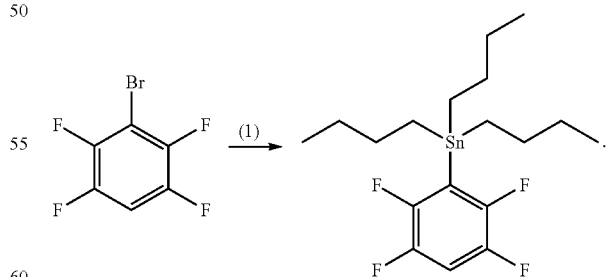

(1) Synthesis of tributyl(2,3,5,6-tetrafluorophenyl)stannane

To a solution of 1-bromo-2,3,5,6-tetrafluorobenzene (CAS No. 1559-88-2) (1 g, 4.37 mmol, 1 equivalent) in THF (20 mL) was added n-butyllithium (2.65 M solution in n-hexane, 1.81 mL, 4.80 mmol, 1.1 equivalents) at −78° C. The reaction mixture was stirred at −78° C. for 30 minutes. To the reaction mixture was added tri-n-butyltin chloride (1.42 mL, 5.24 mmol, 1.2 equivalents). The reaction mixture was allowed to warm up to room temperature over 3 hours. The reaction mixture was concentrated under reduced pressure. To the residue was added water, and the mixture was extracted with DCM. The organic layer was concentrated under reduced pressure, and the residue was purified with silica gel column chromatography (NH silica gel, n-heptane) to afford the title compound (1.49 g).

$^1$H-NMR (400 MHz, CDCl$_3$) δ (ppm): 0.84-0.93 (m, 9H), 1.17-1.39 (m, 12H), 1.46-1.63 (m, 6H), 6.92-7.02 (m, 1H).

Production Example 7

Synthesis of 3-(methoxymethoxy)-2-(tributylstannyl)pyridine

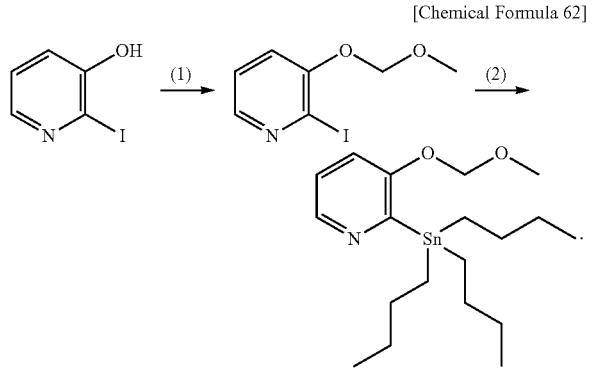

[Chemical Formula 62]

(1) Synthesis of 2-iodo-3-(methoxymethoxy)pyridine

To a solution of 2-iodo-3-hydroxypyridine (CAS No. 40263-57-8) (9.67 g, 43.8 mmol, 1 equivalent) in THF (200 mL) was added sodium hydride (60% oil dispersion, 1.93 g, 48.1 mmol, 1.1 equivalents) at 0° C., and the reaction mixture was stirred at 0° C. for 10 minutes. To the solution was added chloromethyl methyl ether (3.66 mL, 48.1 mmol, 1.1 equivalents), and the mixture was stirred at 0° C. for 10 minutes and at room temperature for 1 hour. To the reaction mixture was added water, and then the mixture was concentrated under reduced pressure. The residue was extracted with chloroform, and the organic layer was concentrated under reduced pressure. The residue was purified with silica gel column chromatography (NH silica gel, 0%-40% ethyl acetate/n-heptane) to afford the title compound (9.9 g).

$^1$H-NMR (400 MHz, CDCl$_3$) δ (ppm): 3.52 (s, 3H), 5.27 (s, 2H), 7.18 (dd, J=8.2, 4.5 Hz, 1H), 7.28 (dd, J=8.2, 1.6 Hz, 1H), 8.06 (dd, J=4.5, 1.6 Hz, 1H).

MS [M+H]$^+$=266

(2) Synthesis of 3-(methoxymethoxy)-2-(tributylstannyl)pyridine

To a solution of n-butyllithium (2.69 M solution in n-hexane, 27.8 mL, 74.7 mmol, 2 equivalents) in THF (150 mL) was added a solution of 2-iodo-3-(methoxymethoxy)pyridine (9.9 g, 37.4 mmol, 1 equivalent) in THF (30 mL) at −78° C. The reaction mixture was stirred at −78° C. for 20 minutes. To the reaction mixture was added tri-n-butyltin chloride (11.2 mL, 41.1 mmol, 1.1 equivalents). The reaction mixture was stirred at −78° C. for 40 minutes and at room temperature for 1.5 hours. The reaction mixture was concentrated under reduced pressure, and the residue was extracted with DCM. The organic layer was concentrated under reduced pressure, and the residue was purified with neutral alumina (n-heptane). The resulting crude product was purified again with silica gel column chromatography (NH silica gel, 0%-10% ethyl acetate/n-heptane) to afford the title compound (11.4 g).

$^1$H-NMR (400 MHz, CDCl$_3$) δ (ppm): 0.84-0.91 (m, 9H), 1.04-1.22 (m, 6H), 1.26-1.38 (m, 6H), 1.46-1.64 (m, 6H), 3.47 (s, 3H), 5.16 (s, 2H), 7.05-7.11 (m, 1H), 7.23-7.26 (m, 1H), 8.40-8.44 (m, 1H).

MS [M+H]$^+$=430

Production Example 8

Synthesis of 6H-pyrano[3,2-b:5,4-b']dipyridin-8(7H)-one

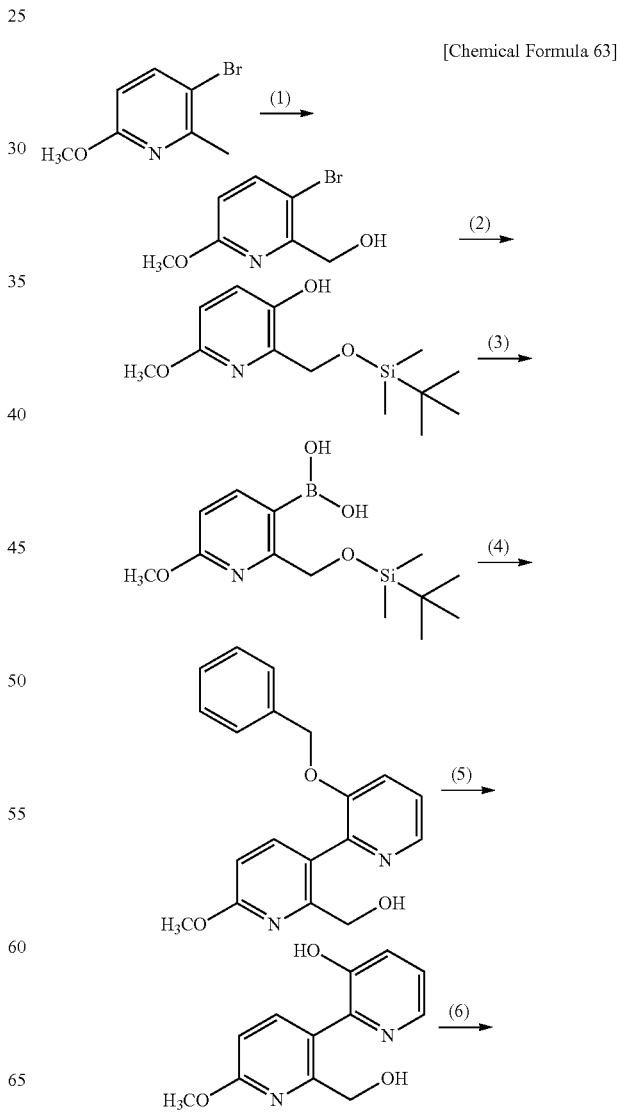

[Chemical Formula 63]

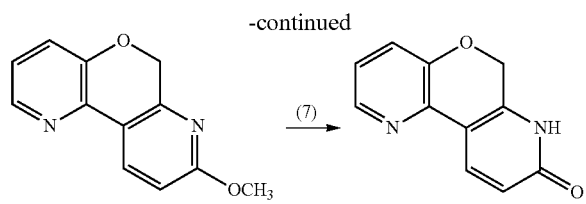

(1) Synthesis of (3-bromo-6-methoxypyridin-2-yl)methanol

To a solution of 3-bromo-6-methoxy-2-methylpyridine (CAS No. 126717-59-7) (5.5 g, 27.2 mmol, 1 equivalent) in chloroform (100 mL) was added 65% mCPBA (10.8 g, 40.8 mmol, 1.5 equivalents) at 0° C. The reaction mixture was warmed up to room temperature and stirred for 24 hours. To the reaction mixture were added an aqueous sodium thiosulfate pentahydrate solution and a saturated aqueous sodium hydrogen carbonate solution, and the mixture was extracted with chloroform. The resulting organic layer was dried over magnesium sulfate, filtered, and then concentrated under reduced pressure. The residue was purified with silica gel column chromatography (silica gel, 0%-20% methanol/ethyl acetate). The resulting compound was stirred in acetic anhydride (20 mL) at 120° C. for 3 hours. To the reaction mixture was added methanol, and the mixture was concentrated under reduced pressure. To the residue was added water, and the mixture was extracted with ethyl acetate. The combined organic layers were washed with a saturated aqueous sodium chloride solution. The organic layers were dried over magnesium sulfate, filtered, and then concentrated under reduced pressure. The resulting residue was purified with silica gel column chromatography (silica gel, 20%-75% ethyl acetate/n-heptane). To the resulting compound in methanol (22 mL) was added potassium carbonate (1 M aqueous solution, 10.4 mL) at room temperature. After stirring at the same temperature for 1 hour, the reaction mixture was concentrated under reduced pressure. To the residue was added water, and the mixture was extracted with chloroform. The combined organic layers were washed with a saturated aqueous sodium chloride solution. The organic layers were dried over magnesium sulfate, filtered, and then concentrated under reduced pressure to afford the title compound (1.75 g).

$^1$H-NMR (400 MHz, CDCl$_3$) δ (ppm): 3.97 (s, 3H), 4.03 (t, J=4.7 Hz, 1H), 4.68 (dd, J=4.7, 0.8 Hz, 2H), 6.57-6.64 (m, 1H), 7.69 (d, J=8.6 Hz, 1H).

(2) Synthesis of 3-bromo-2-(((t-butyldimethylsilyl)oxy)methyl)-6-methoxypyridine To a solution of (3-bromo-6-methoxypyridin-2-yl)methanol (1.75 g, 8.03 mmol, 1 equivalent) in DCM were sequentially added t-butyldimethylchlorosilane (1.45 g, 9.63 mmol, 1.2 equivalents) and imidazole (0.656 g, 9.63 mmol, 1.2 equivalents) at room temperature. After stirring at the same temperature for 3 hours, to the reaction mixture was added water, and the mixture was extracted with DCM. The combined organic layers were washed with a saturated aqueous sodium chloride solution. The organic layers were dried over magnesium sulfate, filtered, and then concentrated under reduced pressure. The residue was purified with silica gel column chromatography (silica gel, 5%-25% ethyl acetate/n-heptane) to afford the title compound (2.36 g).

MS [M+H]$^+$=332

(3) Synthesis of (2-(((t-butyldimethylsilyl)oxy)methyl)-6-methoxypyridin-3-yl)boronic acid To a mixture of 3-bromo-2-(((t-butyldimethylsilyl)oxy)methyl)-6-methoxypyridine (12 g, 36.1 mmol, 1 equivalent), DMSO (24 mL) and 1,4-dioxane (144 mL) were sequentially added potassium acetate (10.6 g, 108 mmol, 3 equivalents) and bis(pinacolato)diborane (16.1 g, 63.2 mmol, 1.75 equivalents) at room temperature. After degassing, Pd(dppf)Cl$_2$ (1.32 g, 1.81 mmol, 0.05 equivalents) was added. The reaction mixture was stirred at 80-85° C. for 20 hours. The reaction mixture was cooled down to room temperature, and water was added, and the mixture was extracted with DCM. The combined organic layers were washed with a saturated aqueous sodium chloride solution. The organic layers were dried over magnesium sulfate, filtered, and then concentrated under reduced pressure. The residue was purified with silica gel column chromatography (silica gel, 4.8%-25% ethyl acetate/n-heptane) to afford a crude product (20 g). 12 g of the resulting crude product was used for the next reaction. To a mixture of the crude product (12 g), ammonium acetate (12.2 g, 158 mmol), acetone (200 mL) and water (100 mL) was added sodium periodate (33.8 g, 158 mmol) at room temperature. After stirring at the same temperature overnight, the reaction mixture was filtered, and the filtrate was concentrated under reduced pressure. To the residue was added water, and the mixture was extracted with DCM. The combined organic layers were washed with a saturated aqueous sodium chloride solution. The organic layers were dried over magnesium sulfate, filtered, and then concentrated under reduced pressure. The residue was purified with silica gel column chromatography (silica gel, 5%-25% ethyl acetate/n-heptane) to afford the title compound (5.5 g).

$^1$H-NMR (400 MHz, CDCl$_3$) δ (ppm): 0.10 (s, 6H), 0.89 (s, 9H), 3.94 (s, 3H), 4.84 (s, 2H), 6.60-6.85 (m, 3H), 8.06-8.13 (m, 1H).

(4) Synthesis of (3-(benzyloxy)-6'-methoxy-[2,3'-bipyridin]-2'-yl)methanol

To an aqueous solution of (2-(((t-butyldimethylsilyl)oxy)methyl)-6-methoxypyridin-3-yl)boronic acid (10.5 g, 35.4 mmol, 1.1 equivalents) and 3-(benzyloxy)-2-bromopyridine (CAS No. 132330-98-4) (8.5 g, 32.2 mmol, 1 equivalent) in 1,4-dioxane were sequentially added cesium carbonate (12.6 g, 38.6 mmol, 1.2 equivalents) and Pd(PPh$_3$)$_4$ (1.86 g, 1.61 mmol, 0.05 equivalents) at room temperature. After stirring at the same temperature for 10 minutes, the reaction mixture was stirred at 100° C. for 18 hours. The reaction mixture was allowed to return to room temperature, and water was added, and the mixture was extracted with ethyl acetate. The combined organic layers were washed with a saturated aqueous sodium chloride solution. The organic layers were dried over magnesium sulfate, filtered, and then concentrated under reduced pressure. The residue was applied to silica gel pad (NH silica gel), and eluted with ethyl acetate. The resulting solution was concentrated under reduced pressure. To a solution of the resulting compound in THF was added TBAF (1 M solution in THF, 40.2 mL, 40.2 mmol, 1.25 equivalents) at room temperature. After stirring for 3 hours, the reaction mixture was concentrated under reduced pressure. The residue was purified with silica gel column chromatography (silica gel, 5%-67% ethyl acetate/n-heptane) to afford the title compound (11 g).

(4-2) Synthesis of (3-(benzyloxy)-6'-methoxy-[2,3'-bipyridin]-2'-yl)methanol

To a mixture of (2-(((t-butyldimethylsilyl)oxy)methyl)-6-methoxypyridin-3-yl)boronic acid (19.4 g, 65.2 mmol, 1.1 equivalents), 3-(benzyloxy)-2-bromopyridine (CAS No. 132330-98-4) (15.7 g, 59.3 mmol, 1 equivalent), 1,4-dioxane (200 mL) and water (20 mL) were sequentially added cesium carbonate (23.2 g, 71.1 mmol, 1.2 equivalents) and Pd(PPh$_3$)$_4$ (3.43 g, 2.96 mmol, 0.05 equivalents) at room temperature. After stirring at the same temperature for 10 minutes, the reaction mixture was stirred at 100° C. for 18 hours. The reaction mixture was allowed to return to room temperature, and water was added, and the mixture was extracted with ethyl acetate. The combined organic layers were washed with a saturated aqueous sodium chloride solution. The organic layers were dried over magnesium sulfate, filtered, and then concentrated under reduced pressure. The residue was applied to silica gel pad (NH silica gel), and eluted with ethyl acetate. The resulting solution was concentrated under reduced pressure. To a solution of the resulting compound in THF (150 mL) was added TBAF (1 M solution in THF, 71.1 mL, 71.1 mmol, 1.2 equivalents) at room temperature. After stirring for 4 hours, the reaction mixture was concentrated under reduced pressure. The residue was purified with silica gel column chromatography (silica gel, 50%-67% ethyl acetate/n-heptane) to afford the title compound (20.3 g).

(5) Synthesis of 2'-(hydroxy-methyl)-6'-methoxy-[2,3'-bipyridin]-3-ol

To a solution of (3-(benzyloxy)-6'-methoxy-[2,3'-bipyridin]-2'-yl)methanol (11 g, 34.1 mmol) in ethyl acetate was added 10% palladium on carbon (water content, 50%) (3 g) at room temperature under a nitrogen atmosphere. The reaction mixture was stirred under a hydrogen atmosphere for 1 hour. The reaction mixture was filtered through Celite™, and the residue was washed with ethyl acetate. The resulting filtrate was concentrated under reduced pressure. The residue was purified with silica gel column chromatography (silica gel, 10%-100% ethyl acetate/n-heptane) to afford the title compound (8 g).

(6) Synthesis of 8-methoxy-6H-pyrano[3,2-b:5,4-b']dipyridine

To a solution of 2'-(hydroxymethyl)-6'-methoxy-[2,3'-bipyridin]-3-ol (8 g, 34.4 mmol, 1 equivalent) in THF were sequentially added triphenylphosphine (9.94 g, 37.9 mmol, 1.1 equivalents) and DMEAD (8.87 g, 37.9 mmol, 1.1 equivalents) at 0° C. After stirring at the same temperature for 30 minutes, the reaction mixture was stirred at room temperature for 2 hours. The reaction mixture was concentrated under reduced pressure. The residue was purified with silica gel column chromatography (silica gel, 10%-67% ethyl acetate/n-heptane) to afford the title compound (5.53 g).
$^1$H-NMR (400 MHz, CDCl$_3$) δ (ppm): 3.96 (s, 3H), 5.24 (s, 2H), 6.79 (d, J=8.6 Hz, 1H), 7.10 (dd, J=8.2, 4.7 Hz, 1H), 7.21 (dd, J=8.2, 1.2 Hz, 1H), 8.23 (dd, J=4.7, 1.2 Hz, 1H), 8.34 (d, J=8.6 Hz, 1H).

(7) Synthesis of 6H-pyrano[3,2-b:5,4-b']dipyridin-8(7H)-one

A mixture of 8-methoxy-6H-pyrano[3,2-b:5,4-b']dipyridine (5.4 g, 25.2 mmol, 1 equivalent) and pyridine hydrochloride (29.1 g, 252 mmol, 10 equivalents) was stirred at 150° C. for 1 hour. To the reaction mixture was added water, and the precipitate was collected by filtration. The resulting solid was washed with water and dried to afford the title compound (3.8 g).
$^1$H-NMR (400 MHz, DMSO-d$_6$) δ (ppm): 5.15 (s, 2H), 6.35-6.55 (m, 1H), 7.12-7.18 (m, 1H), 7.25-7.32 (m, 1H), 8.03-8.13 (m, 1H), 8.13-8.21 (m, 1H), 11.90 (br. s, 1H).

Production Example 9

Synthesis of benzyl (3-(3-(benzyloxy)pyridin-2-yl)-4-methoxy-2-oxobut-3-en-1-yl)carbonate (E/Z mixture)

[Chemical Formula 64]

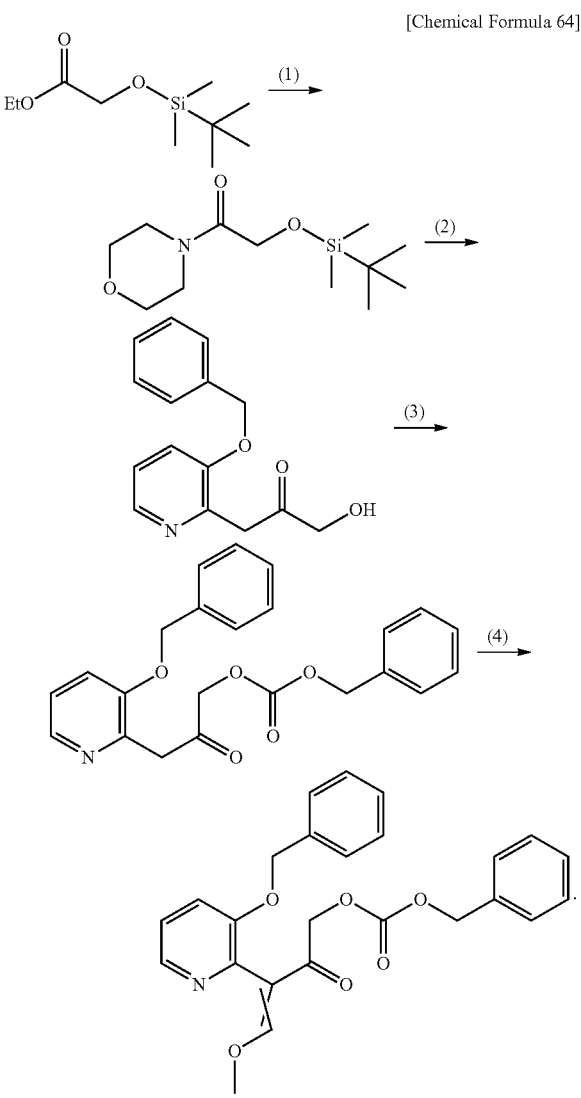

(1) Synthesis of 2-((t-butyldimethylsilyl)oxy)-1-morpholinoethanone

A mixture of 2,3,4,6,7,8-hexahydro-1H-pyrimido[1,2-a]pyrimidine (1.91 g, 13.7 mmol, 0.3 equivalents), ethyl 2-((t-butyldimethylsilyl)oxy)acetate (p. 27 of Supporting Information for Journal of the American Chemical Society, 2011, 133(35), 14082-14089) (CAS No. 67226-78-2) (10 g, 45.8 mmol, 1 equivalent), morpholine (4.41 mL, 50.4 mmol, 1.1 equivalents) and 2-methyltetrahydrofuran (50 mL) was stirred at 60° C. overnight. The reaction mixture was allowed to return to room temperature, and then washed sequentially with a 5% aqueous ammonium chloride solution and water. The solution was concentrated under reduced pressure to afford the title compound (10.4 g).

$^1$H-NMR (400 MHz, CDCl$_3$) δ (ppm): 0.11 (s, 6H), 0.90 (s, 9H), 3.54-3.74 (m, 8H), 4.29 (s, 2H).

MS [M+H]$^+$=260

(2) Synthesis of 1-(3-(benzyloxy)pyridin-2-yl)-3-hydroxypropan-2-one

To a solution of 3-(benzyloxy)-2-methylpyridine (p. 22 of Supporting Information for Journal of Medicinal Chemistry, 2008, 51(15), 4708-4714) (CAS No. 177559-01-2) (4.4 g, 22.1 mmol, 1 equivalent) in 2-methyltetrahydrofuran (44 mL) was added n-butyllithium (2.65 M solution in n-hexane, 10.0 mL, 26.5 mmol, 1.2 equivalents) at −78° C. The reaction mixture was stirred at −78° C. for 1 hour. The reaction mixture was added dropwise to a solution of 2-((t-butyldimethylsilyl)oxy)-1-morpholinoethanone (6.87 g, 26.5 mmol, 1.2 equivalents) in 2-methyltetrahydrofuran (13.2 mL) at −78° C. The reaction mixture was stirred at −78° C. for 30 minutes. To the reaction mixture was added a 5% aqueous ammonium chloride solution, and the mixture was allowed to warm up to room temperature. The organic layer was separated. The resulting organic layer was washed with a 5% aqueous ammonium chloride solution. To the resulting organic layer was added 2 N hydrochloric acid (26.4 mL, 52.8 mmol, 2.39 equivalents), and the mixture was stirred at room temperature for 2 hours. The aqueous layer was separated. The resulting aqueous layer was neutralized with a 2 N aqueous sodium hydroxide solution, and extracted with ethyl acetate. The organic layer was dried over sodium sulfate and filtered, and then the resulting solution was concentrated under reduced pressure at 60° C. to approximately five times the volume of 3-(benzyloxy)-2-methylpyridine used. The remaining solution was cooled down to room temperature. To this mixture was added n-heptane (50 mL). The precipitate was collected by filtration. The resulting solid was washed with MTBE to afford the title compound (3.53 g).

$^1$H-NMR (400 MHz, CDCl$_3$) δ (ppm): 3.48 (br. s, 1H), 4.03 (s, 2H), 4.28 (s, 2H), 5.08 (s, 2H), 7.12-7.25 (m, 2H), 7.30-7.55 (m, 5H), 8.16 (dd, J=4.7, 1.6 Hz, 1H).

MS [M+H]$^+$=258

(3) Synthesis of benzyl (3-(3-(benzyloxy)pyridin-2-yl)-2-oxopropyl)carbonate To a solution of 1-(3-(benzyloxy)pyridin-2-yl)-3-hydroxypropan-2-one (21 g, 81.6 mmol, 1 equivalent) in THF (210 mL) were added pyridine (8.58 mL, 106 mmol, 1.3 equivalents) and 1-carbobenzoxy-3-methylimidazolium triflate (CAS No. 163080-99-7) (35.9 g, 97.9 mmol, 1.2 equivalents) at 0° C. The reaction mixture was stirred at room temperature for 16 hours, then MTBE, acetic acid (8.5 mL) and water were added, and the organic layer was separated. The organic layer was washed sequentially with water and a saturated aqueous sodium chloride solution. The organic layer was dried over anhydrous sodium sulfate, filtered, and then concentrated under reduced pressure to afford the title compound (33 g) as a crude product. This crude product was used for the next reaction without further purification.

MS [M+H]$^+$=392

(4) Synthesis of benzyl (3-(3-(benzyloxy)pyridin-2-yl-4-methoxy-2-oxobut-3-en-1-yl)carbonate (E/Z mixture)

To a mixture of benzyl (3-(3-(benzyloxy)pyridin-2-yl)-2-oxopropyl)carbonate (33 g) and trimethyl orthoformate (CAS No. 149-73-5) (66 mL, 603 mmol) were added acetic anhydride (132 mL, 1.40 mol) and acetic acid (66 mL, 1.15 mol) at room temperature. The reaction mixture was stirred at 70° C. for 3 hours. The reaction mixture was concentrated under reduced pressure. The residue was purified with silica gel column chromatography (silica gel, 15%-100% ethyl acetate/n-heptane) to afford the title compound (29.2 g).

$^1$H-NMR (400 MHz, CDCl$_3$) δ (ppm): 3.84 (s, 0.85×3H), 3.94 (s, 0.15×3H), 4.74 (s, 0.85×2H), 5.04 (s, 0.15×2H), 5.10 (s, 0.85×2H), 5.11 (s, 0.15×2H), 5.17 (s, 0.85×2H), 5.19 (s, 0.15×2H), 7.10-7.43 (m, 0.85×12H and 0.15×13H), 7.64 (s, 0.85×1H), 8.15 (dd, J=4.0, 2.2 Hz, 0.15×1H), 8.27 (dd, J=4.8, 1.5 Hz, 0.85×1H).

MS [M+H]$^+$=434

Example 1

Synthesis of 9-(2-chlorophenyl)-7-(pyridin-3-yl)-6H-pyrano[3,2-b:5,4-b']dipyridin-8(7H)-one

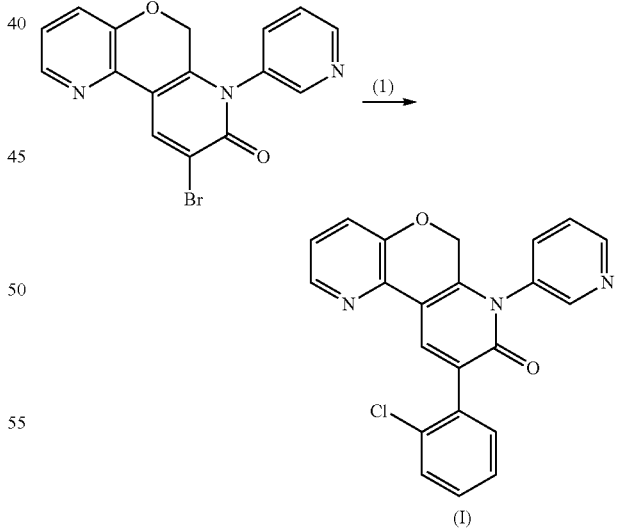

(1) Synthesis of 9-(2-chlorophenyl)-7-(pyridin-3-yl)-6H-pyrano[3,2-b:5,4-b']dipyridin-8(7H)-one A mixture of 9-bromo-7-(pyridin-3-yl)-6H-pyrano[3,2-b:5,4-b']dipyridin-8(7H)-one obtained in Production Example 2 (44.8 mg, 0.126 mmol, 1 equivalent), 2-chlorophenylboronic acid (CAS No. 3900-89-8) (49.2 mg, 0.314 mmol, 2.5 equivalents), Pd(PPh$_3$)$_4$ (15 mg, 0.013 mmol, 0.1 equivalents), cesium carbonate (61.5 mg, 0.189 mmol, 1.5 equivalents) and 1,4-dioxane (2 mL) was reacted in a microwave reactor at 110° C. for 2 hours. To the reaction mixture was added water, and the mixture was separated and extracted with ethyl acetate. The resulting organic layer was washed with a saturated aqueous sodium chloride solution. The organic layer was dried over sodium sulfate, filtered, and then concentrated under reduced pressure. The resulting residue was purified with silica gel column chromatography (50%-100% ethyl acetate/n-heptane) to afford the title compound (36.7 mg).

$^1$H-NMR (400 MHz, CDCl$_3$) δ (ppm): 4.73 (d, J=15.4 Hz, 1H), 4.87 (d, J=15.4 Hz, 1H), 7.09-7.14 (m, 1H), 7.16-7.20 (m, 1H), 7.29-7.34 (m, 2H), 7.42-7.49 (m, 2H), 7.52-7.57 (m, 1H), 7.73-7.78 (m, 1H), 8.24 (dd, J=4.7, 1.6 Hz, 1H), 8.43 (s, 8.58-8.61 (m, 1H), 8.78 (dd, J=4.9, 1.6 Hz, 1H).

MS [M+H]$^+$=388

Example 2

Synthesis of 2-fluoro-6-(7-(5-methoxypyridin-3-yl)-8-oxo-7,8-dihydro-6H-pyrano[3,2-b:5,4-b']dipyridin-9-yl)benzonitrile

[Chemical Formula 66]

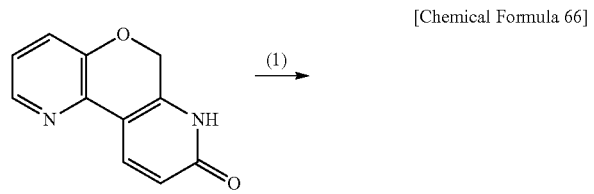

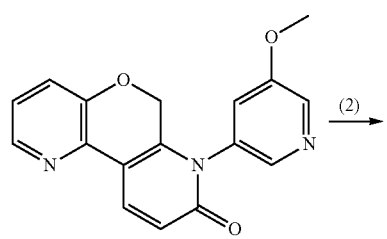

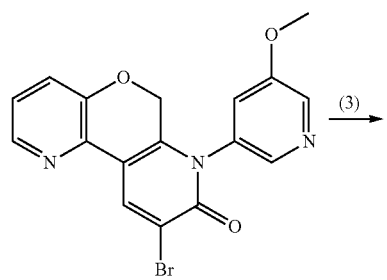

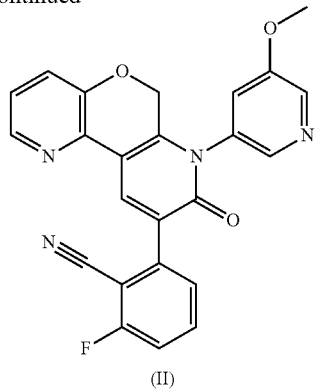

(1) Synthesis of 7-(5-methoxypyridin-3-yl)-6H-pyrano[3,2-b:5,4-b']dipyridin-8(7H)-one To a solution of 6H-pyrano[3,2-b:5,4-b']dipyridin-8(7H)-one obtained in Production Example 1 (500 mg, 2.50 mmol, 1 equivalent) in DMF were sequentially added pyridine (1.21 mL, 15.0 mmol, 6 equivalents), silver carbonate (758 mg, 2.75 mmol, 1.1 equivalents) and copper(I) iodide (476 mg, 2.50 mmol, 1 equivalent) at room temperature. The solution was stirred for 25 minutes, and then a solution of 5-methoxypyridine-3-boronic acid (CAS No. 850991-69-4) (764 mg, 5.00 mmol, 2 equivalents) in DMF was added dropwise at 85° C. over 3 hours. The reaction mixture was stirred overnight, then filtered through Celite™, and the filtrate was concentrated under reduced pressure. The resulting residue was purified with silica gel column chromatography (50%-100% ethyl acetate/n-heptane) to afford the title compound (135 mg).

MS [M+H]$^+$=308

(2) Synthesis of 9-bromo-7-(5-methoxypyridin-3-yl)-6H-pyrano[3,2-b:5,4-b']dipyridin-8(7H)-one To a solution of 7-(5-methoxypyridin-3-yl)-6H-pyrano[3,2-b:5,4-b']dipyridin-8(7H)-one (273 mg, 0.888 mmol, 1 equivalent) in DMF was added NBS (182 mg, 1.02 mmol, 1.15 equivalents) at room temperature. After stirring at the same temperature for 3 hours, to the reaction mixture was added water, and the mixture was extracted with chloroform. The resulting organic layer was washed with a saturated aqueous sodium chloride solution. The organic layer was dried over magnesium sulfate, filtered, and then concentrated under reduced pressure. The resulting residue was purified with silica gel column chromatography (50%-100% ethyl acetate/n-heptane) to afford the title compound (213 mg).

MS [M+H]$^+$=388

(3) Synthesis of 2-fluoro-6-(7-(5-methoxypyridin-3-yl)-8-oxo-7,8-dihydro-6H-pyrano[3,2-b:5,4-b']dipyridin-9-yl)benzonitrile To a solution of 9-bromo-7-(5-methoxypyridin-3-yl)-6H-pyrano[3,2-b:5,4-b']dipyridin-8(7H)-one (45 mg, 0.117 mmol, 1 equivalent) in DME were sequentially added 2-cyano-3-fluorophenylboronic acid pinacol ester (CAS No. 765916-91-4) (43.2 mg, 0.175 mmol, 1.5 equivalents), a 2 M aqueous sodium carbonate solution (87 μL, 0.175 mmol, 1.5 equivalents) and (Ataphos)$_2$PdCl$_2$ (4.13 mg, 5.83 μmol, 0.05 equivalents) at room temperature. The reaction mixture was reacted in a microwave reactor at 100° C. for 1 hour 30 minutes. Subsequently, the reaction mixture was filtered through Celite™, and the filtrate was concentrated under reduced pressure. The resulting residue was purified with silica gel column chromatography (50%-100% ethyl acetate/n-heptane) to afford the title compound (22 mg).

$^1$H-NMR (400 MHz, CDCl$_3$) δ (ppm): 3.93 (s, 3H), 4.74 (d, J=15.6 Hz, 1H), 4.92 (d, J=15.6 Hz, 1H), 7.11-7.29 (m, 4H), 7.44-7.49 (m, 1H), 7.58-7.68 (m, 1H), 8.17 (d, J=2.0 Hz, 1H), 8.25 (dd, J=4.5, 1.4 Hz, 1H), 8.50 (d, J=2.7 Hz, 1H), 8.56 (s, 1H).

MS [M+H]$^+$=427.

Example 3

Synthesis of 2-fluoro-6-(7-(6-methylpyridin-3-yl)-8-oxo-7,8-dihydro-6H-pyrano[3,2-b:5,4-b']dipyridin-9-yl)benzonitrile

[Chemical Formula 67]

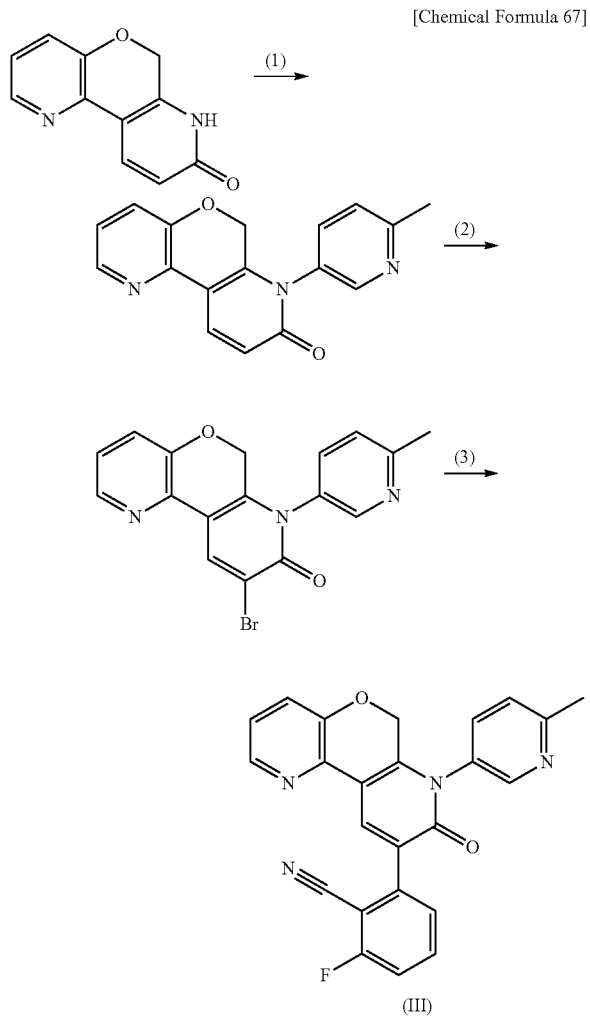

(1) Synthesis of 7-(6-methylpyridin-3-yl)-6H-pyrano[3,2-b:5,4-b']dipyridin-8(7H)-one To a solution of 6H-pyrano[3,2-b:5,4-b']dipyridin-8(7H)-one obtained in Production Example 1 (1 g, 5.00 mmol, 1 equivalent) in DMF were sequentially added pyridine (3.39 mL, 30.0 mmol, 6 equivalents), silver carbonate (1.65 g, 5.99 mmol, 1.2 equivalents) and copper(I) iodide (571 mg, 3.00 mmol, 0.6 equivalents) at room temperature. The reaction mixture was stirred for 25 minutes, and then a solution of 6-methylpyridine-3-boronic acid (CAS No. 659742-21-9) (1.64 g, 12.0 mmol, 2.4 equivalents) in DMF was added dropwise at 95° C. over 3 hours. The reaction mixture was stirred overnight, and then the reaction mixture was filtered through Celite™. The filtrate was concentrated under reduced pressure. The resulting residue was purified with silica gel column chromatography (50%-100% ethyl acetate/n-heptane, 10% methanol/ethyl acetate) to afford the title compound (600 mg).

MS [M+H]$^+$=292

(2) Synthesis of 9-bromo-7-(6-methylpyridin-3-yl)-6H-pyrano[3,2-b:5,4-b']dipyridin-8(7H)-one To a solution of 7-(6-methylpyridin-3-yl)-6H-pyrano[3,2-b:5,4-b']dipyridin-8(7H)-one (600 mg, 2.06 mmol, 1 equivalent) in DMF was added NBS (458 mg, 2.58 mmol, 1.25 equivalents) at room temperature. After stirring at the same temperature for 2 hours, to the reaction mixture was added ice water, and the mixture was extracted with ethyl acetate. The resulting organic layer was washed with a saturated aqueous sodium chloride solution. The organic layer was dried over magnesium sulfate, filtered, and then concentrated under reduced pressure. The resulting residue was purified with silica gel column chromatography (50%-100% ethyl acetate/n-heptane) to afford the title compound (400 mg),

MS [M+H]$^+$=372

(3) Synthesis of 2-fluoro-6-(7-(6-methylpyridin-3-yl)-8-oxo-7,8-dihydro-6H-pyrano[3,2-b:5,4-b']dipyridin-9-yl)benzonitrile To a solution of 9-bromo-7-(6-methylpyridin-3-yl)-6H-pyrano[3,2-b:5,4-b']dipyridin-8(7H)-one (50 mg, 0.135 mmol, 1 equivalent) in DME (4.5 mL) were sequentially added 2-cyano-3-fluorophenylboronic acid pinacol ester (CAS No. 765916-91-4) (50.1 mg, 0.203 mmol, 1.5 equivalents), a 2 M aqueous sodium carbonate solution (101 μL, 0.203 mmol, 1.5 equivalents) and (Ataphos)$_2$PdCl$_2$ (4.78 mg, 6.75 μmol, 0.05 equivalents) at room temperature. The reaction mixture was reacted in a microwave reactor at 105° C. for 2 hours. Subsequently, the reaction mixture was filtered through Celite™, and the filtrate was concentrated under reduced pressure. The resulting residue was purified with silica gel column chromatography (50%-100% ethyl acetate/n-heptane) to afford the title compound (37 mg).

$^1$H-NMR (400 MHz, CDCl$_3$) δ (ppm): 2.68 (s, 3H), 4.74 (d, J=15.6 Hz, 1H), 4.90 (d, J=15.6 Hz, 1H), 7.08-7.14 (m, 1H), 7.16-7.25 (m, 2H), 7.36-7.49 (m, 2H), 7.57-7.69 (m, 2H), 8.25 (dd, J=4.7, 1.6 Hz, 1H), 8.45 (a, J=2.7 Hz, 1H), 8.55 (s, 1H).

MS [M+H]$^+$=411

Example 4

Synthesis of 9-(2-chloro-3-fluorophenyl)-7-(6-methylpyridin-3-yl)-6H-pyrano[3,2-b:5,4-b']dipyridin-8(7H)-one

Example 5

Synthesis of 2-fluoro-6-(7-(2-methoxypyrimidin-5-yl)-8-oxo-7,8-dihydro-6H-pyrano[3,2-b']dipyridin-9-yl)benzonitrile

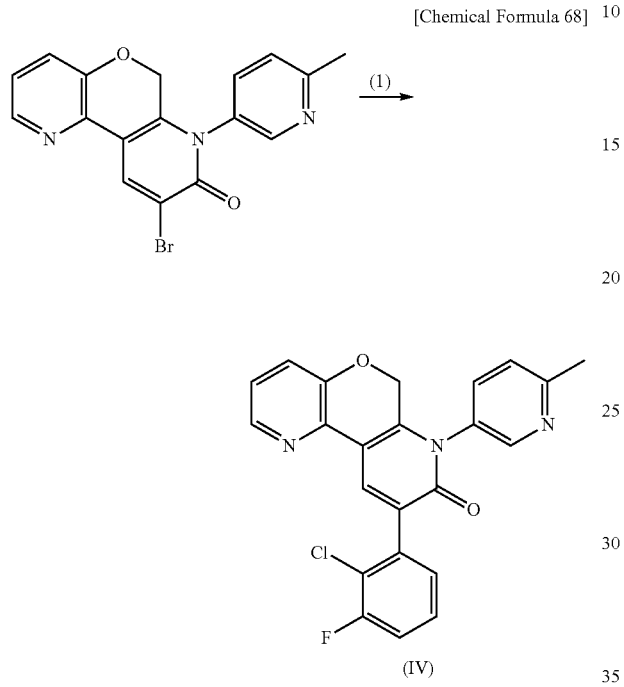

[Chemical Formula 68]

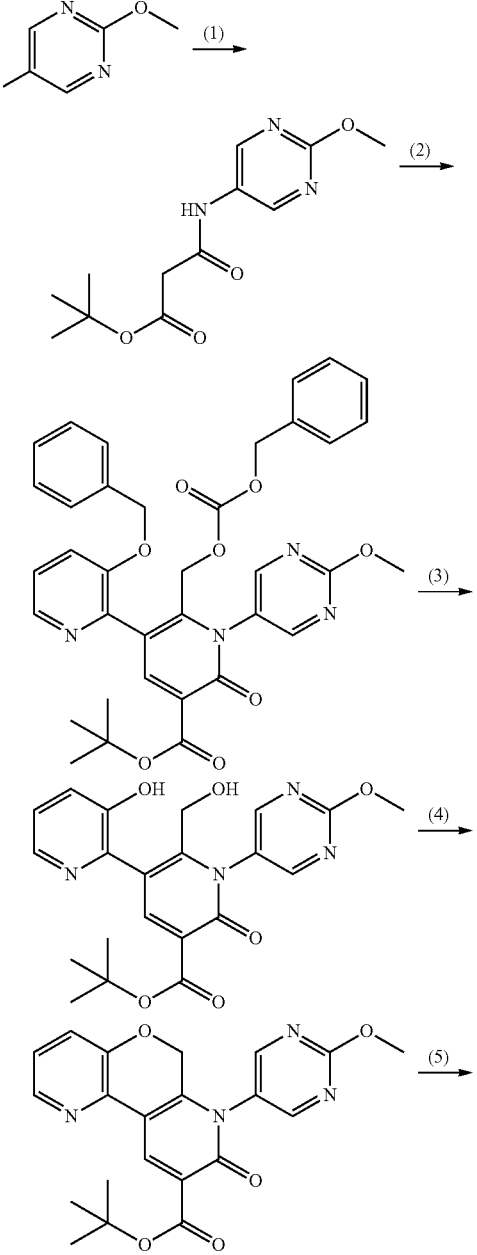

[Chemical Formula 69]

(1) Synthesis of 9-(2-chloro-3-fluorophenyl)-7-(6-methylpyridin-3-yl)-6H-pyrano[3,2-b:5,4-b']dipyridin-8(7H)-one To a solution of 9-bromo-7-(6-methylpyridin-3-yl)-6H-pyrano[3,2-b:5,4-b']dipyridin-8(7H)-one obtained in Example 3-(2) (50 mg, 0.135 mmol, 1 equivalent) in DME (4.5 mL) were sequentially added 2-chloro-3-fluorophenylboronic acid (CAS No. 871329-52-1) (35.3 mg, 0.203 mmol, 1.5 equivalents), a 2 M aqueous sodium carbonate solution (101 μL, 0.203 mmol, 1.5 equivalents) and Pd(PPh$_3$)$_4$ (5.46 mg, 4.73 μmol, 0.035 equivalents) at room temperature. The reaction mixture was reacted in a microwave reactor at 105° C. for 3 hours. Subsequently, the reaction mixture was filtered through Celite™, and the filtrate was concentrated under reduced pressure. The resulting residue was purified with silica gel column chromatography (50%-100% ethyl acetate/n-heptane). To the resulting crude product of the title compound was added diethyl ether, and the precipitate was collected by filtration to afford the solid title compound (21 mg).

$^1$H-NMR (400 MHz, CDCl$_3$) δ (ppm): 2.67 (s, 3H), 4.74 (d, J=15.6 Hz, 1H), 4.89 (d, J=15.6 Hz, 1H), 7.08-7.13 (m, 1H), 7.13-7.20 (m, 2H), 7.22-7.31 (m, 2H), 7.36-7.40 (m, 1H), 7.59-7.64 (m, 1H), 8.22-8.25 (m, 1H), 8.42 (s, 1H), 8.43-8.45 (m, 1H).

MS [M+H]$^+$=420

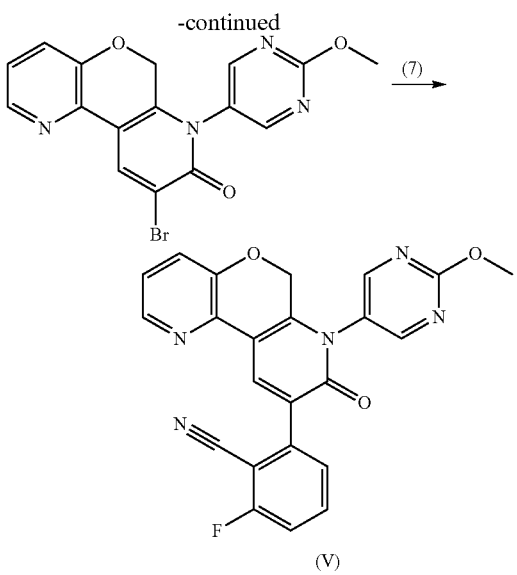

(1) Synthesis of t-butyl 3-((2-methoxypyrimidin-5-yl)amino)-3-oxopropanoate

A solution of 3-(t-butoxy)-3-oxopropionic acid (CAS No. 40052-13-9) (1.41 g, 8.79 mmol, 1.1 equivalents), 2-methoxypyrimidin-5-amine (CAS No. 56621-89-7) (1.00 g, 7.99 mmol, 1.0 equivalents), triethylamine (1.34 mL, 9.59 mmol, 1.2 equivalents) and EDC (1.84 g, 9.59 mmol, 1.2 equivalents) in DCM (20 mL) was heated to reflux for 2 hours. The reaction mixture was cooled down to room temperature. To the reaction mixture was added a saturated aqueous sodium hydrogen carbonate solution, and the mixture was extracted with DCM. The organic layer was concentrated under reduced pressure. The residue was purified with silica gel column chromatography (silica gel, 50%-100% ethyl acetate/n-heptane) to afford the title compound (2.12 g).
$^1$H-NMR (400 MHz, CDCl$_3$) δ (ppm): 1.52 (s, 9H), 3.42 (s, 2H), 4.01 (s, 3H), 8.76 (s, 2H), 9.52 (br. s, 1H).

(2) Synthesis of t-butyl 3-(benzyloxy)-2'-((((benzyloxy)carbonyl)oxy)methyl)-1'-(2-methoxypyrimidin-5-yl)-6'-oxo-1',6'-dihydro-[2,3'-bipyridine]-5'-carboxylate A mixture of t-butyl 3-((2-methoxypyrimidin-5-yl)amino)-3-oxopropanoate (333 mg, 1.25 mmol, 1.2 equivalents), lithium bromide (180 mg, 2.08 mmol, 2.0 equivalents), benzyl (3-(3-(benzyloxy)pyridin-2-yl)-4-methoxy-2-oxobut-3-en-1-yl)carbonate (E/Z mixture) obtained in Production Example 9 (450 mg, 1.04 mmol, 1.0 equivalents), triethylamine (0.506 mL, 3.63 mmol, 3.5 equivalents) and propionitrile (3.00 mL) was stirred at room temperature for 10 minutes. The reaction mixture was directly purified with silica gel column chromatography (silica gel, 40%-100% ethyl acetate/n-heptane) to afford the title compound (430 mg).
MS [M+H]$^+$=651

(3) Synthesis of t-butyl 3-hydroxy-2'-(hydroxymethyl)-1'-(2-methoxypyrimidin-5-yl)-6'-oxo-1',6'-dihydro-[2,3'-bipyridine]-5'-carboxylate A mixture of t-butyl 3-(benzyloxy)-2'-((((benzyloxy)carbonyl)oxy)methyl)-1'-(2-methoxypyrimidin-5-yl)-6'-oxo-1', 6'-dihydro-[2,3'-bipyridine]-5'-carboxylate (430 mg, 0.661 mmol, 1.0 equivalents), 10% palladium on carbon (water content, 53.9%) (70.3 mg, 0.03 mmol, 0.046 equivalents), THF (2.00 mL) and methanol (5.00 mL) was stirred at room temperature under a hydrogen atmosphere for 40 minutes. The reaction mixture was filtered through Celite™, and the residue was washed with ethyl acetate. The resulting filtrate was concentrated under reduced pressure. The residue was purified with silica gel column chromatography (silica gel, 0%-20% methanol/ethyl acetate) to afford the title compound (280 mg).
MS [M+H]$^+$=427

(4) Synthesis of t-butyl 7-(2-methoxypyrimidin-5-yl)-8-oxo-7,8-dihydro-6H-pyrano[3,2-b:5,4-b'] dipyridine-9-carboxylate To a mixture of t-butyl 3-hydroxy-2'-(hydroxymethyl)-1'-(2-methoxypyrimidin-5-yl)-6'-oxo-1',6'-dihydro-[2,3'-bipyridine]-5'-carboxylate (280 mg, 0.657 mmol, 1.0 equivalents), triphenylphosphine (241 mg, 0.919 mmol, 1.4 equivalents) and THF (3.00 mL) was added a solution of DMEAD (215 mg, 0.919 mmol, 1.4 equivalents) in THF (1.00 mL) at 0° C. After the progress of the reaction mixture was confirmed, the reaction mixture was concentrated under reduced pressure to about one half of the original solution volume. The residue was purified with silica gel column chromatography (silica gel, 40%-100% ethyl acetate/n-heptane) to afford the title compound (210 mg).
MS m/z=410

(5) Synthesis of 7-(2-methoxypyrimidin-5-yl)-6H-pyrano[3,2-b:5,4-b']dipyridin-8(7H)-one To t-butyl 7-(2-methoxypyrimidin-5-yl)-8-oxo-7,8-dihydro-6H-pyrano[3,2-b:5,4-b']dipyridine-9-carboxylate (210 mg, 0.514 mmol, 1.0 equivalents) was added TFA (3.00 mL), and the reaction mixture was concentrated under reduced pressure. To the resulting residue were added DMSO (3.00 mL) and lithium acetate dihydrate (262 mg, 2.57 mmol, 5.0 equivalents), and the reaction mixture was stirred at 120° C. for 30 minutes. To the reaction mixture was added a 10% aqueous sodium chloride solution, and the mixture was extracted with ethyl acetate. The organic layer was dried over magnesium sulfate, filtered, and then concentrated under reduced pressure. The resulting residue was purified with silica gel column chromatography (silica gel, 0%-20% methanol/ethyl acetate) to afford the title compound (110 mg).
MS [M+H]$^+$=309

(6) Synthesis of 9-bromo-7-(2-methoxypyrimidin-5-yl)-6H-pyrano[3,2-b:5,4-b']dipyridin-8(7H)-one A mixture of 7-(2-methoxypyrimidin-5-yl)-6H-pyrano[3, 2-b:5,4-b']dipyridin-8(7H)-one (20.0 mg, 0.065 mmol, 1.0 equivalents), NBS (17.3 mg, 0.097 mmol, 1.5 equivalents) and DMF (2.00 mL) was stirred at 50° C. for 30 minutes. The reaction mixture was concentrated under reduced pressure, and the resulting residue was purified with silica gel, column chromatography (silica gel, 100% ethyl acetate) to afford the title compound (11.0 mg).
MS [M+H]$^+$=387

(7) Synthesis of 2-fluoro-6-(7-(2-methoxypyrimidin-5-yl)-8-oxo-7,8-dihydro-6H-pyrano[3,2-b:5,4-b'] dipyridin-9-yl)benzonitrile A mixture of 9-bromo-7-(2-methoxypyrimidin-5-yl)-6H-pyrano[3,2-b:5,4-b']dipyridin-8(7H)-one (11.0 mg, 0.028 mmol, 1.0 equivalents), 2-cyano-3-fluorophenylboronic acid pinacol ester (CAS No. 765916-91-4) (10.5 mg, 0.043 mmol, 1.5 equivalents), (Ataphos)$_2$PdCl$_2$ (2.01 mg, 2.84 μmol, 0.1 equivalents), potassium fluoride (4.95 mg, 0.085 mmol, 3.0 equivalents), 1,4-dioxane (0.8 mL) and water (0.4 mL) was reacted in a microwave reactor at 140° C. for 10 minutes. The reaction mixture was directly purified with silica gel column chromatography (silica gel, 80%-100% ethyl acetate/n-heptane). The resulting crude product was purified again with silica gel column chromatography (NH silica gel, 50%-80% ethyl acetate/n-heptane) to afford the title compound (6.0 mg).

$^1$H-NMR (400 MHz, CDCl$_3$) δ (ppm): 4.12 (s, 3H), 4.88 (s, 2H), 7.11-7.17 (m, 1H), 7.17-7.26 (m, 2H), 7.44 (d, J=7.0 Hz, 1H), 7.64 (td, J=8.1, 5.7 Hz, 1H), 8.26 (dd, J=4.4, 1.5 Hz, 1H), 8.54 (s, 2H), 8.57 (s, 1H).

MS [M+H]$^+$=428

Example 6

Synthesis of 7-(pyridin-3-yl)-9-(2,3,5,6-tetrafluorophenyl)-6H-pyrano[3,2-b:5,4-b']dipyridin-8(7H)-one

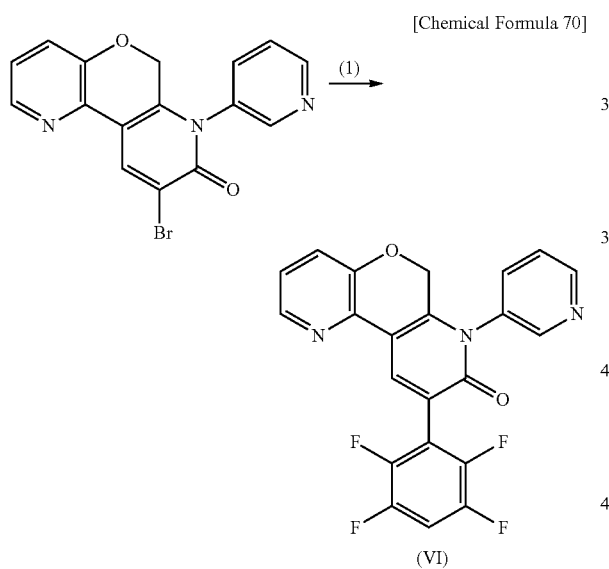

[Chemical Formula 70]

(1) Synthesis of 7-(pyridin-3-yl)-9-(2,3,5,6-tetrafluorophenyl)-6H-pyrano[3,2-b:5,4-b']dipyridin-8(7H)-one A mixture of 9-bromo-7-(pyridin-3-yl)-6H-pyrano[3,2-b:5,4-b']dipyridin-8(7H)-one obtained in Production Example 2 (40 mg, 0.112 mmol, 1 equivalent), tributyl(2,3,5,6-tetrafluorophenyl)stannane obtained in Production Example 6 (74.0 mg, 0.168 mmol, 1.5 equivalents), (Ataphos)$_2$PdCl$_2$ (3.98 mg, 5.62 μmol, 0.05 equivalents), copper(I) iodide (2.14 mg, 0.011 mmol, 0.1 equivalents) and 1,4-dioxane (1.5 mL) was reacted in a microwave reactor at 150° C. for 5 hours. The reaction mixture was directly purified with silica gel column chromatography (NH silica gel on silica gel, 5%-95% ethyl acetate/n-heptane). The resulting crude product was triturated with a mixed solution of diethyl ether-n-heptane (1:5), and the precipitate was collected by filtration. The resulting solid was washed with diethyl ether and n-heptane to afford the title compound (24.4 mg).

$^1$H-NMR (400 MHz, CDCl$_3$) δ (ppm): 4.74 (d, J=15.6 Hz, 1H), 4.88 (d, J=15.6 Hz, 1H), 7.05-7.16 (m, 2H), 7.17-7.21 (m, 1H), 7.53-7.59 (m, 1H), 7.73-7.79 (m, 1H), 8.26 (dd, J=4.6, 1.5 Hz, 1H), 8.52 (s, 1H), 8.61 (d, J=2.4 Hz, 1H), 8.81 (dd, J=4.8, 1.5 Hz, 1H).

MS [M+Na]$^+$=448

Example 7

Synthesis of 3-(8-oxo-7-(thiophen-3-yl)-7,8-dihydro-6H-pyrano[3,2-b:5,4-b']dipyridin-9-yl)picolinonitrile

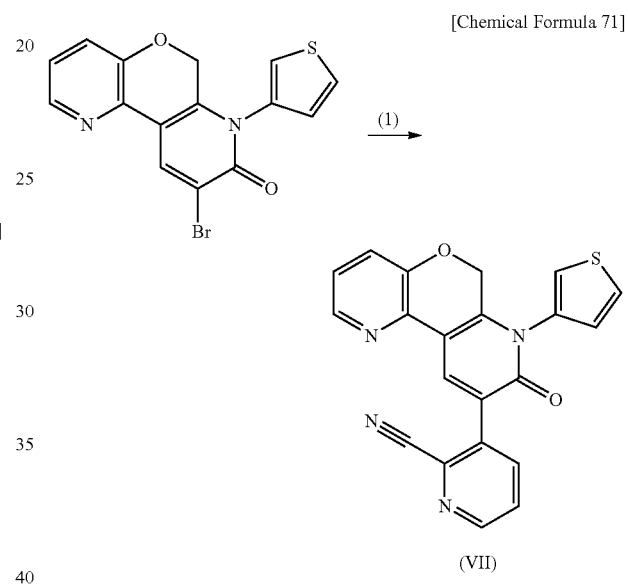

[Chemical Formula 71]

(1) Synthesis of 3-(8-oxo-7-(thiophen-3-yl)-7,8-dihydro-6H-pyrano[3,2-b:5,4-b']dipyridin-9-yl)picolinonitrile A mixture of 9-bromo-7-(thiophen-3-yl)-6H-pyrano[3,2-b:5,4-b']dipyridin-8(7H)-one obtained in Production Example 3 (40 mg, 0.111 mmol, 1 equivalent), 2-cyanopyridine-3-boronic acid neopentyl glycol ester (CAS No. 868944-75-6) (35.9 mg, 0.166 mmol, 1.5 equivalents), (Ataphos)$_2$PdCl$_2$ (3.92 mg, 5.54 μmol, 0.05 equivalents), potassium fluoride (19.3 mg, 0.332 mmol, 3 equivalents), 1,4-dioxane (1 mL) and water (0.3 mL) was reacted in a microwave reactor at 120° C. for 3 hours. The reaction mixture was directly purified with silica gel column chromatography (NH silica gel on silica gel, 5%-100% ethyl acetate/n-heptane). The resulting crude product was purified again with silica gel column chromatography (NH silica gel, 5%-95% ethyl acetate/n-heptane) to afford the title compound (23.4 mg).

$^1$H-NMR (400 MHz, CDCl$_3$) δ (ppm): 4.88 (br. s, 2H), 7.09-7.15 (m, 2H), 7.16-7.20 (m, 1H), 7.37-7.40 (m, 1H), 7.52-7.59 (m, 2H), 8.05-8.10 (m, 1H), 8.23-8.27 (m, 1H), 8.62 (s, 1H), 8.67-8.72 (m, 1H).

MS [M+Na]$^+$=407

Example 8

Synthesis of 3-(8-oxo-7-(thiophen-3-yl)-7,8-dihydro-6H-pyrano[3,2-b:5,4-b']dipyridin-9-yl)pyrazine-2-carbonitrile

[Chemical Formula 72]

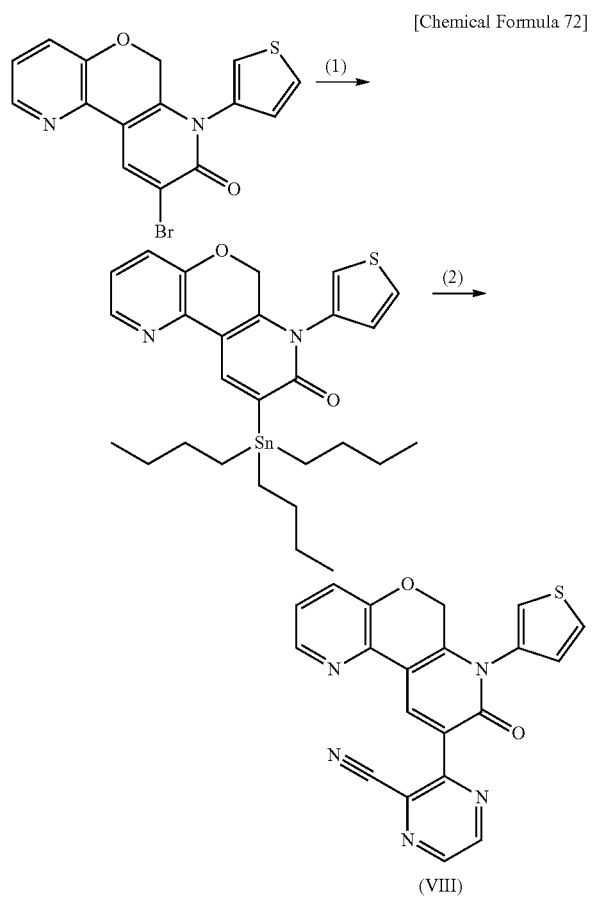

(1) Synthesis of 7-(thiophen-3-yl)-9-(tributylstannyl)-6H-pyrano[3,2-b:5,4-b']dipyridin-8(7H)-one A mixture of 9-bromo-7-(thiophen-3-yl)-6H-pyrano[3,2-b:5,4-b']dipyridin-8(7H)-one obtained in Production Example 3 (34.8 mg, 0.096 mmol, 1 equivalent), hexa-n-butylditin (0.058 ml, 0.116 mmol, 1.2 equivalents), Pd(PPh$_3$)$_4$ (5.57 mg, 4.82 μmol, 0.05 equivalents) and 1,4-dioxane (1 mL) was reacted in a microwave reactor at 140° C. for 6 hours. The reaction mixture was allowed to return to room temperature, and then directly purified with silica gel column chromatography (NH silica gel, 0%-30% ethyl acetate/n-heptane) to afford the title compound (38.3 mg).
MS [M+H]$^+$=573

(2) Synthesis of 3-(8-oxo-7-(thiophen-3-yl)-7,8-dihydro-6H-pyrano[3,2-b:5,4-b']dipyridin-9-yl)pyrazine-2-carbonitrile A mixture of 7-(thiophen-3-yl)-9-(tributylstannyl)-6H-pyrano[3,2-b:5,4-b']dipyridin-8(7H)-one (38.3 mg, 0.067 mmol, 1 equivalent), 3-bromopyrazine-2-carbonitrile (CAS No. 1250022-24-2) (18.5 mg, 0.101 mmol, 1.5 equivalents), copper(I) iodide (1.28 mg, 6.70 μmol, 0.1 equivalents), Pd(PPh$_3$)$_4$ (3.87 mg, 3.35 μmol, 0.05 equivalents) and 1,4-dioxane (1 mL) was reacted in a microwave reactor at 150° C. for 2.5 hours. The reaction mixture was allowed to return to room temperature, and then directly purified with silica gel column chromatography (NH silica gel on silica gel, 5%-95% ethyl acetate/n-heptane). The resulting crude product was triturated with a mixed solution of ethanol-n-heptane (1:1), and the precipitate was collected by filtration. The resulting solid was washed with n-heptane to afford the title compound (14.2 mg).
$^1$H-NMR (400 MHz, CDCl$_3$) δ (ppm): 4.91 (br. s, 2H), 7.10-7.15 (m, 2H), 7.16-7.21 (m, 1H), 7.38-7.42 (m, 1H), 7.53-7.59 (m, 1H), 8.23-8.27 (m, 1H), 8.64-8.68 (m, 1H), 8.79 (s, 1H), 8.82-8.86 (m, 1H).
MS [M+Na]$^+$=408

Example 9

Synthesis of 9-(2-fluorophenyl)-7-phenyl-6H-pyrano[3,2-b:5,4-b']dipyridin-8(7H)-one

[Chemical Formula 73]

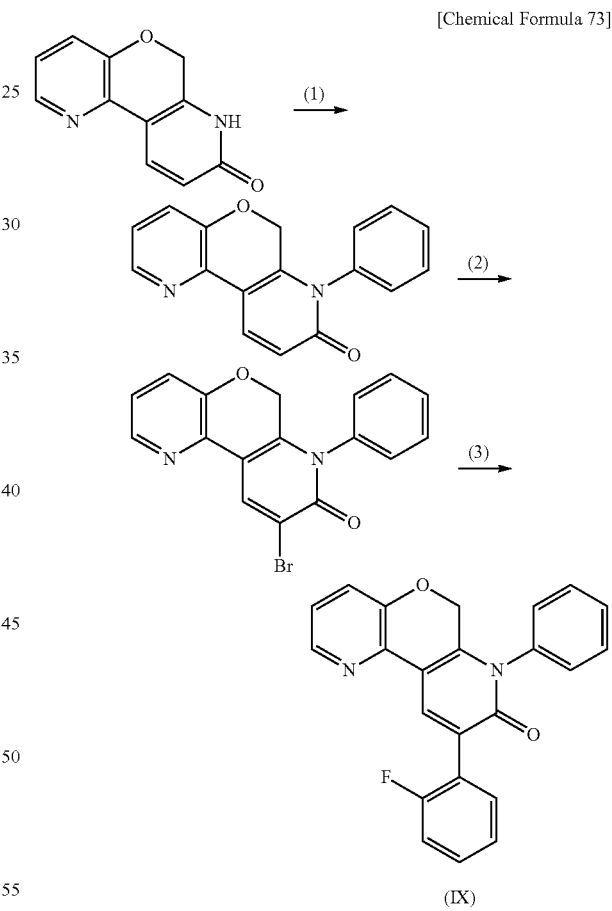

(1) Synthesis of 7-phenyl-6H-pyrano[3,2-b:5,4-b']dipyridin-8(7H)-one

A mixture of 6H-pyrano[3,2-b:5,4-b']dipyridin-8(7H)-one obtained in Production Example 1 (5 g, 25.0 mmol, 1 equivalent), phenylboronic acid (CAS No. 98-80-6) (6.09 g, 50.0 mmol, 2 equivalents), silver carbonate (8.26 g, 30.0 mmol, 1.2 equivalents), copper(I) iodide (2.85 g, 15.0 mmol, 0.6 equivalents), pyridine (12.1 mL, 150 mmol, 6 equivalents) and DMF (150 mL) was stirred at 70° C. overnight.

The reaction mixture was concentrated under reduced pressure, and to the residue were added a 28% aqueous ammonia solution and chloroform. The mixture was stirred at room temperature for 30 minutes, and then filtered. The filtrate was extracted with chloroform. To the organic layer was added silica gel, and the mixture was concentrated under reduced pressure. The residue was purified with silica gel column chromatography (NH silica gel, 10%-100% ethyl acetate/n-heptane) to afford the title compound (3.27 g).

$^1$H-NMR (400 MHz, CDCl$_3$) δ (ppm): 4.70 (s, 2H), 6.74-6.79 (m, 1H), 7.05-7.10 (m, 1H), 7.10-7.14 (m, 1H), 7.24-7.28 (m, 2H), 7.52-7.60 (m, 3H), 8.22-8.25 (m, 1H), 8.29-8.34 (m, 1H),

MS [M+H]$^+$=277

(2) Synthesis of 9-bromo-7-phenyl-6H-pyrano[3,2-b:5,4-b']dipyridin-8(7H)-one

A mixture of 7-phenyl-6H-pyrano[3,2-b:5,4-b']dipyridin-8(7H)-one (3.27 g, 11.8 mmol, 1 equivalent), NBS (2.32 g, 13.0 mmol, 1.1 equivalents) and DMF (35 mL) was stirred at room temperature for 2 hours. To the reaction mixture was added ice water. The mixture was stirred at 0° C. for 2 hours, and then the precipitate was collected by filtration. The resulting solid was washed with water and n-heptane to afford the title compound (3.00 g).

$^1$H-NMR (400 MHz, CDCl$_3$) δ (ppm): 4.67 (s, 2H), 7.07-7.12 (m, 1H), 7.12-7.16 (m, 1H), 7.22-7.28 (m, 2H), 7.51-7.61 (m, 3H), 8.22-8.26 (m, 1H), 8.75 (s, 1H).

MS [M+H]$^+$=355

(3) Synthesis of 9-(2-fluorophenyl)-7-phenyl-6H-pyrano[3,2-b:5,4-b']dipyridin-8(7H)-one A mixture of 9-bromo-7-phenyl-6H-pyrano[3,2-b:5,4-b'] dipyridin-8(7H)-one (40 mg, 0.113 mmol, 1 equivalent), 2-fluorophenylboronic acid (CAS No. 1993-03-9) (23.6 mg, 0.169 mmol, 1.5 equivalents), tripotassium phosphate N-hydrate (64.8 mg), Pd(PPh$_3$)$_4$ (6.51 mg, 5.63 μmol, 0.05 equivalents), 1,4-dioxane (1 mL) and water (0.3 mL) was reacted in a microwave reactor at 130° C. for 70 minutes. The reaction mixture was directly purified with silica gel column chromatography (silica gel, 10%-70% ethyl acetaten-heptane) to afford the title compound (31.5 mg).

$^1$H-NMR (400 MHz, CDCl$_3$) δ (ppm): 4.77 (s, 2H), 7.06-7.20 (m, 4H), 7.29-7.36 (m, 3H), 7.49-7.64 (m, 4H), 8.24 (dd, J=4.7, 1.6 Hz, 1H), 8.49 (d, J=1.2 Hz, 1H).

MS [M+H]$^+$=371

Example 10

Synthesis of 2-(7-(4-fluorophenyl)-8-oxo-7,8-dihydro-6H-pyrano[3,2-b:5,4-b']dipyridin-9-yl)benzonitrile

[Chemical Formula 74]

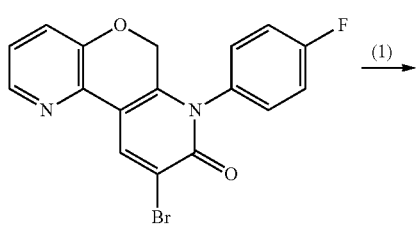

(1)

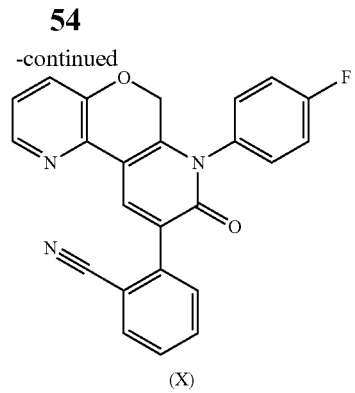

(X)

(1) Synthesis of 2-(7-(4-fluorophenyl)-8-oxo-7,8-dihydro-6H-pyrano[3,2-b:5,4-b']dipyridin-9-yl)benzonitrile A mixture of 9-bromo-7-(4-fluorophenyl)-6H-pyrano[3,2-b:5,4-b']dipyridin-8(7H)-one obtained in Production Example 4 (50 mg, 0.134 mmol, 1 equivalent), 2-(1,3,2-dioxaborinan-2-yl)benzonitrile (CAS No. 172732-52-4) (37.6 mg, 0.201 mmol, 1.5 equivalents), (Ataphos)$_2$PdCl$_2$ (4.74 mg, 6.70 μmol, 0.05 equivalents), triethylamine (0.075 mL, 0.536 mmol, 4 equivalents), 1,4-dioxane (1 mL) and water (0.3 mL) was reacted in a microwave reactor at 130° C. for 3 hours. The reaction mixture was directly purified with silica gel column chromatography (NH silica gel, 5%-60% ethyl acetate/n-heptane) to afford the title compound (19.9 mg).

$^1$H-NMR (400 MHz, CDCl$_3$) δ (ppm): 4.80 (s, 2H), 7.08-7.13 (m, 1H), 7.14-7.18 (m, 1H), 7.24-7.30 (m, 2H), 7.30-7.36 (m, 2H), 7.43-7.48 (m, 1H), 7.60-7.68 (m, 2H), 7.73-7.77 (m, 1H), 8.24 (dd, J=4.7, 1.4 Hz, 1H), 8.53 (s, 1H).

MS [M+Na]$^+$=418

Example 11

Synthesis of 3-(7-(4-fluorophenyl)-8-oxo-7,8-dihydro-6H-pyrano[3,2-b:5,4-b']dipyridin-9-yl)picolinonitrile

[Chemical Formula 75]

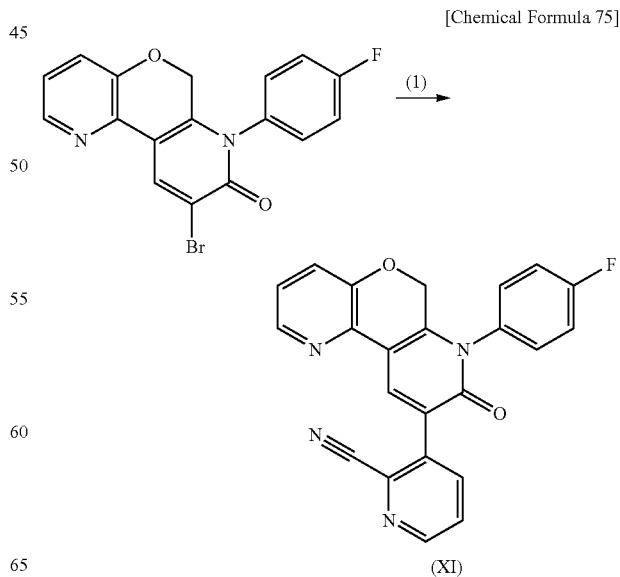

(XI)

(1) Synthesis of 3-(7-(4-fluorophenyl)-8-oxo-7,8-dihydro-6H-pyrano[3,2-b:5,4-b']dipyridin-9-yl)picolinonitrile A mixture of 9-bromo-7-(4-fluorophenyl)-6H-pyrano[3,2-b:5,4-b']dipyridin-8(7H)-one obtained in Production Example 4 (800 mg, 2.14 mmol, 1 equivalent), 2-cyanopyridine-3-boronic acid neopentyl glycol ester (CAS No. 868944-75-6) (648 mg, 3.00 mmol, 1.4 equivalents), (Ataphos)$_2$PdCl$_2$ (76 mg, 0.107 mmol, 0.05 equivalents), potassium fluoride (374 mg, 6.43 mmol, 3 equivalents), 1,4-dioxane (16 mL) and water (4 mL) was reacted in a microwave reactor at 120° C. for 2.5 hours. The reaction mixture was directly purified with silica gel column chromatography (silica gel, 5%-90% ethyl acetate/n-heptane). The resulting crude product was applied to silica gel pad (NH silica gel), and eluted with ethyl acetate. The resulting solution was concentrated under reduced pressure. The residue was dissolved in DCM. The solution was filtered, and the filtrate was concentrated under reduced pressure. The residue was triturated with a mixed solution of IPA and n-heptane (1:1), and the precipitate was collected by filtration. The resulting solid was washed with n-heptane, and suspended in IPA, and the precipitate was collected by filtration. The resulting solid was washed with IPA to afford the title compound (493 mg).

$^1$H-NMR (400 MHz, CDCl$_3$) δ (ppm): 4.81 (s, 2H), 7.09-7.15 (m, 1H), 7.15-7.20 (m, 1H), 7.27-7.36 (m, 4H), 7.52-7.58 (m, 1H), 8.03-8.08 (m, 1H), 8.23-8.27 (m, 1H), 8.64 (s, 1H), 8.67-8.71 (m, 1H).

MS [M+H]$^+$=397

Example 12

Synthesis of 3-(7-(2-fluorophenyl)-8-oxo-7,8-dihydro-6H-pyrano[3,2-b:5,4-b']dipyridin-9-yl)picolinonitrile

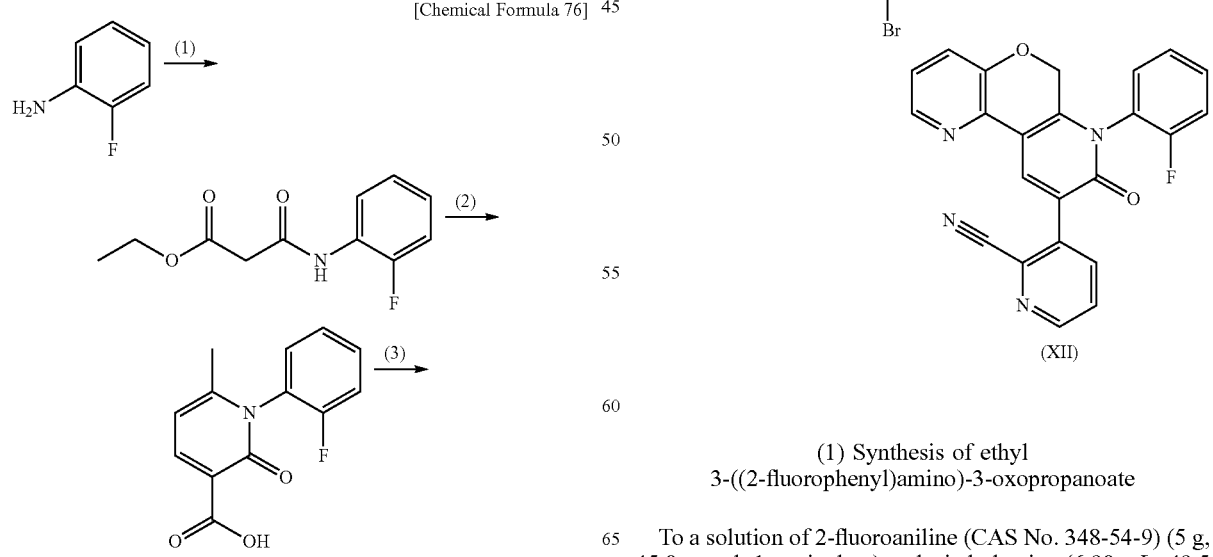

(1) Synthesis of ethyl 3-((2-fluorophenyl)amino)-3-oxopropanoate

To a solution of 2-fluoroaniline (CAS No. 348-54-9) (5 g, 45.0 mmol, 1 equivalent) and triethylamine (6.90 mL, 49.5 mmol, 1.1 equivalents) in THF (100 mL) was added ethyl malonyl chloride (CAS No. 36239-09-5) (6.05 mL, 47.2 mmol, 1.05 equivalents) at 0° C., and the mixture was stirred at the same temperature for 1 hour. To the reaction mixture was added 1 M hydrochloric acid, and the mixture was extracted with ethyl acetate. The organic layer was concentrated under reduced pressure, and the residue was purified with silica gel column chromatography (silica gel, 5%-45% ethyl acetate/n-heptane) to afford the title compound (8.64 g).

$^1$H-NMR (400 MHz, CDCl$_3$) δ (ppm): 1.33 (t, J=7.2 Hz, 3H), 3.51 (s, 2H), 4.28 (q, J=7.2 Hz, 2H), 7.02-7.18 (m, 3H), 8.24-8.36 (m, 1H), 9.50 (br. s, 1H).

MS [M+H]$^+$=226

(2) Synthesis of 1-(2-fluorophenyl)-6-methyl-2-oxo-1,2-dihydropyridine-3-carboxylic acid A solution of ethyl 3-((2-fluorophenyl)amino)-3-oxopropanoate (8.64 g, 38.4 mmol, 1 equivalent), acetylacetaldehyde dimethyl acetal (CAS No. 5436-21-5) (6.08 mL, 46.0 mmol, 1.2 equivalents) and sodium ethoxide (20% solution in ethanol, 48.9 mL, 127 mmol, 3.3 equivalents) in ethanol (105 mL) was stirred at 80° C. for 15 hours. The reaction mixture was allowed to return to room temperature, and then concentrated under reduced pressure. To the residue was added 5 M hydrochloric acid, and the mixture was extracted with DCM. The organic layer was concentrated under reduced pressure. The residue was triturated with a mixed solution of ethyl acetate and n-heptane, and the precipitate was collected by filtration. The resulting solid was washed with n-heptane to afford the title compound (8.02 g).

$^1$H-NMR (400 MHz, CDCl$_3$) δ (ppm): 2.18 (s, 3H), 6.54-6.59 (m, 1H), 7.27-7.32 (m, 1H), 7.33-7.43 (m, 2H), 7.55-7.63 (m, 1H), 8.54 (d, J=7.4 Hz, 1H), 13.74 (s, 1H),

MS [M+H]$^+$=248

(3) Synthesis of 5-bromo-1-(2-fluorophenyl)-6-methyl-2-oxo-1,2-dihydropyridine-3-carboxylic acid A solution of 1-(2-fluorophenyl)-6-methyl-2-oxo-1,2-dihydropyridine-3-carboxylic acid (8.02 g, 32.4 mmol, 1 equivalent) and NBS (6.35 g, 35.7 mmol, 1.1 equivalents) in DMF (80 mL) was stirred at room temperature for 1 hour. To the reaction mixture was added ice water, and the mixture was stirred at room temperature for 30 minutes, and then the precipitate was collected by filtration. The resulting solid was washed with water and n-heptane to afford the title compound (9.32 g).

$^1$H-NMR (400 MHz, CDCl$_3$) δ (ppm): 2.33 (s, 3H), 7.23-7.29 (m, 1H), 7.34-7.44 (m, 2H), 7.56-7.64 (m, 1H), 8.71 (s, 1H), 13.53 (s, 1H).

MS [M+H]$^+$=328

(4) Synthesis of 5-bromo-1-(2-fluorophenyl)-6-methylpyridin-2(1H)-one

A mixture of 5-bromo-1-(2-fluorophenyl)-6-methyl-2-oxo-1,2-dihydropyridine-3-carboxylic acid (5 g, 15.3 mmol, 1 equivalent), lithium hydroxide (808 mg, 33.7 mmol, 2.2 equivalents), diglyme (100 mL) and water (10 mL) was stirred at 150° C. for 10 hours. During the reaction, water was distilled off from the reaction using a Dean-Stark apparatus. The reaction mixture was allowed to return to room temperature, and then concentrated under reduced pressure. The residue was triturated with water, and the precipitate was collected by filtration. The resulting solid was washed with water to afford the title compound (2.70 g).

$^1$H-NMR (400 MHz, CDCl$_3$) δ (ppm): 2.15 (s, 3H), 6.44-6.51 (m, 1H), 7.19-7.35 (m, 3H), 7.44-7.52 (m, 2H).

MS [M+H]$^+$=282

(5) Synthesis of 1'-(2-fluorophenyl)-3-(methoxymethoxy)-2'-methyl-[2,3'-bipyridin]-6'(1'H)-one A mixture of 5-bromo-1-(2-fluorophenyl)-6-methylpyridin-2(1H)-one (1 g, 3.55 mmol, 1 equivalent), 3-(methoxymethoxy)-2-(tributylstannyl)pyridine obtained in Production Example 7 (1.55 mL, 3.90 mmol, 1.1 equivalents), Pd(PPh$_3$)$_4$ (205 mg, 0.177 mmol, 0.05 equivalents) and 1,4-dioxane (20 mL) was reacted in a microwave reactor at 150° C. for 7 hours. The reaction mixture was directly purified with silica gel column chromatography (NH silica gel on silica gel, 10%400% ethyl acetate/n-heptane, 5% methanol/ethyl acetate) to afford the title compound (523 mg).

$^1$H-NMR (400 MHz, CDCl$_3$) δ (ppm): 1.89 (s, 3H), 3.44 (s, 3H), 5.18 (s, 2H), 6.59-6.66 (m, 1H), 7.24-7.34 (m, 4H), 7.42-7.50 (m, 2H), 7.55 (dd, J=8.4, 1.4 Hz, 1H), 8.35 (dd, J=4.7, 1.4 Hz, 1H).

MS [M+H]$^+$=341

(6) Synthesis of 5'-bromo-1'-(2-fluorophenyl)-3-(methoxymethoxy)-2'-methyl-[2,3'-bipyridin]-6'(1'H)-one A mixture of 1'-(2-fluorophenyl)-3-(methoxymethoxy)-2'-methyl-[2,3'-bipyridin]-6'(1'H)-one (523 mg, 1.54 mmol, 1 equivalent), NBS (301 trig, 1.69 mmol, 1.1 equivalents) and acetonitrile (10 mL) was stirred at room temperature for 12 hours. To the reaction mixture was added a saturated aqueous sodium hydrogen carbonate solution, and the mixture was concentrated under reduced pressure. The residue was extracted with DCM, and the organic layer was concentrated under reduced pressure. The residue was purified with silica gel column chromatography (silica gel, 10%-90% ethyl acetate/n-heptane) to afford the title compound (586 mg).

$^1$H-NMR (400 MHz, CDCl$_3$) δ (ppm): 1.87 (s, 3H), 3.46 (s, 3H), 5.20 (s, 2H), 7.24-7.35 (m, 4H), 7.44-7.51 (m, 1H), 7.56 (dd, J=8.4, 1.4 Hz, 1H), 7.89 (s, 1H), 8.35 (dd, J=4.7, 1.4 Hz, 1H).

MS [M+H]$^+$=419

(7) Synthesis of 9-bromo-7-(2-fluorophenyl)-6H-pyrano[3,2-b:5,4-b']dipyridin-8(7H)-one A solution of 5'-bromo-1'-(2-fluorophenyl)-3-(methoxymethoxy)-2'-methyl-[2,3'-bipyridin]-6'(1'H)-one (586 mg, 1.40 mmol, 1 equivalent), NBS (269 mg, 1.51 mmol, 1.08 equivalents) and AIBN (11.5 mg, 0.07 mmol, 0.05 equivalents) in carbon tetrachloride (12 mL) was heated to reflux for 2 hours. The reaction mixture was allowed to return to room temperature, and then concentrated under reduced pressure. The residue was dissolved in THF (13.4 mL). To the solution was added a 48% aqueous hydrobromic acid solution (1.58 mL, 14.0 mmol, 10 equivalents). The reaction mixture was stirred at 60° C. for 30 minutes. The reaction mixture was allowed to return to room temperature, and then a saturated aqueous sodium hydrogen carbonate solution (5 mL) was added. The mixture was stirred at room temperature for 1 hour, and then concentrated under reduced pressure. The residue was extracted with DCM, and the organic layer was concentrated under reduced pressure. The residue was purified with silica gel column chromatography (silica gel, 10%-70% ethyl acetatetn-heptane) to afford the title compound (222 mg).

$^1$H-NMR (400 MHz, CDCl$_3$) δ (ppm): 4.69-4.79 (m, 2H), 7.08-7.13 (m, 1H), 7.13-7.17 (m, 1H), 7.28-7.38 (m, 3H), 7.51-7.59 (m, 1H), 8.25 (dd, J=4.5, 1.6 Hz, 1H), 8.76 (s, 1H).

MS [M+H]$^+$=373

(8) Synthesis of 3-(7-(2-fluorophenyl)-8-oxo-7,8-dihydro-6H-pyrano[3,2-b:5,4-b']dipyridin-9-yl)picolinonitrile A mixture of 9-bromo-7-(2-fluorophenyl)-6H-pyrano[3,2-b:5,4-b']dipyridin-8(7H)-one (70 mg, 0.188 mmol, 1 equivalent), 2-cyanopyridine-3-boronic acid neopentyl glycol ester (CAS No. 868944-75-6) (60.8 mg, 0.281 mmol, 1.5 equivalents), (Ataphos)$_2$PdCl$_2$ (6.64 mg, 9.38 μmol, 0.05 equivalents), triethylamine (0.078 mL, 0.563 mmol, 3 equivalents), 1,4-dioxane (1.5 mL) and water (0.3 mL) was reacted in a microwave reactor at 140° C. for 5 hours. The reaction mixture was allowed to return to room temperature, and then directly purified with silica gel column chromatography (silica gel, 10%-80% ethyl acetate/n-heptane). The resulting crude product was triturated with a mixed solution of MTBE, ethyl acetate and n-heptane (1:1:5), and the precipitate was collected by filtration. The resulting solid was washed with n-heptane to afford the title compound (23.9 mg).

$^1$H-NMR (400 MHz, CDCl$_3$) δ (ppm): 4.81-4.91 (m, 2H), 7.09-7.14 (m, 1H), 7.15-7.20 (m, 1H), 7.31-7.43 (m, 3H), 7.51-7.60 (m, 2H), 8.09 (dd, J=8.1, 1.7 Hz, 1H), 8.25 (dd, J=4.6, 1.5 Hz, 1H), 8.67 (s, 1H), 8.69 (dd, J=4.7, 1.8 Hz, 1H).

MS [M+Na]$^+$=419

Example 13

Synthesis of 3-(3-fluoro-8-oxo-7-phenyl-7,8-dihydro-6H-pyrano[3,2-b:5,4-b']dipyridin-9-yl)picolinonitrile

[Chemical Formula 77]

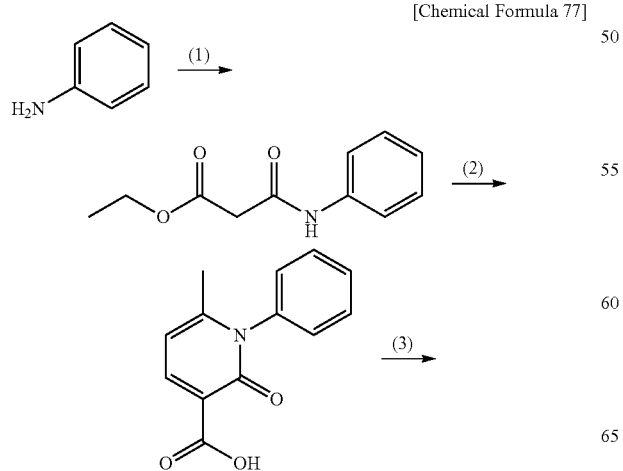

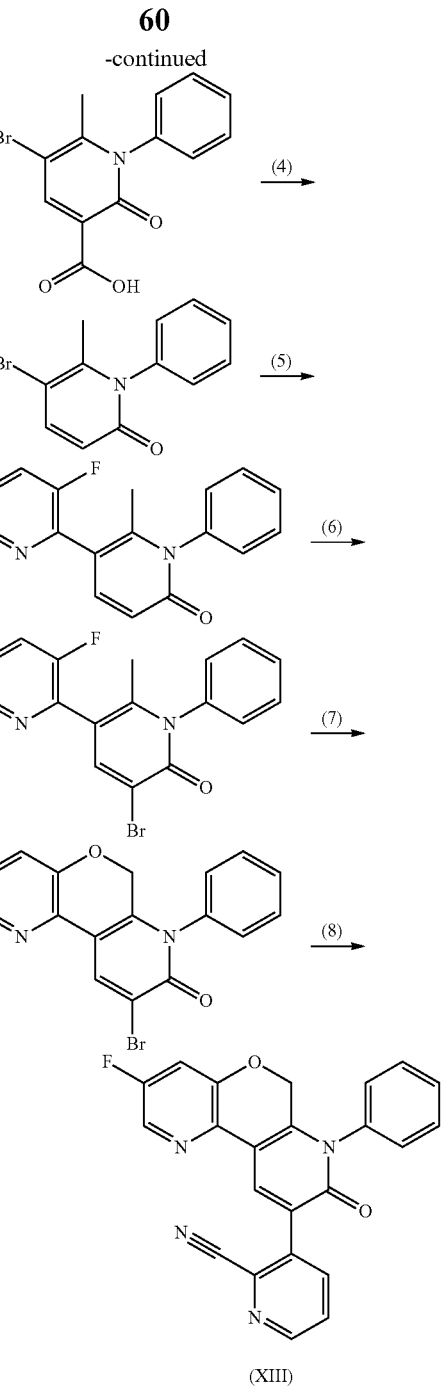

(1) Synthesis of ethyl 3-oxo-3-(phenylamino)propanoate

To a solution of aniline (CAS No. 62-53-3) (2 mL, 21.9 mmol, 1 equivalent) and triethylamine (3.37 mL, 24.1 mmol, 1.1 equivalents) in THF (40 mL) was added ethyl malonyl chloride (CAS No. 36239-09-5) (3.09 mL, 24.1 mmol, 1.1 equivalents) at 0° C., and the mixture was stirred at the same temperature for 2 hours. To the reaction mixture was added 1 M hydrochloric acid, and the mixture was extracted with ethyl acetate. The organic layer was concentrated under reduced pressure. The residue was purified with silica gel column chromatography (silica gel, 5%-45% ethyl acetate/n-heptane) to afford the title compound (4.49 g).

¹H-NMR (400 MHz, CDCl₃) δ (ppm): 1.33 (t, J=7.1 Hz, 3H), 3.48 (s, 2H), 4.27 (q, J=7.1 Hz, 2H), 7.09-7.17 (m, 1H), 7.30-7.37 (m, 2H), 7.52-7.59 (m, 2H), 9.23 (br. s, 1H).

(2) Synthesis of 6-methyl-2-oxo-1-phenyl-1,2-dihydropyridine-3-carboxylic acid

A solution of ethyl 3-oxo-3-(phenylamino)propanoate (10.3 g, 49.8 mmol, 1 equivalent), acetylacetaldehyde dimethyl acetal (CAS No. 5436-21-5) (7.90 mL, 59.8 mmol, 1.2 equivalents) and sodium ethoxide (20% solution in ethanol, 63.5 mL, 164 mmol, 3.3 equivalents) in ethanol (137 mL) was stirred at 80° C. for 15 hours. The reaction mixture was allowed to return to room temperature, and then concentrated under reduced pressure. To the residue was added 5 M hydrochloric acid, and the mixture was extracted with DCM. The organic layer was concentrated under reduced pressure. The residue was triturated with a mixed solution of ethyl acetate-n-heptane, and the precipitate was collected by filtration. The resulting solid was washed with n-heptane to afford the title compound (10.3 g).
¹H-NMR (400 MHz, CDCl₃) δ (ppm): 2.12-2.17 (m, 3H), 6.51-6.58 (m, 1H), 7.20-7.25 (m, 2H), 7.53-7.67 (m, 3H), 8.52 (d, J=7.4 Hz, 1H). MS [M+H]⁺=230

(3) Synthesis of 5-bromo-6-methyl-2-oxo-1-phenyl-1,2-dihydropyridine-3-carboxylic acid A solution of 6-methyl-2-oxo-1-phenyl-1,2-dihydropyridine-3-carboxylic acid (10.3 g, 44.8 mmol, 1 equivalent) and NBS (8.78 g, 49.3 mmol, 1.1 equivalents) in DMF (100 mL) was stirred at room temperature for 1 hour. To the reaction mixture was added ice water, and the mixture was stirred at room temperature for 30 minutes, and then the precipitate was collected by filtration. The resulting solid was washed with water and n-heptane to afford the title compound (12.8 g).
¹H-NMR (400 MHz, CDCl₃) δ (ppm): 2.29 (s, 3H), 7.18-7.24 (m, 2H), 7.56-7.67 (m, 3H), 8.70 (s, 1H), 13.75 (s, 1H).
MS [M+H]⁺=308

(4) Synthesis of 5-bromo-6-methyl-1-phenylpyridin-2(1H)-one

A mixture of 5-bromo-6-methyl-2-oxo-1-phenyl-1,2-dihydropyridine-3-carboxylic acid (12.8 g, 41.5 mmol, 1 equivalent) and lithium hydroxide (2.19 g, 91.4 mmol, 2.2 equivalents) was stirred in a mixed solution of diglyme (271 mL) and water (26.9 mL) at 150° C. for 48 hours. During the reaction, water was distilled off from the reaction using a Dean-Stark apparatus. The reaction mixture was allowed to return to room temperature, and then concentrated under reduced pressure. The residue was triturated with water, and the precipitate was collected by filtration. The resulting solid was washed with water to afford the title compound (5.86 g).
¹H-NMR (400 MHz, CDCl₃) δ (ppm): 2.10 (s, 3H), 6.43-6.52 (m, 1H), 7.12-7.21 (m, 2H), 7.43-7.58 (m, 4H).
MS [M+H]⁺=266

(5) Synthesis of 3,5-difluoro-2'-methyl-1'-phenyl-[2,3'-bipyridin]-6'(1'H)-one

A mixture of 5-bromo-6-methyl-1-phenylpyridin-2(1H)-one (400 mg, 1.51 mmol, 1 equivalent), 3,5-difluoro-2-tributylstannylpyridine (CAS No. 765917-25-7) (673 mg, 1.67 mmol, 1.1 equivalents), Pd(PPh₃)₄ (88 rag, 0.076 mmol, 0.05 equivalents) and 1,4-dioxane (12 mL) was reacted in a microwave reactor at 150° C. for 7 hours. The reaction mixture was directly purified with silica gel column chromatography (NH silica gel, 10%-100% ethyl acetate/n-heptane) to afford the title compound (191 mg).
MS [M+H]⁺=299

(6) Synthesis of 5'-bromo-3,5-difluoro-2'-methyl-1'-phenyl-[2,3'-bipyridin]-6'(1'H)-one A solution of 3,5-difluoro-2'-methyl-1'-phenyl-[2,3'-bipyridin]-6'(1'H)-one (191 mg, 0.64 mmol, 1 equivalent) and NBS (171 mg, 0.96 mmol, 1.5 equivalents) in acetonitrile (5 mL) was stirred at room temperature for 15 hours. The reaction mixture was concentrated under reduced pressure. The residue was purified with silica gel column chromatography (NH silica gel on silica gel, 5%-65% ethyl acetate/n-heptane) to afford the title compound (155 mg).
¹H-NMR (400 MHz, CDCl₃) δ (ppm): 1.84-1.88 (m, 3H), 7.21-7.26 (m, 2H), 7.30-7.37 (m, 1H), 7.46-7.51 (m, 1H), 7.52-7.58 (m, 2H), 7.86-7.89 (m, 1H), 8.43-8.47 (m, 1H).
MS [M+H]⁺=377

(7) Synthesis of 9-bromo-3-fluoro-7-phenyl-6H-pyrano[3,2-b:5,4-b']dipyridin-8(7H)-one A solution of 5'-bromo-3,5-difluoro-2'-methyl-1'-phenyl-[2,3'-bipyridin]-6'(1'H)-one (162 mg, 0.429 mmol, 1 equivalent), NBS (84 mg, 0.472 mmol, 1.1 equivalents) and AIBN (3.53 mg, 0.021 mmol, 0.05 equivalents) in carbon tetrachloride (4 mL) was heated to reflux for 2 hours. The reaction mixture was allowed to return to room temperature, and then filtered. The residue was washed with carbon tetrachloride, and the filtrate was concentrated under reduced pressure. To the residue were added sodium carbonate (268 mg, 2.53 mmol, 5.89 equivalents), DMF (4.3 mL) and water (2.5 mL). The reaction mixture was stirred at 50° C. for 15 hours. The reaction mixture was allowed to return to room temperature, and then diluted with water. The mixture was stirred at room temperature for 2 hours, and the precipitate was collected by filtration. The resulting solid was washed with water and n-heptane to afford the title compound (82 mg).
¹H-NMR (400 MHz, CDCl₃) δ (ppm): 4.70 (s, 2H), 6.89-6.95 (m, 1H), 7.22-7.26 (m, 2H), 7.53-7.60 (m, 3H), 8.12 (d, J=2.4 Hz, 1H), 8.68 (s, 1H).
MS [M+H]⁺=375

(8) Synthesis of 3-(3-fluoro-8-oxo-7-phenyl-7,8-dihydro-6H-pyrano[3,2-b:5,4-b']dipyridin-9-yl)picolinonitrile A mixture of 9-bromo-3-fluoro-7-phenyl-6H-pyrano[3,2-b:5,4-b']dipyridin-8(7H)-one (82 mg, 0.22 mmol, 1 equivalent), 2-cyanopyridine-3-boronic acid neopentyl glycol ester (CAS No. 868944-75-6) (71.2 mg, 0.33 mmol, 1.5 equivalents), (Ataphos)₂PdCl₂ (7.78 mg, 11.0 μmol, 0.05 equivalents), potassium fluoride (2.21 M aqueous solution, 0.299 mL, 0.659 mmol, 3 equivalents), 1,4-dioxane (2.4 mL) and water (0.3 mL) was reacted in a microwave reactor at 130° C. for 2 hours. The reaction mixture was directly purified with silica gel column chromatography (NH silica gel, 5%-80% ethyl acetate/n-heptane). The resulting crude product was triturated with a mixed solution of ethanol-n-heptane (1:5), and the precipitate was collected by filtration. The resulting solid was washed with n-heptane to afford the title compound (55.6 mg).

$^1$H-NMR (400 MHz, CDCl$_3$) δ (ppm): 4.82 (s, 2H), 6.92-6.98 (m, 1H), 7.29-7.36 (m, 2H), 7.51-7.64 (m, 4H), 8.09 (dd, J=8.1, 1.6 Hz, 1H), 8.14 (d, J=2.4 Hz, 1H), 8.60 (s, 1H), 8.69 (dd, J=4.7, 1.6 Hz, 1H).

MS [M+Na]$^+$=419

Example 14

Synthesis of 2-fluoro-6-(3-fluoro-8-oxo-7-(pyridin-3-yl)-7,8-dihydro-6H-pyrano[3,2-b:5,4-b']dipyridin-9-yl)benzonitrile

[Chemical Formula 78]

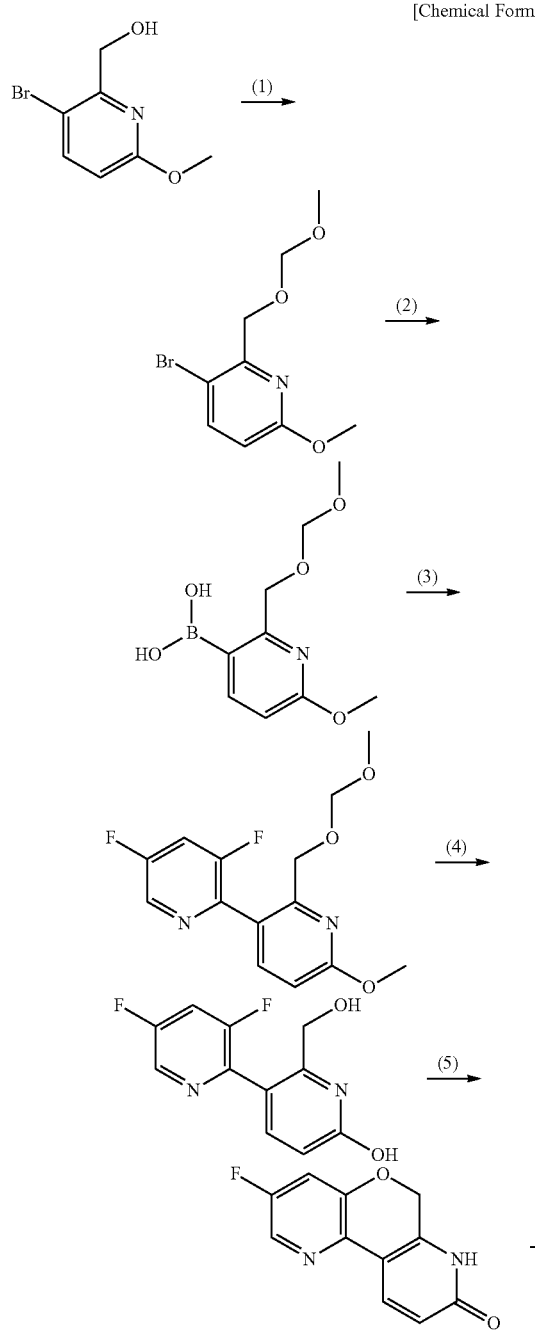

(1) Synthesis of 3-bromo-6-methoxy-2-((methoxymethoxy)methyl)pyridine

A mixture of (3-bromo-6-methoxypyridin-2-yl)methanol (CAS No. 623942-84-7) (2.15 g, 9.86 mmol, 1 equivalent), chloromethyl methyl ether (2.25 mL, 29.6 mmol, 3 equivalents) and N,N-diisopropylethylamine (8.61 mL, 49.3 mmol, 5 equivalents) was stirred in DCM (45 mL) at room temperature for 15 hours. The reaction mixture was concentrated under reduced pressure. The residue was purified with silica gel column chromatography (NH silica gel, 0%-5% ethyl acetate/n-heptane) to afford the title compound (2.22 g).

MS [M+H]$^+$=262

(2) Synthesis of (6-methoxy-2-((methoxymethoxy)methyl)pyridin-3-yl)boronic acid

A solution of 3-bromo-6-methoxy-2-((methoxymethoxy)methyl)pyridine (1.09 g, 4.16 mmol, 1 equivalent) in THF (20 mL) was cooled to −78° C., and n-butyllithium (2.69 M solution in n-hexane, 1.70 mL, 4.58 mmol, 1.1 equivalents) was added. The reaction mixture was stirred at the same temperature for 1 hour, and then trimethyl borate (0.696 mL, 6.24 mmol, 1.5 equivalents) was added. The reaction mixture was stirred for 12 hours while warming up to room temperature, and then concentrated under reduced pressure. To the residue was added a saturated aqueous ammonium chloride solution, and the mixture was extracted with DCM. The organic layer was concentrated under reduced pressure, and the residue was purified with silica gel column chromatography (silica gel, 10%-100% ethyl acetate/n-heptane) to afford the title compound (570 mg).

$^1$H-NMR (400 MHz, CDCl$_3$) δ (ppm): 3.42 (s, 3H), 3.95 (s, 3H), 4.75 (s, 2H), 4.79 (s, 2H), 6.32 (s, 2H), 6.71 (d, J=8.2 Hz, 1H), 8.08 (d, J=8.4 Hz, 1H).

MS [M+H]$^+$=228

(3) Synthesis of 3,5-difluoro-6'-methoxy-2'-((methoxymethoxy)methyl)-2,3'-bipyridine A mixture of (6-methoxy-2-((methoxymethoxy)methyl)pyridin-3-yl)boronic acid (570 mg, 2.51 mmol, 1 equivalent), 2-bromo-3,5-difluoropyridine (CAS No. 660425-16-1) (560 mg, 2.89 mmol, 1.15 equivalents), potassium fluoride (438 mg, 7.53 mmol, 3 equivalents), (Ataphos)$_2$PdCl$_2$ (89 mg, 0.126 mmol, 0.05 equivalents), 1,4-dioxane (12 mL) and water (3 mL) was reacted in a microwave reactor at 130° C. for 4 hours. The reaction mixture was cooled down to room temperature, and then directly purified with silica gel column chromatography (silica gel on NH silica gel, 5%-35% ethyl acetate/n-heptane) to afford the title compound (648 mg).

MS [M+H]$^+$=297

(4) Synthesis of 3,5-difluoro-2'-(hydroxymethyl)-[2,3'-bipyridin]-6'-ol

A mixture of 3,5-difluoro-6'-methoxy-2'-((methoxymethoxy)methyl)-2,3'-bipyridine (648 mg, 2.19 mmol, 1 equivalent) and a 48% aqueous hydrobromic acid solution (1.98 mL, 17.5 mmol, 8 equivalents) was stirred in THF (15 mL) at 55° C. for 8 hours. The reaction mixture was cooled down to room temperature, and then concentrated under reduced pressure. To the residue were added a saturated aqueous sodium hydrogen carbonate solution and DCM. The mixture was stirred at room temperature for 1 hour, and then the resulting precipitate was collected by filtration. The resulting solid was washed with water to afford the title compound (349 mg).

$^1$H-NMR (400 MHz, DMSO-d$_6$) δ (ppm): 4.33 (s, 2H), 6.35 (d, J=9.3 Hz, 1H), 7.51 (dd, J=9.3, 1.8 Hz, 1H), 8.04 (ddd, J=10.1, 8.9, 2.5 Hz, 1H), 8.57 (d, J=2.4 Hz, 1H).

MS [M+H]$^+$=239

(5) Synthesis of 3-fluoro-6H-pyrano[3,2-b:5,4-b']dipyridin-8(7H)-one

A mixture of 3,5-difluoro-2'-(hydroxymethyl)-[2,3'-bipyridin]-6'-ol (329 mg, 1.38 mmol, 1 equivalent) and potassium carbonate (573 mg, 4.14 mmol, 3 equivalents) was stirred in DMF (7 mL) at 100° C. for 5 hours. The reaction mixture was cooled down to room temperature, and then an aqueous ammonium chloride solution was added. The mixture was stirred at room temperature for 30 minutes, and then the resulting precipitate was collected by filtration. The resulting solid was washed with water and n-heptane to afford the title compound (251 mg).

$^1$H-NMR (400 MHz, DMSO-d$_6$) δ (ppm): 5.20 (s, 2H), 6.46 (d, J=8.8 Hz, 1H), 7.38 (dd, J=9.7, 2.4 Hz, 1H), 8.04 (d, J=9.3 Hz, 1H), 8.19 (d, J=2.6 Hz, 1H).

MS [M+H]$^+$=219

(6) Synthesis of 3-fluoro-7-(pyridin-3-yl)-6H-pyrano[3,2-b:5,4-b']dipyridin-8(7H)-one A mixture of 3-fluoro-6H-pyrano[3,2-b:5,4-b']dipyridin-8(7H)-one (250 mg, 1.15 mmol, 1 equivalent), silver carbonate (474 mg, 1.72 mmol, 1.5 equivalents), copper(I) iodide (131 mg, 0.687 mmol, 0.6 equivalents) and pyridine (0.927 mL, 11.5 mmol, 10 equivalents) was stirred in a mixed solvent of DMF (7 mL) and DMSO (9 mL) at 80° C. for 20 minutes. To the reaction mixture was slowly added a mixed solution of pyridine-3-boronic acid 1,3-propanediol cyclic ester (CAS No. 131534-65-1) (373 mg, 2.29 mmol, 2 equivalents) in DMF (4 mL) and DMSO (1 mL). The reaction mixture was stirred at 80° C. for 20 hours, then applied to silica gel pad (NH silica gel and silica gel) and eluted with ethyl acetate. The resulting solution was concentrated under reduced pressure. To the residue was added water, and the mixture was extracted with ethyl acetate. The organic layer was washed with a saturated aqueous sodium chloride solution, and then concentrated under reduced pressure. The residue was purified with silica gel column chromatography (NH silica gel on silica gel, 10%-100% ethyl acetate/n-heptane, 10% methanol/ethyl acetate) to afford the title compound (43.5 mg).

$^1$H-NMR (400 MHz, CDCl$_3$) δ (ppm): 4.64-4.73 (m, 1H), 4.77-4.86 (m, 1H), 6.78 (d, J=9.5 Hz, 1H), 6.94 (dd, J=8.9, 2.5 Hz, 1H), 7.51-7.58 (m, 1H), 7.65-7.72 (m, 1H), 8.14 (d, J=2.6 Hz, 1H), 8.29 (d, J=9.7 Hz, 1H), 8.53 (d, J=2.6 Hz, 1H), 8.79 (dd, J=4.8, 1.5 Hz, 1H).

MS [M+H]$^+$=296

(7) Synthesis of 9-bromo-3-fluoro-7-(pyridin-3-yl)-6H-pyrano[3,2-b:5,4-b']dipyridin-8(7H)-one A mixture of 3-fluoro-7-(pyridin-3-yl)-6H-pyrano[3,2-b:5,4-b']dipyridin-8(7H)-one (43.5 mg, 0.147 mmol, 1 equivalent) and NBS (31.5 mg, 0.177 mmol, 1.2 equivalents) was stirred in acetonitrile (3 mL) at room temperature for 15 hours. The reaction mixture was directly purified with silica gel column chromatography (NH silica gel on silica gel, 10%-100% ethyl acetate/n-heptane) to afford the title compound (33 mg).

$^1$H-NMR (400 MHz, CDCl$_3$) δ (ppm): 4.60-4.70 (m, 1H), 4.74-4.83 (m, 1H), 6.95 (dd, J=8.6, 2.0 Hz, 1H), 7.56 (dd, J=8.1, 4.8 Hz, 1H), 7.65-7.72 (m, 1H), 8.14 (d, J=2.4 Hz, 1H), 8.53 (d, J=2.4 Hz, 1H), 8.71 (s, 1H), 8.81 (dd, J=4.9, 1.6 Hz, 1H).

MS [M+Na]$^+$=396

(8) Synthesis of 2-fluoro-6-(3-fluoro-8-oxo-7-(pyridin-3-yl)-7,8-dihydro-6H-pyrano[3,2-b:5,4-b']dipyridin-9-yl)benzonitrile A mixture of 9-bromo-3-fluoro-7-(pyridin-3-yl)-6H-pyrano[3,2-b:5,4-b']dipyridin-8(7H)-one (16.5 mg, 0.044 mmol, 1 equivalent), 2-cyano-3-fluorophenylboronic acid pinacol ester (CAS No. 765916-91-4) (14.2 mg, 0.057 mmol, 1.3 equivalents), (Ataphos)$_2$PdCl$_2$ (1.56 mg, 2.21 μmol, 0.05 equivalents), triethylamine (0.025 mL, 0.176 mmol, 4 equivalents), 1,4-dioxane (0.5 mL) and water (0.15 mL) was reacted in a microwave reactor at 130° C. for 2.5 hours. The reaction solution was directly purified with silica gel column chromatography (NH silica gel on silica gel, 5%-90% ethyl acetate/n-heptane) to afford the title compound (11.0 mg).

$^1$H-NMR (400 MHz, CDCl$_3$) δ (ppm): 4.71-4.80 (m, 1H), 4.86-4.95 (m, 1H), 6.97 (dd, J=8.8, 2.4 Hz, 1H), 7.20-7.28 (m, 1H), 7.46 (d, J=7.7 Hz, 1H), 7.57 (dd, J=8.2, 4.8 Hz, 1H), 7.63 (td, J=8.2, 5.8 Hz, 1H), 7.77 (ddd, J=8.1, 2.6, 1.6 Hz, 1H), 8.14 (d, J=2.6 Hz, 1H), 8.51 (s, 1H), 8.60 (d, J=2.6 Hz, 1H), 8.81 (dd, J=4.9, 1.6 Hz, 1H).

MS [M+H]$^+$=415

Example 15

Synthesis of 2-fluoro-6-(7-(5-fluoropyridin-3-yl)-8-oxo-7,8-dihydro-6H-pyrano[3,2-b:5,4-b']dipyridin-9-yl)benzonitrile

[Chemical Formula 79]

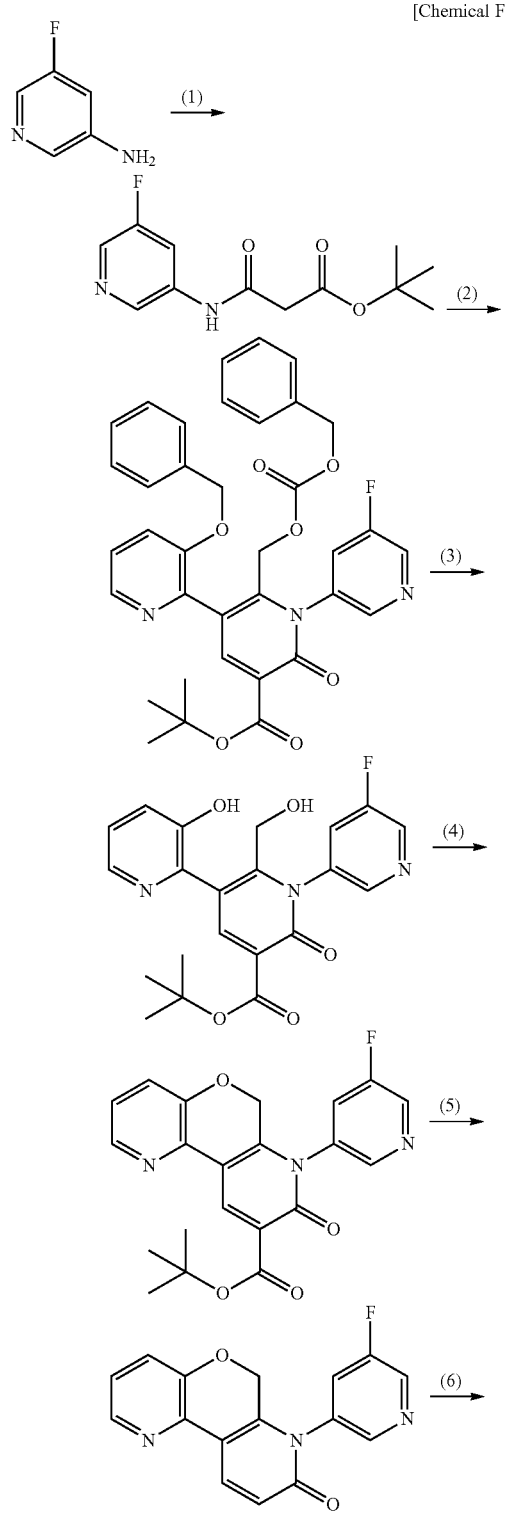

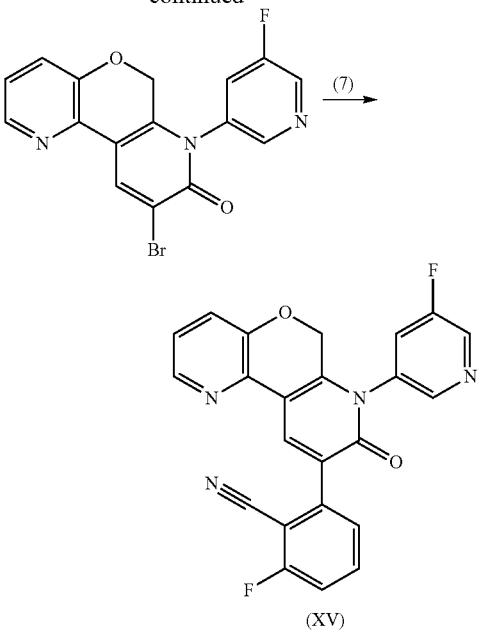

(1) Synthesis of t-butyl 3-((5-fluoropyridin-3-yl)amino)-3-oxopropanoate 3-(t-Butoxy)-3-oxopropionic acid (CAS No. 40052-13-9) (2.75 mL, 17.8 mmol, 2 equivalents) and 3-amino-5-fluoropyridine (CAS No. 210169-05-4) (1.00 g, 8.92 mmol, 1 equivalent) were dissolved in DMF (15 mL), and triethylamine (6.22 mL, 44.6 mmol, 5 equivalents) and EDC (5.13 g, 26.8 mmol, 3 equivalents) were added, and the mixture was stirred at 60° C. for 24 hours. The reaction mixture was cooled down to room temperature. To the reaction mixture were added water and ethyl acetate, and the organic and aqueous layers were separated. The aqueous layer was extracted twice with ethyl acetate. The combined organic layers were dried over anhydrous magnesium sulfate, filtered, and then concentrated under reduced pressure. The residue was purified with silica gel column chromatography (silica gel, 60%-90% ethyl acetate/n-heptane) to afford the title compound (2.1 g).

$^1$H-NMR (400 MHz, CDCl$_3$) δ (ppm): 1.52 (s, 9H), 3.42 (s, 2H), 8.16 (dt, J=10.5, 2.7 Hz, 1H), 8.23 (d, J=2.7 Hz, 1H), 8.31-8.49 (m, 1H), 9.83 (br. s., 1H).

(2) Synthesis of t-butyl 3-(benzyloxy)-2'-((((benzyloxy)carbonyl)oxy)methyl)-5''-fluoro-6'-oxo-6'H-[2,3':1',3''-terpyridine]-5'-carboxylate t-Butyl 3-((5-fluoropyridin-3-yl)amino)-3-oxopropanoate (1.13 g, 4.44 mmol, 1 equivalent) and benzyl (3-(3-(benzyloxy)pyridin-2-yl)-4-methoxy-2-oxobut-3-en-1-yl)carbonate (E/Z mixture) obtained in Production Example 9 (2.02 g, 4.67 mmol, 1.05 equivalents) were dissolved in propionitrile (30 mL), and cooled to 0° C. To the solution were added lithium bromide (772 mg, 8.89 mmol, 2 equivalents) and triethylamine (2.17 mL, 15.6 mmol, 3.5 equivalents), and the mixture was stirred at 0° C. for 1 hour. To the reaction mixture were added water and ethyl acetate, and the organic and aqueous layers were separated. The aqueous layer was extracted with ethyl acetate. The combined organic layers were dried over anhydrous magnesium sulfate, filtered, and then concentrated under reduced pressure. The residue was purified with silica gel column chromatography (silica gel, 60%-80% ethyl acetate/n-heptane) to afford the title compound (2.02 g).

MS [M+H]$^+$=638

(3) Synthesis of t-butyl 5"-fluoro-3-hydroxy-2'-(hydroxymethyl)-6'-oxo-6'H-[2,3':1',3"-terpyridine]-5'-carboxylate t-Butyl 3-(benzyloxy)-2'-((((benzyloxy)carbonyl)oxy)methyl)-5"-fluoro-6'-oxo-6'H-[2,3':1',3"-terpyridine]-5'-carboxylate (2.02 g, 3.17 mmol, 1 equivalent) was dissolved in ethanol (45.4 mL), and methanesulfonic acid (0.411 mL, 6.34 mmol, 2 equivalents) and 10% palladium on carbon (water content, 50.98%) (200 mg) were added. The reaction mixture was stirred at room temperature under a hydrogen atmosphere for 1 hour. The reaction mixture was diluted with ethyl acetate, and then triethylamine (1.33 mL, 9.50 mmol, 3 equivalents) was added. The reaction mixture was filtered through Celite™, and the residue was washed with ethyl acetate. The combined filtrates were concentrated under reduced pressure. The residue was purified with silica gel column chromatography (silica gel, 0%-20% methanol/ethyl acetate) to afford the title compound (1.23 g).

$^1$H-NMR (400 MHz, CDCl$_3$) δ (ppm): 1.54 (s, 9H), 3.81-3.95 (m, 1H), 3.95-4.09 (m, 1H), 7.21 (dd, J=8.2, 4.7 Hz, 1H), 7.32 (dd, J=8.2, 1.2 Hz, 1H), 7.58 (d, J=8.2 Hz, 1H), 8.11-8.28 (m, 1H), 8.42 (d, J=2.0 Hz, 1H), 8.49 (s, 1H), 8.57 (d, J=2.7 Hz, 1H).

MS [M+H]$^+$=414

(4) Synthesis of t-butyl 7-(5-fluoropyridin-3-yl)-8-oxo-7,8-dihydro-6H-pyrano[3,2-b:5,4-b']dipyridine-9-carboxylate t-Butyl 5"-fluoro-3-hydroxy-2'-(hydroxymethyl)-6'-oxo-6'H-[2,3':1',3"-terpyridine]-5'-carboxylate (1.20 g, 2.90 mmol, 1 equivalent) was dissolved in THF (50 mL), and a solution of triphenylphosphine (837 mg, 3.19 mmol, 1.1 equivalents) and DMEAD (748 mg, 3.19 mmol, 1.1 equivalents) in THF (3 mL) was added at 0° C. The reaction mixture was warmed to room temperature and stirred for 1 hour. To the reaction mixture were added water and ethyl acetate, and the organic and aqueous layers were separated. The aqueous layer was extracted twice with ethyl acetate. The combined organic layers were dried over anhydrous magnesium sulfate, filtered, and then concentrated under reduced pressure. The residue was purified with silica gel column chromatography (silica gel, 50%-100% ethyl acetate/n-heptane, 15% methanol/ethyl acetate) to afford the title compound (645 mg).

$^1$H-NMR (400 MHz, CDCl$_3$) δ (ppm): 1.60 (s, 9H), 4.67 (d, J=16.0 Hz, 1H), 4.82 (d, J=16.0 Hz, 1H), 7.09-7.23 (m, 2H), 7.49 (dt, J=8.0, 2.4 Hz, 1H), 8.29 (dd, J=4.3, 1.6 Hz, 1H), 8.35 (d, J=2.0 Hz, 1H), 8.68 (d, J=2.3 Hz, 1H), 8.96 (s, 1H).

MS m/z=397

(5) Synthesis of 7-(5-fluoropyridin-3-yl)-6H-pyrano[3,2-b:5,4-b']dipyridin-8(7H)-one t-Butyl 7-(5-fluoropyridin-3-yl)-8-oxo-7,8-dihydro-6H-pyrano[3,2-b:5,4-b']dipyridine-9-carboxylate (645 mg, 1.63 mmol, 1 equivalent) was dissolved in TFA (10 mL), and stirred at room temperature for 20 minutes. The reaction mixture was concentrated under reduced pressure. The residue was dissolved in DMSO (10 mL), and lithium acetate dihydrate (1.66 g, 16.3 mmol, 10 equivalents) was added, and the mixture was stirred at 100° C. for 2 hours. The reaction mixture was cooled down to room temperature. To the reaction mixture were added water and ethyl acetate, and the organic and aqueous layers were separated. The aqueous layer was extracted twice with ethyl acetate. The combined organic layers were dried over anhydrous magnesium sulfate, filtered, and then concentrated under reduced pressure. The residue was triturated with a mixed solution of 10% ethyl acetate/n-heptane, and the solid was collected by filtration. The resulting solid was washed with n-heptane to afford the title compound (308 mg).

MS [M+H]$^+$=296

(6) Synthesis of 9-bromo-7-(5-fluoropyridin-3-yl)-6H-pyrano[3,2-b:5,4-b']dipyridin-8(7H)-one 7-(5-Fluoropyridin-3-yl)-6H-pyrano[3,2-b:5,4-b']dipyridin-8(7H)-one (305 mg, 1.03 mmol, 1 equivalent) was dissolved in DMF (15 mL), and NBS (202 mg, 1.14 mmol, 1.1 equivalents) was added, and the mixture was stirred for 14 hours. To the reaction mixture was added additional NBS (202 mg, 1.14 mmol, 1.1 equivalents), and the mixture was stirred for another hour. To the reaction mixture were added water and ethyl acetate, and the organic and aqueous layers were separated. The aqueous layer was extracted twice with ethyl acetate. The organic layer was dried over anhydrous magnesium sulfate, filtered, and then concentrated under reduced pressure. The residue was purified with silica gel column chromatography (silica gel, 50%-70% ethyl acetate/n-heptane) to afford the title compound (132 mg).

$^1$H-NMR (400 MHz, CDCl$_3$) δ (ppm): 4.64 (d, J=16.0 Hz, 1H), 4.78 (d, J=16.0 Hz, 1H), 7.05-7.22 (m, 2H), 7.49 (dt, J=8.1, 2.2 Hz, 1H), 8.27 (dd, J=4.3, 1.6 Hz, 1H), 8.37 (d, J=2.3 Hz, 1H), 8.70 (d, J=2.3 Hz, 1H), 8.78 (s, 1H).

MS [M+H]$^+$=374

(7) Synthesis of 2-fluoro-6-(7-(5-fluoropyridin-3-yl)-8-oxo-7,8-dihydro-6H-pyrano[3,2-b:5,4-b']dipyridin-9-yl)benzonitrile A mixture of 9-bromo-7-(5-fluoropyridin-3-yl)-6H-pyrano[3,2-b:5,4-b']dipyridin-8(7H)-one (4.9 mg, 0.013 mmol, 1 equivalent), 2-cyano-3-fluorophenylboronic acid pinacol ester (CAS No. 765916-91-4) (4.85 mg, 0.020 mmol, 1.5 equivalents), (Ataphos)$_2$PdCl$_2$ (0.46 mg, 0.655 μmol, 0.05 equivalents), potassium fluoride (2.28 mg, 0.039 mmol, 3 equivalents), water (0.2 mL) and 1,4-dioxane (0.5 mL) was reacted in a microwave reactor at 140° C. for 2 hours. The reaction mixture was concentrated Tinder reduced pressure. The residue was purified with silica gel column chromatography (silica gel, 80%400% ethyl acetate/n-heptane) to afford the title compound (2.3 mg).

$^1$H-NMR (400 MHz, CDCl$_3$) δ (ppm): 4.75 (d, J=15.6 Hz, 1H), 4.90 (d, J=15.6 Hz, 1H), 7.14 (dd, J=9.0, 5.1 Hz, 1H), 7.18-7.26 (m, 2H), 7.45 (d, J=7.8 Hz, 1H), 7.57 (dt, J=8.0, 2.4 Hz, 1H), 7.64 (td, J=8.1, 5.7 Hz, 1H), 8.26 (dd, J=4.7, 1.6 Hz, 1H), 8.44 (d, J=2.0 Hz, 1H), 8.57 (s, 1H), 8.70 (d, J=2.7 Hz, 1H).

MS [M+H]$^+$=415

Example 16

Synthesis of 2-fluoro-6-(10-fluoro-3-oxo-4-(pyridin-3-yl)-4,5-dihydro-3H-chromeno[3,4-b]pyridin-2-yl)benzonitrile

[Chemical Formula 80]

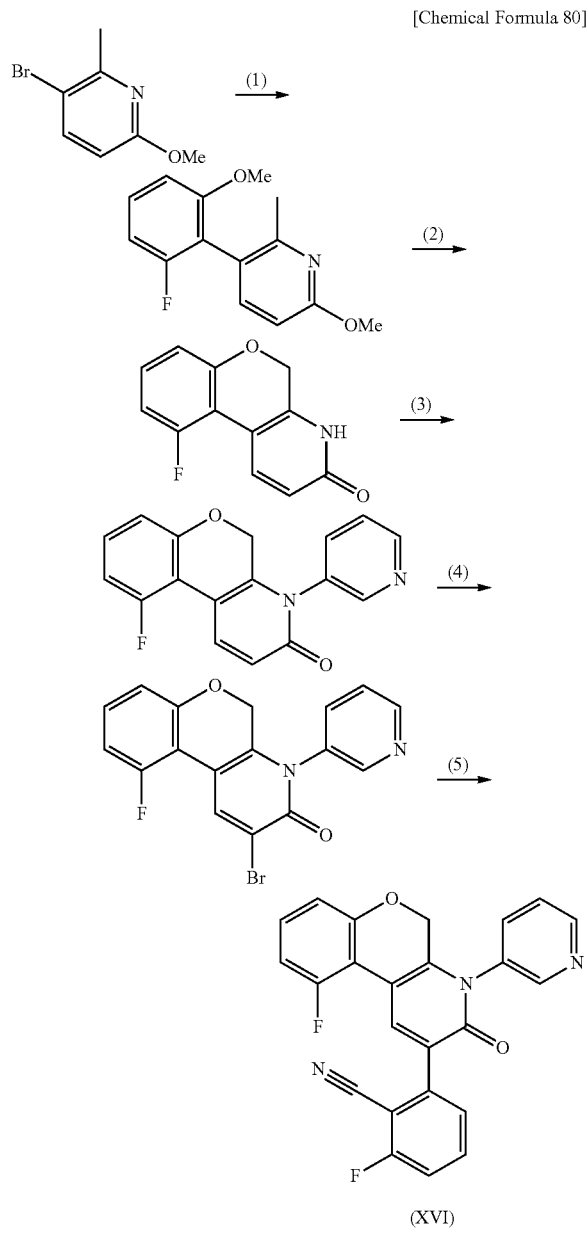

(1) Synthesis of 3-(2-fluoro-6-methoxyphenyl)-6-methoxy-2-methylpyridine

A mixture of 3-bromo-6-methoxy-2-picoline (CAS No. 126717-59-7) (1 g, 4.95 mmol, 1 equivalent), (2-fluoro-6-methoxyphenyl)boronic acid (CAS No. 78495-63-3) (925 mg, 5.44 mmol, 1.1 equivalents), (Ataphos)$_2$PdCl$_2$ (175 mg, 0.247 mmol, 0.05 equivalents), sodium carbonate (787 mg, 7.42 mmol, 1.5 equivalents), DME (15 mL) and water (5 mL) was reacted in a microwave reactor at 110° C. for 1.5 hours. A total of four similar reactions were performed, and then worked up together.

To the reaction mixture was added water, and the mixture was extracted with ethyl acetate. The organic layer was washed sequentially with water and a saturated aqueous sodium chloride solution. The organic layer was dried over sodium sulfate, filtered, and then concentrated under reduced pressure. The residue was purified with silica gel column chromatography (NH silica gel on silica gel, 0%-20% ethyl acetate/n-heptane) to afford the title compound (3.41 g).

$^1$H-NMR (400 MHz, CDCl$_3$) δ (ppm): 2.26 (s, 3H), 3.77 (s, 3H), 3.96 (s, 3H), 6.59-6.69 (m, 1H), 6.74-6.83 (m, 2H), 7.30 (td, J=8.4, 6.6 Hz, 1H), 7.37 (d, J=8.6 Hz, 1H).

(2) Synthesis of 10-fluoro-4,5-dihydro-3H-chromeno[3,4-b]pyridin-3-one

A mixture of 3-(2-fluoro-6-methoxyphenyl)-6-methoxy-2-methylpyridine (1.4 g, 5.66 mmol, 1 equivalent), NBS (1.11 g, 6.23 mmol, 1.1 equivalents), AIBN (46 mg, 0.283 mmol, 0.05 equivalents) and carbon tetrachloride (60 mL) was heated to reflux for 40 minutes. The reaction mixture was allowed to return to room temperature, and then concentrated under reduced pressure. The residue was purified with silica gel column chromatography (silica gel, 0%-9.09% ethyl acetate/n-heptane). The resulting crude product was dissolved in a 48% aqueous hydrobromic acid solution (40 mL). The reaction mixture was stirred under heating to reflux overnight. To the solution was added a 48% aqueous hydrobromic acid solution (10 mL). The reaction mixture was stirred under heating to reflux for 8 hours. To the solution was added a 48% aqueous hydrobromic acid solution (10 mL). The reaction mixture was stirred under heating to reflux overnight. The reaction mixture was allowed to return to room temperature, and then concentrated under reduced pressure. To the residue was added a saturated aqueous sodium hydrogen carbonate solution until the pH of the solution was pH≥7. The precipitate was collected by filtration. The resulting solid was washed sequentially with water, n-heptane and ethyl acetate to afford the title compound (776 mg).

$^1$H-NMR (400 MHz, DMSO-d$_6$) δ (ppm): 4.96 (s, 2H), 6.37 (br. s, 1H), 6.82 (d, J=8.2 Hz, 1H), 6.86-6.98 (m, 1H), 7.07-7.22 (m, 1H), 7.90 (d, J=9.0 Hz, 1H), 11.84-12.18 (m, 1H).

(3) Synthesis of 10-fluoro-4-(pyridin-3-yl)-4,5-dihydro-3H-chromeno[3,4-b]pyridin-3-one A mixture of 10-fluoro-4,5-dihydro-3H-chromeno[3,4-b]pyridin-3-one (300 mg, 1.38 mmol, 1 equivalent), silver carbonate (571 mg, 2.07 mmol, 1.5 equivalents), copper(I) iodide (158 mg, 0.829 mmol, 0.6 equivalents), pyridine (1.12 mL, 13.8 mmol, 10 equivalents) and DMF (15 mL) was stirred at 80° C. for 20 minutes. To the reaction mixture was added pyridine-3-boronic acid (CAS No. 1692-25-7) (85 mg, 0.691 mmol, 0.5 equivalents) five times, every 30 minutes (0.5×5=2.5 equivalents in total). The reaction mixture was allowed to return to room temperature, then applied to Celite™ pad (NH silica gel on Celite™) and eluted ethyl acetate. The resulting solution was concentrated under reduced pressure, and the residue was purified with silica gel column chromatography (silica gel, 20%-75% ethyl acetate/n-heptane) to afford the title compound (15.7 mg).

$^1$H-NMR (400 MHz, CDCl$_3$) δ (ppm): 4.45-4.54 (m, 1H), 4.58-4.65 (m, 1H), 6.71-6.79 (m, 2H), 6.84 (ddd, J=11.4, 8.4, 1.1 Hz, 1H), 7.14 (td, J=8.3, 6.1 Hz, 1H), 7.55 (ddd, J=8.1, 4.8, 0.8 Hz, 1H), 7.70 (ddd, J=8.2, 2.5, 1.6 Hz, 1H), 8.16 (d, J=9.8 Hz, 1H), 8.52 (dd, 2.5, 0.8 Hz, 1H), 8.78 (dd, J=4.9, 1.6 Hz, 1H).

(4) Synthesis of 2-bromo-10-fluoro-4-(pyridin-3-yl)-4,5-dihydro-3H-chromeno[3,4-b]pyridin-3-one A mixture of 10-fluoro-4-(pyridin-3-yl)-4,5-dihydro-3H-chromeno[3,4-b]pyridin-3-one (15.7 nag, 0.053 mmol, 1 equivalent), NBS (10.5 mg, 0.059 mmol, 1.1 equivalents) and DMF (0.5 mL) was stirred at room temperature for 1.5 hours. To the reaction mixture was added NBS (5 mg, 0.028 mmol, 0.527 equivalents). The reaction mixture was stirred for 30 minutes. To the reaction mixture was added water, and the mixture was extracted with ethyl acetate. The organic layer was washed sequentially with water and a saturated aqueous sodium chloride solution. The organic layer was dried over sodium sulfate, filtered, and then concentrated under reduced pressure. The residue was purified with preparative TLC (silica gel, 60% ethyl acetate/n-heptane) to afford the title compound (6.5 mg).
MS [M+H]$^+$=373

(5) Synthesis of 2-fluoro-6-(10-fluoro-3-oxo-4-(pyridin-3-yl)-4,5-dihydro-3H-chromeno[3,4-b]pyridin-2-yl)benzonitrile A mixture of 2-bromo-10-fluoro-4-(pyridin-3-yl)-4,5-dihydro-3H-chromeno[3,4-b]pyridin-3-one (50 mg, 0.134 mmol, 1 equivalent), 2-cyano-3-fluorophenylboronic acid pinacol ester (CAS No. 765916-91-4) (49.7 mg, 0.201 mmol, 1.5 equivalents), (Ataphos)$_2$PdCl$_2$ (4.74 mg, 6.70 μmol, 0.05 equivalents), potassium fluoride (23.4 mg, 0.402 mmol, 3 equivalents), 1,4-dioxane (0.8 mL) and water (0.2 mL) was reacted in a microwave reactor at 130° C. for 10 minutes. The reaction mixture was directly purified with silica gel column chromatography (NH silica gel, 10%-67% ethyl acetate/n-heptane) to afford the title compound (39.8 mg).
$^1$H-NMR (400 MHz, CDCl$_3$) δ (ppm): 4.54-4.61 (m, 1H), 4.65-4.72 (m, 1H), 6.80 (d, J=8.0 Hz, 1H), 6.83-6.91 (m, 1H), 7.13-7.25 (m, 2H), 7.48 (d, J=6.8 Hz, 1H), 7.57 (dd, J=8.0, 4.7 Hz, 1H), 7.64 (td, J=8.2, 5.8 Hz, 1H), 7.73-7.82 (m, 1H), 8.37 (s, 1H), 8.58 (d, J=2.5 Hz, 1H), 8.80 (dd, J=4.8, 1.5 Hz, 1H).
MS [M+H]$^+$=414

Example 17

Synthesis of 9-(2-chloro-3-fluorophenyl)-7-(5-fluoropyridin-3-yl)-6H-pyrano[3,2-b:5,4-b']dipyridin-8(7H)-one

[Chemical Formula 81]

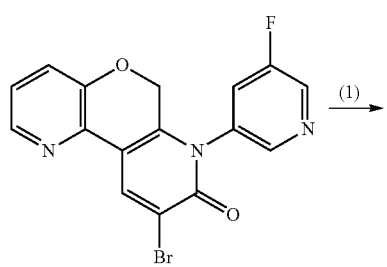

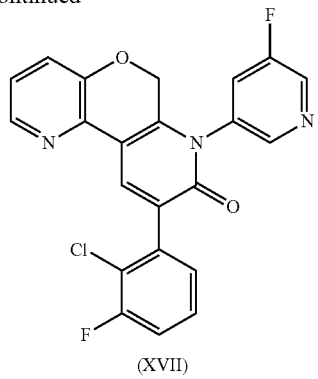

(XVII)

(1) Synthesis of 9-(2-chloro-3-fluorophenyl)-7-(5-fluoropyridin-3-yl)-6H-pyrano[3,2-b:5,4-b']dipyridin-8(7H)-one A mixture of 9-bromo-7-(5-fluoropyridin-3-yl)-6H-pyrano[3,2-b:5,4-b']dipyridin-8(7H)-one obtained in Example 15-(6) (7.0 mg, 0.019 mmol, 1 equivalent), 2-chloro-3-fluorophenylboronic acid (CAS No. 871329-52-1) (3.26 mg, 0.019 mmol, 1 equivalent), (Ataphos)$_2$PdCl$_2$ (0.66 mg, 0.935 μmol, 0.05 equivalents), potassium fluoride (3.26 mg, 0.056 mmol, 3 equivalents), water (0.1 mL) and 1,4-dioxane (0.5 mL) was reacted in a microwave reactor at 150° C. for 5 minutes. The reaction mixture was concentrated under reduced pressure. The residue was purified with silica gel column chromatography (silica gel, 50%-70% ethyl acetate/n-heptane) to afford the title compound (3.8 mg).
$^1$H-NMR (400 MHz, CDCl$_3$) δ (ppm): 4.75 (d, J=15.6 Hz, 1H), 4.90 (d, 15.6 Hz, 1H), 7.08-7.41 (m, 5H), 7.50-7.63 (m, 1H), 8.25 (dd, J=4.7, 1.6 Hz, 1H), 8.38-8.48 (m, 2H), 8.68 (d, J=2.7 Hz, 1H).
MS [M+H]$^+$=424

Example 18

Synthesis of 2-fluoro-6-(8-oxo-7-(pyrimidin-5-yl)-7,8-dihydro-6H-pyrano[3,2-b:5,4-b']dipyridin-9-yl)benzonitrile

[Chemical Formula 82]

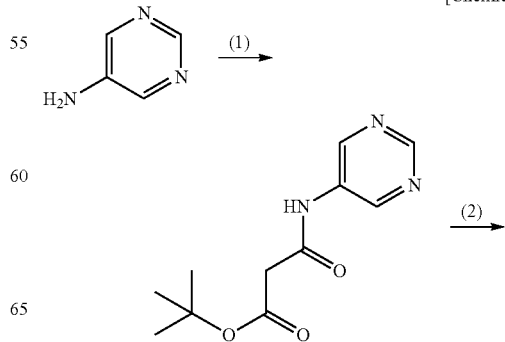

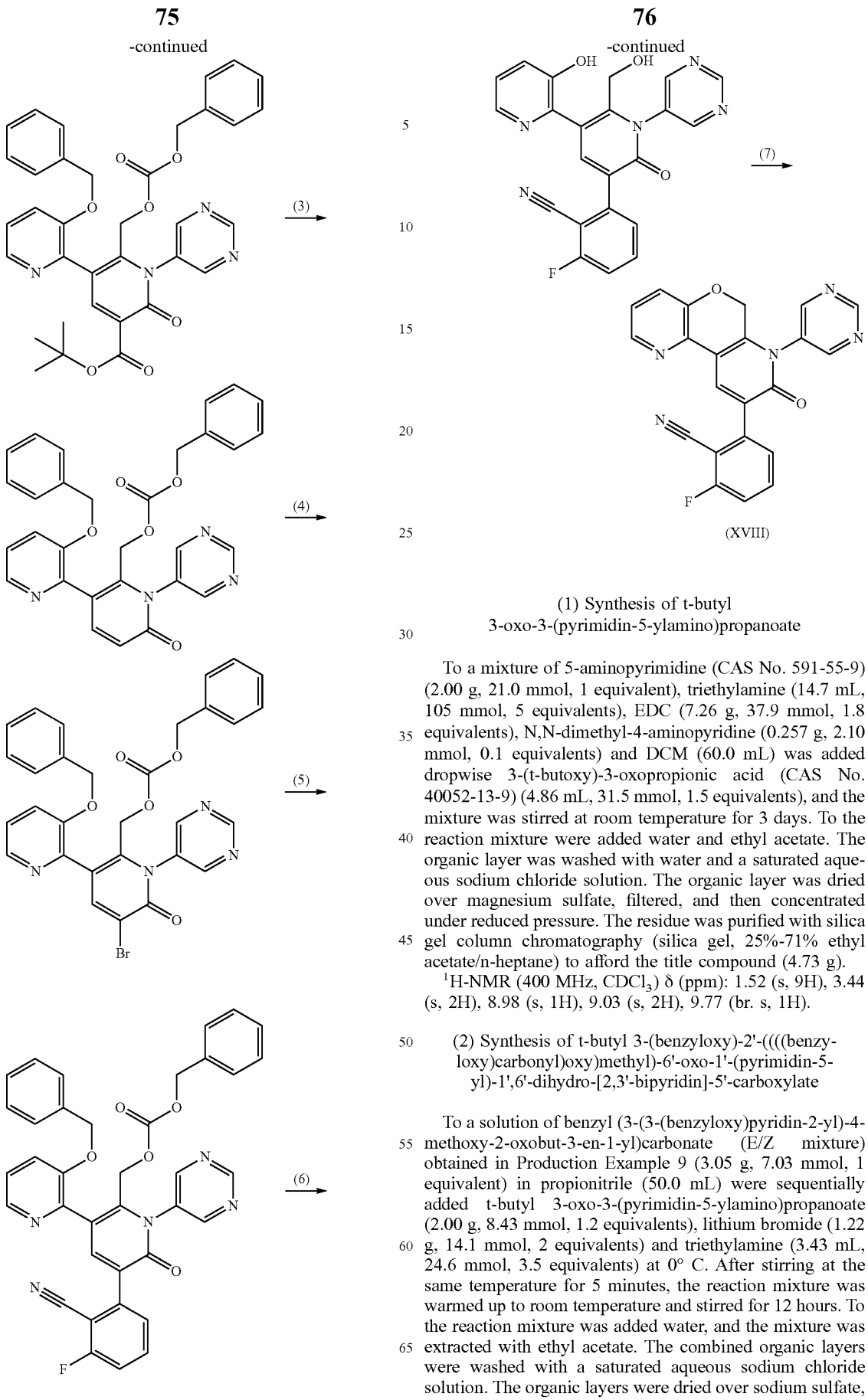

(1) Synthesis of t-butyl 3-oxo-3-(pyrimidin-5-ylamino)propanoate

To a mixture of 5-aminopyrimidine (CAS No. 591-55-9) (2.00 g, 21.0 mmol, 1 equivalent), triethylamine (14.7 mL, 105 mmol, 5 equivalents), EDC (7.26 g, 37.9 mmol, 1.8 equivalents), N,N-dimethyl-4-aminopyridine (0.257 g, 2.10 mmol, 0.1 equivalents) and DCM (60.0 mL) was added dropwise 3-(t-butoxy)-3-oxopropionic acid (CAS No. 40052-13-9) (4.86 mL, 31.5 mmol, 1.5 equivalents), and the mixture was stirred at room temperature for 3 days. To the reaction mixture were added water and ethyl acetate. The organic layer was washed with water and a saturated aqueous sodium chloride solution. The organic layer was dried over magnesium sulfate, filtered, and then concentrated under reduced pressure. The residue was purified with silica gel column chromatography (silica gel, 25%-71% ethyl acetate/n-heptane) to afford the title compound (4.73 g).

$^1$H-NMR (400 MHz, CDCl$_3$) δ (ppm): 1.52 (s, 9H), 3.44 (s, 2H), 8.98 (s, 1H), 9.03 (s, 2H), 9.77 (br. s, 1H).

(2) Synthesis of t-butyl 3-(benzyloxy)-2'-((((benzyloxy)carbonyl)oxy)methyl)-6'-oxo-1'-(pyrimidin-5-yl)-1',6'-dihydro-[2,3'-bipyridin]-5'-carboxylate To a solution of benzyl (3-(3-(benzyloxy)pyridin-2-yl)-4-methoxy-2-oxobut-3-en-1-yl)carbonate (E/Z mixture) obtained in Production Example 9 (3.05 g, 7.03 mmol, 1 equivalent) in propionitrile (50.0 mL) were sequentially added t-butyl 3-oxo-3-(pyrimidin-5-ylamino)propanoate (2.00 g, 8.43 mmol, 1.2 equivalents), lithium bromide (1.22 g, 14.1 mmol, 2 equivalents) and triethylamine (3.43 mL, 24.6 mmol, 3.5 equivalents) at 0° C. After stirring at the same temperature for 5 minutes, the reaction mixture was warmed up to room temperature and stirred for 12 hours. To the reaction mixture was added water, and the mixture was extracted with ethyl acetate. The combined organic layers were washed with a saturated aqueous sodium chloride solution. The organic layers were dried over sodium sulfate, filtered, and then concentrated under reduced pressure. The residue was purified with silica gel column chromatography (NH silica gel, 20%-75% ethyl acetate/n-heptane). The resulting crude product was triturated with a mixed solution of MTBE/n-heptane to afford the title compound (2.30 g).

$^1$H-NMR (400 MHz, CDCl$_3$) δ (ppm): 1.55 (s, 9H), 4.70 (s, 2H), 4.93 (s, 2H), 5.07 (s, 2H), 7.24-7.27 (m, 1H), 7.29-7.42 (m, 11H), 8.26 (dd, J=4.7, 1.6 Hz, 1H), 8.34 (s, 1H), 8.62 (d, J=0.8 Hz, 2H), 9.21 (s, 1H).

(3) Synthesis of benzyl ((3-(benzyloxy)-6'-oxo-1'-(pyrimidin-5-yl)-1',6'-dihydro-[2,3'-bipyridin]-2'-yl)methyl)carbonate To t-butyl 3-(benzyloxy)-2'-((((benzyloxy)carbonyl)oxy)methyl)-6'-oxo-1'-(pyrimidin-5-yl)-1',6'-dihydro-[2,3'-bipyridine]-5'-carboxylate (1.56 g, 2.51 mmol, 1 equivalent) was added hydrogen chloride (4 M solution in ethyl acetate) (6.28 mL, 25.1 mmol, 10 equivalents), and the mixture was stirred at room temperature for 30 minutes. The reaction mixture was concentrated under reduced pressure, and to the resulting residue were added DMSO (46.8 mL) and lithium acetate dihydrate (2.56 g, 25.1 mmol, 10 equivalents), and the reaction mixture was stirred at 120° C. for 4 hours. The reaction mixture was cooled to room temperature, and then to the reaction mixture was added water, and the mixture was extracted with ethyl acetate. The combined organic layers were washed with water and a saturated aqueous sodium chloride solution. The organic layers were dried over magnesium sulfate, filtered, and then concentrated under reduced pressure. The resulting residue was purified with silica gel column chromatography (silica gel, 50%-83% ethyl acetate/n-heptane, 5% methanol/ethyl acetate) to afford the title compound (588 mg).

$^1$H-NMR (400 MHz, CDCl$_3$) δ (ppm): 4.69 (s, 2H), 4.94 (s, 2H), 5.08 (s, 2H), 6.75 (d, J=9.8 Hz, 1H), 7.27-7.42 (m, 12H), 7.60 (d, J=9.4 Hz, 1H), 8.25 (dd, J=4.7, 1.6 Hz, 1H), 8.67 (s, 2H), 9.23 (s, 1H).

MS [M+H]$^+$=521

(4) Synthesis of benzyl ((3-(benzyloxy)-5'-bromo-6'-oxo-1'-(pyrimidin-5-yl)-1',6'-dihydro-[2,3'-bipyridin]-2'-yl)methyl)carbonate To a solution of benzyl ((3-(benzyloxy)-6'-oxo-1'-(pyrimidin-5-yl)-1',6'-dihydro-[2,3'-bipyridin]-2'-yl)methyl)carbonate (560 mg, 1.08 mmol, 1 equivalent) in DMF (5.00 mL) was added NBS (287 mg, 1.61 mmol, 1.5 equivalents) at room temperature, and the mixture was stirred at room temperature for 18 hours. To the reaction mixture was added water, and the mixture was extracted with ethyl acetate. The combined organic layers were washed with water and a saturated aqueous sodium chloride solution. The organic layers were dried over magnesium sulfate, filtered, and then concentrated under reduced pressure. The resulting residue was purified with silica gel column chromatography (silica gel, 50%-77% ethyl acetate/n-heptane) to afford the title compound (595 mg).

$^1$H-NMR (400 MHz, CDCl$_3$) δ (ppm): 4.66 (s, 2H), 4.93 (s, 2H), 5.08 (s, 2H), 7.26-7.42 (m, 12H), 8.03 (s, 1H), 8.25 (dd, J=4.5, 1.4 Hz, 1H), 8.64 (s, 2H), 9.23 (s, 1H).

MS [M+H]$^+$=599, 601

(5) Synthesis of benzyl ((3-(benzyloxy)-5'-(2-cyano-3-fluorophenyl)-6'-oxo-1'-(pyrimidin-5-yl)-1',6'-dihydro-[2,3'-bipyridin]-2'-yl)methyl)carbonate A mixture of benzyl ((3-(benzyloxy)-5'-bromo-6'-oxo-1'-(pyrimidin-5-yl)-1',6'-dihydro-[2,3'-bipyridin]-2'-yl)methyl)carbonate (590 mg, 0.984 mmol, 1 equivalent), 2-cyano-3-fluorophenylboronic acid pinacol ester (CAS No. 765916-91-4) (365 mg, 1.48 mmol, 1.5 equivalents), (Ataphos)$_2$PdCl$_2$ (34.8 mg, 0.049 mmol, 0.05 equivalents), potassium fluoride (172 mg, 2.95 mmol, 3 equivalents), 1,4-dioxane (15.0 mL) and water (3.0 mL) was reacted in a microwave reactor at 120° C. for 30 minutes. To the reaction mixture was added water, and the mixture was extracted with ethyl acetate. The combined organic layers were washed with water and a saturated aqueous sodium chloride solution. The organic layers were dried over magnesium sulfate, filtered, and then concentrated under reduced pressure. The resulting residue was purified with silica gel column chromatography (silica gel, 50%-83% ethyl acetate/n-heptane) to afford the title compound (511 mg).

$^1$H-NMR (400 MHz, CDCl$_3$) δ (ppm): 4.76 (s, 2H), 4.96 (s, 2H), 5.13 (s, 2H), 7.21 (t, J=8.6 Hz, 1H), 7.27-7.37 (m, 13H), 7.57 (td, J=8.2, 5.9 Hz, 1H), 7.83 (s, 1H), 8.23 (dd, J=4.7, 1.2 Hz, 1H), 8.73 (s, 2H), 9.24 (s, 1H).

MS [M+H]$^+$=640

(6) Synthesis of 2-fluoro-6-(3-hydroxy-2'-(hydroxymethyl)-6'-oxo-1'-(pyrimidin-5-yl)-1',6'-dihydro-[2,3'-bipyridin]-5'-yl)benzonitrile A mixture of benzyl ((3-(benzyloxy)-5'-(2-cyano-3-fluorophenyl)-6'-oxo-1'-(pyrimidin-5-yl)-1',6'-dihydro-[2,3'-bipyridin]-2'-yl)methyl)carbonate (505 mg, 0.79 mmol, 1 equivalent), 5% palladium on carbon (84.0 mg, 0.039 mmol, 0.05 equivalents) and ethanol (20.0 mL) was stirred vigorously at room temperature under a hydrogen atmosphere for 6 hours. The reaction mixture was purged with nitrogen, and then filtered. The resulting filtrate was concentrated under reduced pressure to afford the title compound (311 mg).

MS [M+H]$^+$=416

(7) Synthesis of 2-fluoro-6-(8-oxo-7-(pyrimidin-5-yl)-7,8-dihydro-6H-pyrano[3,2-b:5,4-b']dipyridin-9-yl)benzonitrile To a mixture of 2-fluoro-6-(3-hydroxy-2'-(hydroxymethyl)-6'-oxo-1'-(pyrimidin-5-yl)-1',6'-dihydro-[2,3-bipyridin]-5'-yl)benzonitrile (311 mg, 0.749 mmol, 1 equivalent), triphenylphosphine (295 mg, 1.12 mmol, 1.5 equivalents) and THF (10.0 mL) was slowly added DMEAD (263 mg, 1.12 mmol, 1.5 equivalents) at room temperature, and the mixture was stirred for 10 minutes. To the reaction mixture was added water, and the mixture was extracted with ethyl acetate. The combined organic layers were washed with water and a saturated aqueous sodium chloride solution. The organic layers were dried over magnesium sulfate, filtered, and then concentrated under reduced pressure. The resulting residue was purified with silica gel column chromatography (silica gel, 25%-63% ethyl acetate/n-heptane) to afford the title compound (110 mg).

$^1$H-NMR (400 MHz, CDCl$_3$) δ (ppm): 4.82 (s, 2H), 7.12-7.17 (m, 1H), 7.19-7.23 (m, 1H), 7.24-7.26 (m, 1H), 7.44 (d, J=7.8 Hz, 1H), 7.65 (td, J=8.1, 5.7 Hz, 1H), 8.27 (dd, J=4.5, 1.4 Hz, 1H), 8.59 (s, 1H), 8.81 (s, 2H), 9.39 (s, 1H).

MS [M+H]$^+$=398

Example 19

Synthesis of 3,6-difluoro-2-(8-oxo-7-(pyridin-3-yl)-7,8-dihydro-6H-pyrano[3,2-b:5,4-b']dipyridin-9-yl)benzonitrile

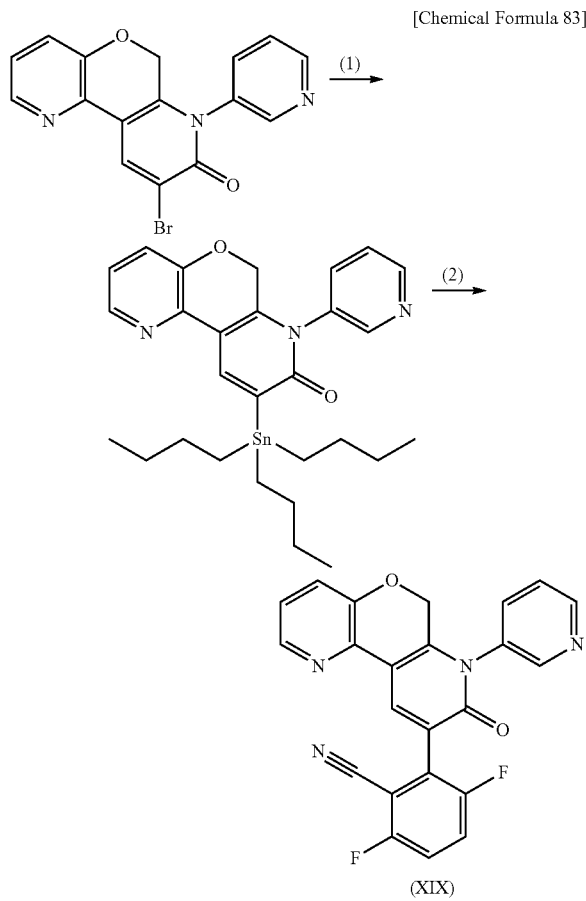

[Chemical Formula 83]

(XIX)

(1) Synthesis of 7-(pyridin-3-yl)-9-(tributylstannyl)-6H-pyrano[3,2-b;5,4-b']dipyridin-8(7H)-one A mixture of 9-bromo-7-(pyridin-3-yl)-6H-pyrano[3,2-b:5,4-b']dipyridin-8(7H)-one obtained in Production Example 2 (50 mg, 0.14 mmol, 1 equivalent), hexa-n-butylditin (0.1 mL, 0.20 mmol, 1.42 equivalents), Pd(PPh$_3$)$_4$ (10 mg, 8.65 μmol, 0.062 equivalents) and 1,4-dioxane (1.5 mL) was reacted in a microwave reactor at 150° C. for 10 minutes. The reaction mixture was allowed to return to room temperature, then hexa-n-butylditin (0.1 mL, 0.20 mmol, 1.42 equivalents) and Pd(PPh$_3$)$_4$ (10 mg, 8.65 μmol, 0.062 equivalents) were added, and the mixture was reacted again in a microwave reactor at 160° C. for 1 hour. The reaction mixture was allowed to return to room temperature, and then directly purified with silica gel column chromatography (silica gel, 0%-60% ethyl acetate/n-heptane) to afford the title compound (56 mg).

$^1$H-NMR (400 MHz, CDCl$_3$) δ (ppm): 0.86-0.93 (m, 9H), 1.03-1.23 (m, 6H), 1.31-138 (m, 6H), 1.49-1.55 (m, 3H), 1.60-1.70 (m, 3H), 4.59-4.68 (m, 1H), 4.74-4.83 (m, 1H), 7.05-7.11 (m, 1H), 7.11-7.17 (m, 1H), 7.51 (dd, J=8.1, 4.8 Hz, 1H), 7.68 (dt, J=8.1, 2.0 Hz, 1H), 8.27 (dd, J=4.6, 1.7 Hz, 1H), 8.44 (s, 1H), 8.51 (d, J=2.6 Hz, 1H), 8.74 (dd, J=4.8, 1.5 Hz, 1H).

(2) Synthesis of 3,6-difluoro-2-(8-oxo-7-(pyridin-3-yl)-7,8-dihydro-6H-pyrano[3,2-b:5,4-b']dipyridin-9-yl)benzonitrile A mixture of 7-(pyridin-3-yl)-9-(tributylstannyl)-6H-pyrano[3,2-b:5,4-b']dipyridin-8(7H)-one (40 mg, 0.071 mmol, 1 equivalent), 2-bromo-3,6-difluorobenzonitrile (US 20150126449 A1, p. 60) (CAS No, 1502090-29-0) (18.5 mg, 0.085 mmol, 1.2 equivalents), copper(I) iodide (2.69 mg, 0.014 mmol, 0.2 equivalents), Pd(PPh$_3$)$_4$ (8.16 mg, 7.06 μmol, 0.1 equivalents) and 1,4-dioxane (1.5 mL) was reacted in a microwave reactor at 160° C. for 1 hour. The reaction mixture was allowed to return to room temperature, and then directly purified with silica gel column chromatography (NH silica gel, 2%-65% ethyl acetate/n-heptane) to afford the title compound (16.8 mg).

$^1$H-NMR (400 MHz, CDCl$_3$) δ (ppm): 4.69-4.80 (m, 1H), 4.88 (t, J=15.4 Hz, 1H), 7.10-7.15 (m, 1H), 7.19 (d, J=8.4 Hz, 1H), 7.20-7.26 (m, 1H), 7.34-7.44 (m, 1H), 7.51-7.61 (m, 1H), 7.71-7.85 (m, 1H), 8.25 (dd, J=4.6, 1.3 Hz, 1H), 8.53-8.70 (m, 2H), 8.74-8.88 (m, 1H).

MS [M+H]$^+$=415

Example 20

Synthesis of 2-(7-(5-chloropyridin-3-yl)-8-oxo-7,8-dihydro-6H-pyrano[3,2-b:5,4-b']dipyridin-9-yl)-6-fluorobenzonitrile

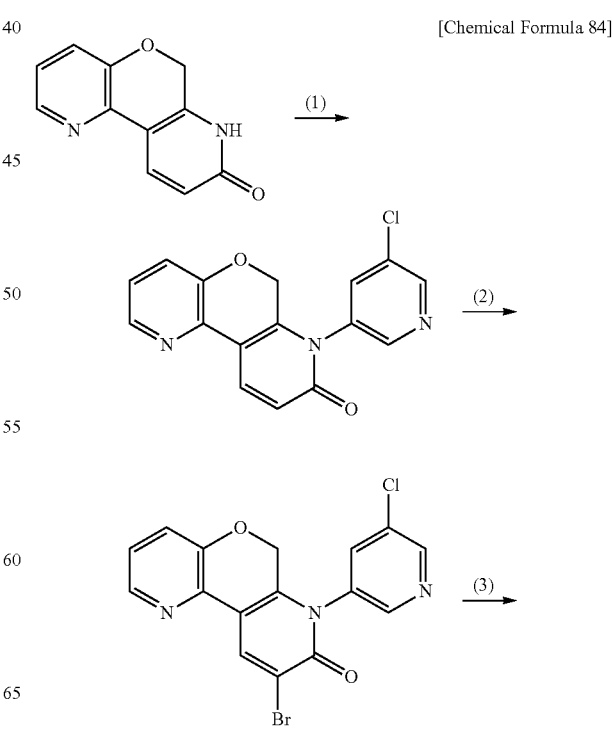

[Chemical Formula 84]

-continued

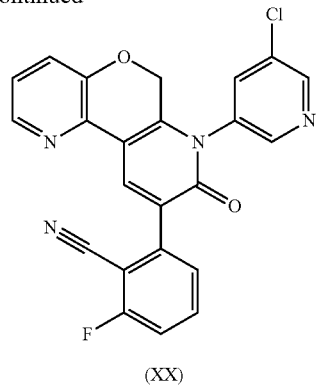

(XX)

(1) Synthesis of 7-(5-chloropyridin-3-yl)-6H-pyrano[3,2-b:5,4-b']dipyridin-8(7H)-one To a mixture of 6H-pyrano[3,2-b:5,4-b']dipyridin-8(7H)-one obtained in Production Example 1 (200 mg, 0.999 mmol, 1 equivalent), silver carbonate (413 mg, 1.50 mmol, 1.5 equivalents), copper(I) iodide (114 mg, 0.599 mmol, 0.6 equivalents), pyridine (0.808 mL, 9.99 mmol, 10 equivalents) and DMF (5 mL) was slowly added a suspension of 5-chloropyridine-3-boronic acid (CAS No. 872041-85-5) (393 mg, 2.50 mmol, 2.5 equivalents) in DMF (1 mL) at 80° C. The reaction mixture was stirred at 80° C. for 24 hours. The reaction mixture was cooled down to room temperature, and ethyl acetate was added. The mixture was filtered through Celite™, and the residue was washed with ethyl acetate. The resulting filtrate was concentrated under reduced pressure. The residue was purified with silica gel column chromatography (silica gel, 60%-100% ethyl acetate/n-heptane) to afford the title compound (20 mg).

$^1$H-NMR (400 MHz, CDCl$_3$) δ (ppm): 4.68 (d, J=16.0 Hz, 1H), 4.79 (d, J=16.0 Hz, 1H), 6.77 (d, J=10.2 Hz, 1H), 7.06-7.13 (m, 1H), 7.14-7.21 (m, 1H), 7.72 (t, J=2.0 Hz, 1H), 8.26 (dd, J=4.5, 1.0 Hz, 1H), 8.35 (d, J=9.4 Hz, 1H), 8.42 (d, J=2.0 Hz, 1H), 8.75 (d, J=2.3 Hz, 1H).

MS [M+H]$^+$=312

(2) Synthesis of 9-bromo-7-(5-chloropyridin-3-yl)-6H-pyrano[3,2-b:5,4-b']dipyridin-8(7H)-one 7-(5-Chloropyridin-3-yl)-6H-pyrano[3,2-b:5,4-b']dipyridin-8(7H)-one (20 mg, 0.064 mmol, 1 equivalent) was dissolved in DMF (1 mL), and NBS (12.6 mg, 0.071 mmol, 1.1 equivalents) was added, and the mixture was stirred at room temperature for 3 hours. The reaction mixture was directly purified with silica gel column chromatography (silica gel, 50%-80% ethyl acetate/n-heptane) to afford the title compound (12 mg).

$^1$H-NMR (400 MHz, CDCl$_3$) δ (ppm): 4.65 (d, J=15.6 Hz, 1H), 4.77 (d, J=15.6 Hz, 1H), 7.06-7.22 (m, 2H), 7.68-7.78 (m, 1H), 8.26 (dd, J=4.7, 1.6 Hz, 1H), 8.42 (d, J=2.0 Hz, 1H), 8.72-8.84 (m, 2H).

MS [M+H]$^+$=390

(3) Synthesis of 2-(7-(5-chloropyridin-3-yl)-8-oxo-7,8-dihydro-6H-pyrano[3,2-b']dipyridin-9-yl)-6-fluorobenzonitrile A mixture of 9-bromo-7-(5-chloropyridin-3-yl)-6H-pyrano[3,2-b:5,4-b']dipyridin-8(7H)-one (6.5 mg, 0.017 mmol, 1 equivalent), 2-cyano-3-fluorophenylboronic acid pinacol ester (CAS No. 765916-91-4) (6.17 mg, 0.025 mmol, 1.5 equivalents), (Ataphos)$_2$PdCl$_2$ (0.59 mg, 0.832 μmol, 0.05 equivalents), potassium fluoride (2.90 mg, 0.050 mmol, 3 equivalents), water (0.15 mL) and 1,4-dioxane (1.5 mL) was reacted in a microwave reactor at 150° C. for 10 minutes. The reaction mixture was concentrated under reduced pressure. The residue was purified with silica gel column chromatography (silica gel, 60%-90% ethyl acetate/n-heptane) to afford the title compound (2.4 mg).

$^1$H-NMR (400 MHz, CDCl$_3$) δ (ppm): 4.77 (d, J=15.6 Hz, 1H), 4.88 (d, J=15.6 Hz, 1H), 7.05-7.17 (m, 1H), 7.18-7.30 (m, 2H), 7.44 (d, J=7.8 Hz, 1H), 7.64 (td, J=8.1, 5.7 Hz, 1H), 7.81 (t, J=2.1 Hz, 1H), 8.26 (dd, J=4.7, 1.2 Hz, 1H), 8.49 (d, J=2.3 Hz, 1H), 8.57 (s, 1H), 8.77 (d, J=2.0 Hz, 1H).

MS [M+H]$^+$=431

Example 21

Synthesis of 2-fluoro-6-(7-(2-methylpyrimidin-5-yl)-8-oxo-7,8-dihydro-6H-pyrano[3,2-b:5,4-b']dipyridin-9-yl)benzonitrile

[Chemical Formula 85]

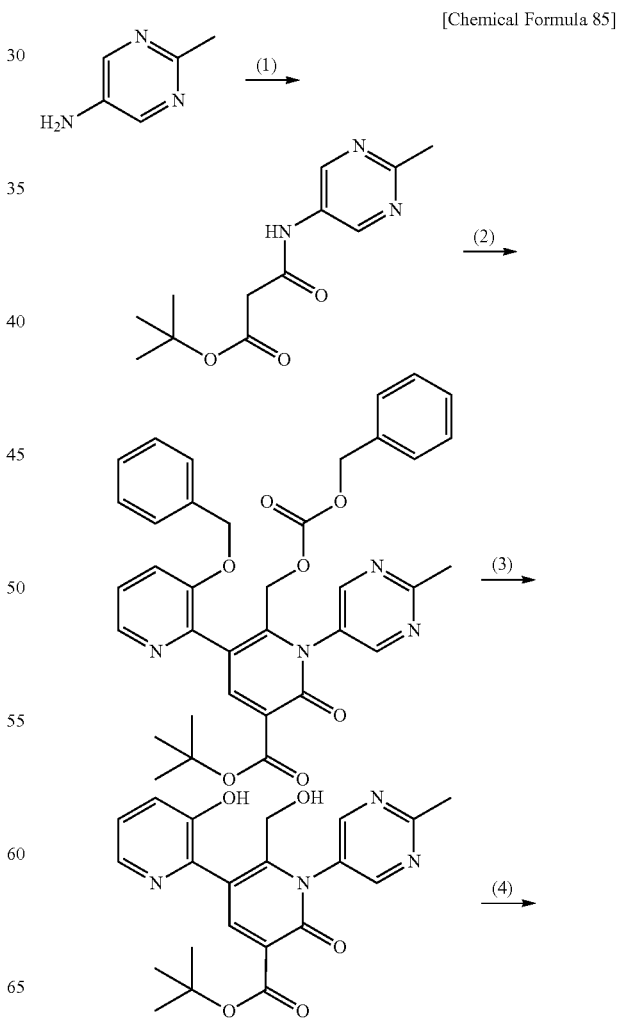

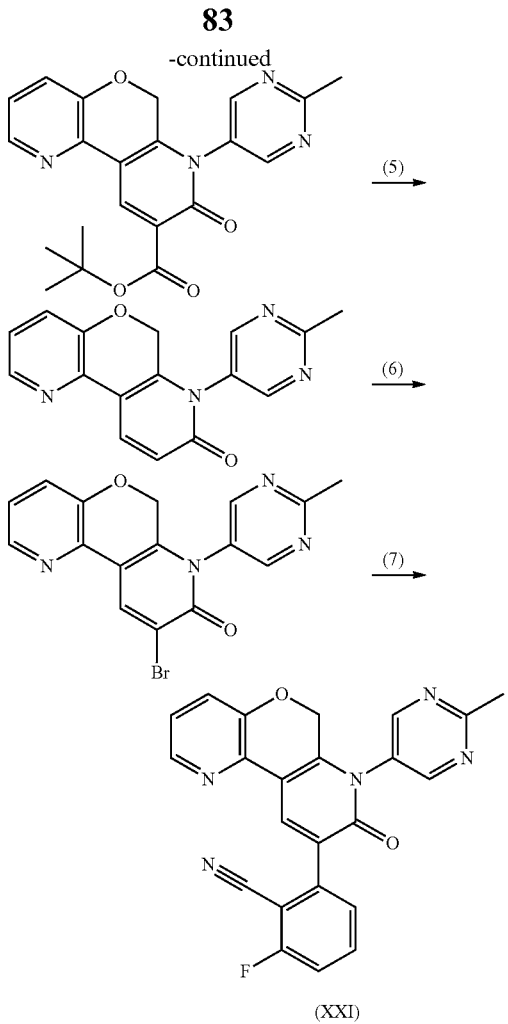

(XXI)

(1) Synthesis of t-butyl 3-((2-methylpyrimidin-5-yl)amino)-3-oxopronanoate

A mixture of 3-(t-butoxy)-3-oxopropionic acid (CAS No, 40052-13-9) (1.61 g, 10.1 mmol, 1.1 equivalents), 2-methyl-5-pyrimidinamine (CAS No. 39889-94-6) (1.00 g, 9.16 mmol, 1.0 equivalent), triethylamine (1.53 mL, 11.0 mmol, 1.2 equivalents), EDC (2.11 g, 11.0 mmol, 1.2 equivalents) and DCM (20 mL) was heated to reflux for 1 hour. The reaction mixture was cooled down to room temperature, then a saturated aqueous sodium hydrogen carbonate solution was added, and the mixture was extracted with DCM. The organic layer was concentrated under reduced pressure. The residue was purified with silica gel column chromatography (silica gel, 50%-100% ethyl acetate/n-heptane) to afford the title compound (2.21 g).

$^1$H-NMR (400 MHz, CDCl$_3$) δ (ppm): 1.53 (s, 9H), 2.72 (s, 3H), 3.43 (s, 2H), 8.91 (s, 2H), 9.64 (br. s, 1H).

(2) Synthesis of t-butyl 3-(benzyloxy)-2'-((((benzyloxy)carbonyl)oxy)methyl)-1'-(2-methylpyrimidin-5-yl)-6'-oxo-1',6'-dihydro-[2,3'-bipyridine]-5'-carboxylate A mixture of t-butyl 3-((2-methylpyrimidin-5-yl)amino)-3-oxopropanoate (313 mg, 1.25 mmol, 1.2 equivalents), lithium bromide (180 mg, 2.08 mmol, 2.0 equivalents), benzyl (3-(3-(benzyloxy)pyridin-2-yl)-4-methoxy-2-oxobut-3-en-1-yl)carbonate (E/Z mixture) obtained in Production Example 9 (450 mg, 1.04 mmol, 1.0 equivalents), triethylamine (0.506 mL, 3.63 mmol, 3.5 equivalents) and propionitrile (5.00 mL) was stirred at room temperature for 10 minutes. The reaction mixture was directly purified with silica gel column chromatography (silica gel, 40%-100% ethyl acetate/n-heptane) to afford the title compound (480 mg).

MS m/z=636 (3) Synthesis of t-butyl 3-hydroxy-2'-(hydroxymethyl)-1'-(2-methylpyrimidin-5-yl)-6'-oxo-1',6'-dihydro-[2,3'-bipyridine]-5'-carboxylate A mixture of t-butyl 3-(benzyloxy)-2'-((((benzyloxy)carbonyl)oxy)methyl)-1'-(2-methylpyrimidin-5-yl)-6'-oxo-1',6'-dihydro-[2,3'-bipyridine]-5'-carboxylate (480 mg, 0.756 mmol, 1.0 equivalents), 10% palladium on carbon (water content, 53.9%) (80.0 mg, 0.035 mmol, 0.046 equivalents) and methanol (3.00 mL) was stirred at room temperature under a hydrogen atmosphere for 40 minutes. The reaction mixture was filtered through Celite™, and the residue was washed with ethyl acetate. The resulting filtrate was concentrated under reduced pressure. The residue was purified with silica gel column chromatography (silica gel, 0%-20% methanol/ethyl acetate) to afford the title compound (250 mg).

MS [M+H]$^+$=411

(4) Synthesis of t-butyl 7-(2-methylpyrimidin-5-yl)-8-oxo-7,8-dihydro-6H-pyrano[3,2-b]dipyridine-9-carboxylate To a mixture of t-butyl 3-hydroxy-2'-(hydroxymethyl)-1'-(2-methylpyrimidin-5-yl)-6'-oxo-1',6'-dihydro-[2,3'-bipyridine]-5'-carboxylate (250 mg, 0.609 mmol, 1.0 equivalents), triphenylphosphine (224 mg, 0.853 mmol, 1.4 equivalents) and THF (3.00 mL) was added a solution of DMEAD (200 mg, 0.853 mmol, 1.4 equivalents) in THF (1.00 mL) at 0° C. After the progress of the reaction mixture was confirmed, the reaction mixture was concentrated under reduced pressure to about one half of the original solution volume. The residue was purified with silica gel column chromatography (silica gel, 40%-100% ethyl acetate/n-heptane) to afford the title compound (239 mg).

MS [M+H]$^+$=393

(5) Synthesis of 7-(2-methylpyrimidin-5-yl)-6H-pyrano[3,2-b:5,4-b']dipyridin-8(7H)-one To t-butyl 7-(2-methylpyrimidin-5-yl)-8-oxo-7,8-dihydro-6H-pyrano[3,2-b:5,4-b']dipyridine-9-carboxylate (239 mg, 0.609 mmol, 1.0 equivalent) was added TFA (3.00 mL), and the reaction mixture was concentrated under reduced pressure. To the resulting residue were added DMSO (3.00 mL) and lithium acetate dihydrate (311 mg, 3.05 mmol, 5.0 equivalents), and the reaction mixture was stirred at 120° C. for 30 minutes. To the reaction mixture was added a 10% aqueous sodium chloride solution, and the mixture was extracted with ethyl acetate. The organic layer was dried over magnesium sulfate, filtered, and then concentrated under reduced pressure. The resulting residue was purified with silica gel column chromatography (NH silica gel, 60%-80% ethyl acetate/n-heptane). The resulting crude product was purified again with silica gel column chromatography (silica gel, 0%-15% methanol/ethyl acetate) to afford the title compound (34.0 mg).

MS [M+H]$^+$=293

(6) Synthesis of 9-bromo-7-(2-methylpyrimidin-5-yl)-6H-pyrano[3,2-b:5,4-b']dipyridin-8(7H)-one A mixture of 7-(2-methylpyrimidin-5-yl)-6H-pyrano[3,2-b:5,4-b']dipyridin-8(7H)-one (34.0 mg, 0.116 mmol, 1.0 equivalent), NBS (31.1 mg, 0.174 mmol, 1.5 equivalents) and DMF (3.00 mL) was stirred at 50° C. for 30 minutes. The reaction mixture was concentrated under reduced pressure. The resulting residue was purified with silica gel column chromatography (silica gel, 0%-25% methanol/ethyl acetate) to afford the title compound (22.0 mg).

MS [M+H]$^+$=371

(7) Synthesis of 2-fluoro-6-(7-(2-methylpyrimidin-5-yl)-8-oxo-7,8-dihydro-6H-pyrano[3,2-b:5,4-b']dipyridin-9-yl)benzonitrile A mixture of 9-bromo-7-(2-methylpyrimidin-5-yl)-6H-pyrano[3,2-b:5,4-b']dipyridin-8(7H)-one (22.0 mg, 0.059 mmol, 1.0 equivalent), 2-cyano-3-fluorophenylboronic acid pinacol ester (CAS No. 765916-91-4) (22.0 mg, 0.089 mmol, 1.5 equivalents), (Ataphos)$_2$PdCl$_2$ (4.20 mg, 5.93 µmol, 0.1 equivalents), potassium fluoride (10.3 mg, 0.178 mmol, 3.0 equivalents), 1,4-dioxane (0.8 mL) and water (0.4 mL) was reacted in a microwave reactor at 140° C. for 10 minutes. The reaction mixture was directly purified with silica gel column chromatography (silica gel, 80%-100% ethyl acetate/n-heptane). The resulting crude product was purified again with silica gel column chromatography (NH silica gel, 50%-80% ethyl acetate/n-heptane) to afford the title compound (11.5 mg).

$^1$H-NMR (400 MHz, CDCl$_3$) δ (ppm): 2.88 (s, 3H), 4.84 (s, 2H), 7.08-7.32 (m, 3H), 7.44 (d, J=7.7 Hz, 1H), 7.64 (td, J=8.1, 5.5 Hz, 1H), 8.26 (dd, J=4.8, 1.5 Hz, 1H), 8.58 (s, 1H), 8.68 (s, 2H).

MS [M+H]$^+$=412

Example 22

Synthesis of 9-(3-fluoro-2-methylphenyl)-7-(pyridin-3-yl)-6H-pyrano[3,2-b:5,4-b']dipyridin-8(7H)-one

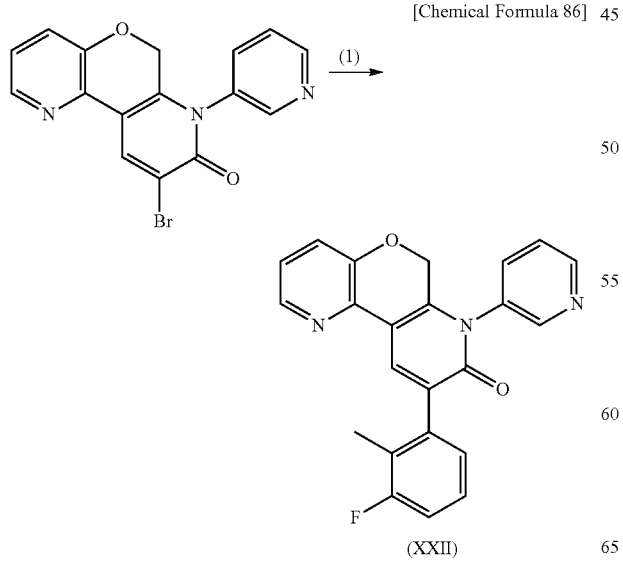

(1) Synthesis of 9-(3-fluoro-2-methylphenyl)-7-(pyridin-3-yl)-6H-pyrano[3,2-b:5,4-b']dipyridin-8(7H)-one A mixture of 9-bromo-7-(pyridin-3-yl)-6H-pyrano[3,2-b:5,4-b']dipyridin-8(7H)-one obtained in Production Example 2 (10.7 mg, 0.03 mmol, 1 equivalent), (3-fluoro-2-methylphenyl)boronic acid (CAS No. 163517-61-1) (6.94 mg, 0.045 mmol, 1.5 equivalents), (Ataphos)$_2$PdCl$_2$ (1.06 mg, 1.50 µmol, 0.05 equivalents), potassium fluoride (5.24 mg, 0.09 mmol, 3 equivalents), 1,4-dioxane (0.4 mL) and water (0.1 mL) was reacted in a microwave reactor at 120° C. for 30 minutes. The reaction mixture was directly purified with silica gel column chromatography (NH silica gel, 5%-67% ethyl acetate/n-heptane) to afford the title compound (10 mg).

$^1$H-NMR (400 MHz, CDCl$_3$) δ (ppm): 2.20 (d, J=2.3 Hz, 3H), 4.69-4.75 (m, 1H), 4.82-4.89 (m, 1H), 7.00-7.07 (m, 1H), 7.08-7.14 (m, 2H), 7.15-7.23 (m, 2H), 7.54 (dd, J=8.0, 4.9 Hz, 1H), 7.69-7.79 (m, 1H), 8.24 (dd, J=4.7, 1.6 Hz, 1H), 8.35 (s, 1H), 8.58 (d, J=2.3 Hz, 1H), 8.78 (dd, J=4.7, 1.6 Hz, 1H).

MS [M'H]$^+$=386

Referential Example 1

Synthesis of 9-(2,6-difluorophenyl)-7-(pyridin-3-yl)-6H-pyrano[3,2-b:5,4-b']dipyridin-8(7H)-one

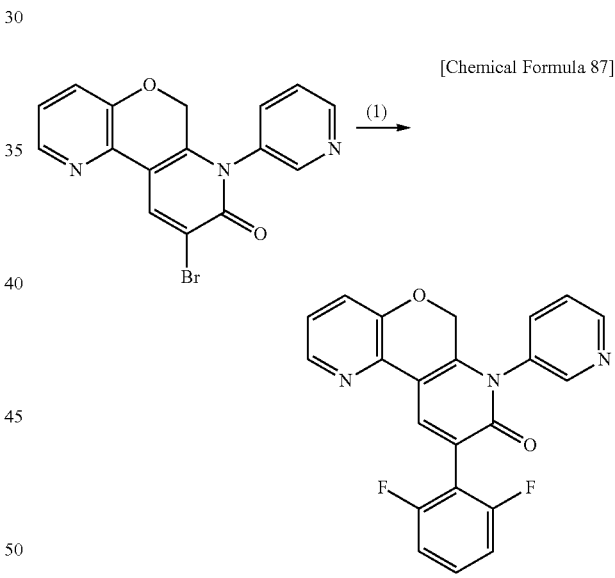

(1) Synthesis of 9-(2,6-difluorophenyl)-7-(pyridin-3-yl)-6H-pyrano[3,2-b:5,4-b']dipyridin-8(7H)-one A mixture of 9-bromo-7-(pyridin-3-yl)-6H-pyrano[3,2-b:5,4-b']dipyridin-8(7H)-one obtained in Production Example 2 (100 mg, 0.281 mmol, 1 equivalent), tributyl(2,6-difluorophenyl)stannane obtained in Production Example 5 (147 mg, 0.365 mmol, 1.3 equivalents), (Ataphos)$_2$PdCl$_2$ (9.94 mg, 0.014 mmol, 0.05 equivalents), copper(I) iodide (5.35 mg, 0.028 mmol, 0.1 equivalents) and 1,4-dioxane (3 mL) was reacted in a microwave reactor at 150° C. for 7 hours. The reaction mixture was directly purified with silica gel column chromatography (NH silica gel on silica gel, 5%-95% ethyl acetate/n-heptane). The resulting crude product was triturated with a mixed solution of ethanol-n-heptane (1:4), and the precipitate was collected by filtration. The resulting solid was washed with n-heptane to afford the title compound (41.5 mg).

$^1$H-NMR (400 MHz, CDCl$_3$) δ (ppm): 4.69-4.77 (m, 1H), 4.83-4.91 (m, 1H), 6.93-7.01 (m, 2H), 7.08-7.14 (m, 1H), 7.15-7.19 (m, 1H), 7.28-7.38 (m, 1H), 7.51-7.57 (m, 1H), 7.73-7.79 (m, 1H), 8.25 (dd, J=4.6, 1.5 Hz, 1H), 8.49 (s, 1H), 8.60 (d, J=2.4 Hz, 1H), 8.78 (dd, J=4.8, 1.5 Hz, 1H).

MS [M+H]$^+$=390

Control Compound

Synthesis of 2-(3-oxo-4-(pyridin-3-yl)-3,5-dihydro-2H-chromeno[4,3-c]pyridazin-2-yl)benzonitrile

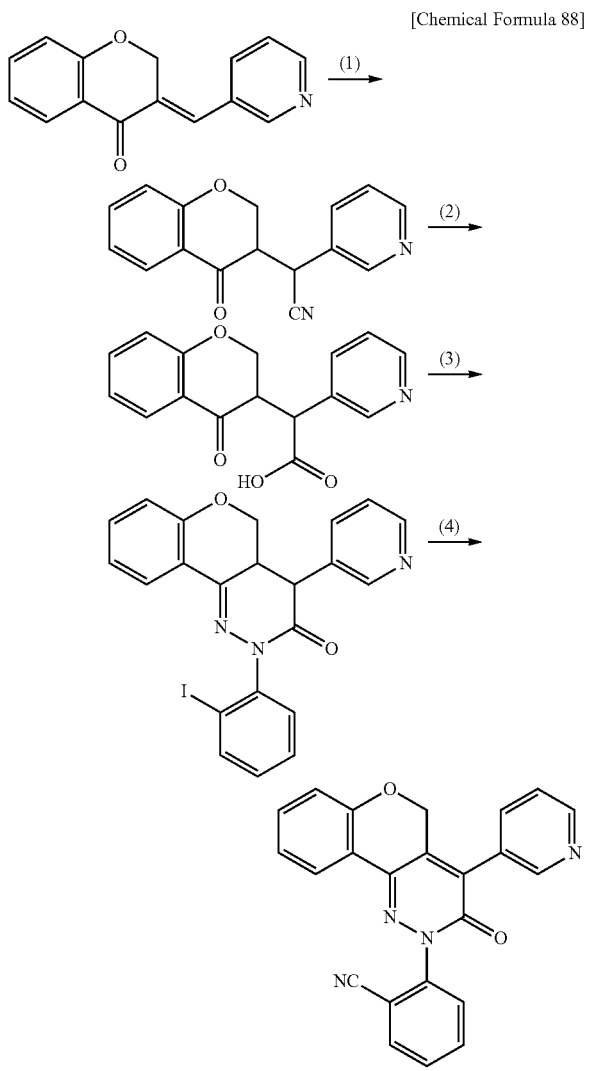

[Chemical Formula 88]

(1) Synthesis of 2-(4-oxochroman-3-yl)-2-(pyridin-3-yl)acetonitrile

Into a solution of 3-(pyridin-3-ylmethylene)chroman-4-one (European Journal of Medicinal Chemistry, 2011, 46, 3201-3209) (4.74 g, 20.0 mmol, 1 equivalent) in DMF (67 mL) were added a solution of potassium cyanide (2.60 g, 39.9 mmol, 2 equivalents) and ammonium chloride (1.78 g, 33.3 mmol, 1.67 equivalents) in water (20 mL) at 0° C. over 10 minutes. The reaction mixture was stirred at the same temperature for 10 minutes, and then stirred at room temperature for 1 hour. To the reaction mixture was added water, and the mixture was extracted with diethyl ether and ethyl acetate. The combined organic layers were washed with water. The organic layers were dried over magnesium sulfate, filtered, and then concentrated under reduced pressure to afford the title compound (5.14 g).

(2) Synthesis of 2-(4-oxochroman-3-yl)-2-(pyridin-3-yl)acetic acid

A mixed solution of 2-(4-oxochroman-3-yl)-2-(pyridin-3-yl)acetonitrile (12.3 g, 46.5 mmol) in acetic acid (60 mL) and concentrated hydrochloric acid (60 mL) was heated to reflux for 3 hours. The reaction mixture was allowed to return to room temperature, and the reaction mixture was poured into ice water. The solution was neutralized using a 5 N aqueous sodium hydroxide solution, and extracted with DCM. The combined organic layers were dried over magnesium sulfate, filtered, and then concentrated under reduced pressure to afford the title compound (4.2 g).

(3) Synthesis of 2-(2-iodophenyl)-4-(pyridin-3-yl)-4a,5-dihydro-2H-chromeno[4,3-c]pyridazin-3(4H)-one To (2-iodophenyl)hydrazine hydrochloride (Journal of Medicinal Chemistry, 1988, 31 (9), 1712-1719) (4.01 g, 14.8 mmol, 1 equivalent) was added a 1 N aqueous sodium hydroxide solution, and the mixture was extracted with DCM. The combined organic layers were concentrated to prepare (2-iodophenyl)hydrazine. A solution of the above (2-iodophenyl)hydrazine and 2-(4-oxochroman-3-yl)-2-(pyridin-3-yl)acetic acid (4.20 g, 14.8 mmol, 1 equivalent) in n-butanol was heated at 110° C. for 5 hours. The reaction mixture was concentrated under reduced pressure. To a solution of the resulting residue in ethanol (30 mL) were added para-toluenesulfonic acid monohydrate (10 mg) and (2-iodophenyl)hydrazine prepared by the above method (1 equivalent), and the mixture was heated at 90° C. overnight. The reaction mixture was concentrated under reduced pressure. A solution of the resulting residue in acetic acid was heated at 90° C. for 2 hours. The reaction mixture was concentrated under reduced pressure. To the residue was added ethyl acetate, and the mixture was washed sequentially with a saturated aqueous sodium hydrogen carbonate solution, water and a saturated aqueous sodium chloride solution. The organic layer was dried over magnesium sulfate, filtered, and then concentrated under reduced pressure. The residue was purified with silica gel column chromatography to afford the title compound (1.15 g), $^1$H-NMR (400 MHz, CDCl$_3$) δ (ppm): 3.61-3.84 (m, 2H), 3.95-4.09 (m, 2H), 6.92 (d, J=8.4 Hz, 1H), 6.96-7.04 (m, 1H), 7.08-7.18 (m, 1H), 7.29-7.36 (m, 1H), 7.39 (dd, J=7.6, 4.9 Hz, 1H), 7.43-7.56 (m, 2H), 7.70 (br. s, 1H), 7.89-8.03 (m, 2H), 8.54 (d, J=1.6 Hz, 1H), 8.63 (dd, J=4.7, 1.6 Hz, 1H).

MS [M+H]$^+$=482

(4) Synthesis of 2-(3-oxo-4-(pyridin-3-yl)-3,5-dihydro-2H-chromeno[4,3-c]pyridazin-2-yl)benzonitrile A mixed solution of 2-(2-iodophenyl)-4-(pyridin-3-yl)-4a,5-dihydro-2H-chromeno[4,3-c]pyridazin-3(4H)-one (50 mg, 0.104 mmol, 1 equivalent), zinc(II) cyanide (40 mg, 0.341 mmol, 3.28 equivalents), Pd(PPh$_3$)$_4$ (5 mg, 4.33 µmol, 0.042 equivalents) and NMP (1.5 mL) was reacted in a microwave reactor at 100° C. for 1 hour and at 120° C. for 3 hours. To the reaction mixture was added water, and the mixture was extracted with ethyl acetate. The combined organic layers were washed with water and a saturated aqueous sodium chloride solution. The organic layers were dried over sodium sulfate, filtered, and then concentrated under reduced pressure. The residue was purified with silica gel column chromatography and preparative TLC to afford the title compound (6.2 mg).

$^1$H-NMR (400 MHz, DMSO-d$_6$) δ (ppm): 5.21 (s, 2H), 7.08-7.12 (m, 1H), 7.12-7.20 (m, 1H), 7.42-7.48 (m, 1H), 7.56-7.61 (m, 1H), 7.70-7.77 (m, 1H), 7.88-8.00 (m, 4H), 8.07-8.12 (m, 1H), 8.64-8.75 (m, 2H).

MS [M+Na]$^+$=401

Pharmacological Test Example

The present inventors conducted the following tests, in order to confirm the effects of the compounds of the present invention. With regard to the AMPA receptor inhibitory action of the compounds, AMPA-induced intraneuronal calcium entry-suppressing action was examined using a primary culture system of embryonic rat cerebral cortex neurons. With regard to the anticonvulsant action of the compounds, 6 Hz (44 mA) stimulation-induced convulsions known as a treatment-resistant convulsion model were used. AMPA inhibitor-induced central nervous system depressant action such as loss of coordination was evaluated using a rotarod performance test. The present inventors evaluated the safety margins of the compounds with high accuracy, by simultaneously evaluating, in the same animals, the effects of suppressing convulsive seizures of the compounds and the loss of coordination secondarily induced by the compounds.

AMPA-Induced Intraneuronal Calcium Entry-Suppressing Action

<Culture conditions> Whole fetuses were removed from the uteri of Wistar rats at embryonic day 18 (Charles River Japan) anesthetized with isoflurane. Whole brains were removed from the whole fetuses, and the cerebral cortex was separated in Leibovitz's L-15 medium or Hanks balanced salt solution containing 20% fetal bovine serum. The resulting material was treated with trypsin/DNase solution at 37° C. for 45 to 60 minutes. After the serum was added to stop the trypsin reaction, the resulting material was centrifuged at 1200 to 1500 rpm for 3 to 5 minutes. After the supernatant was removed, Neurobasal medium (containing 2% B-27 supplement and the like; hereinafter "Neurobasal medium") was added, and the cells were uniformly dispersed by gently pipetting. The cell suspension was slightly stirred, and then filtered through a nylon mesh filter. Viable cells were counted using a hemocytometer, and diluted with Neurobasal medium to 8 to 10×10$^5$ cells/mL. The cells were seeded into 96 well plates at 100 µL per well and cultured in a CO$_2$ incubator (5% CO$_2$, 37° C.). The medium was replaced after 24 hours, and neurons cultured for 7 to 21 days were used.

On the day of the assay, the medium was removed and replaced with a calcium measurement solution containing 5 to 10 µmol/L of Fura 2-AM (140 mmol/L sodium chloride, 5 mmol/L potassium chloride, 2 mmol/L magnesium chloride, 3 mmol/L calcium chloride, 24 mmol/L D(+)-glucose, 10 mmol/L HEPES, 1 µmol/L MK-801, pH 7.4), and the cells were treated in a CO$_2$ incubator (5% CO$_2$, 37° C.) for 1 to 2 hours. The calcium measurement solution containing the Fura-2 AM solution was subsequently removed, and the neurons in each well were washed twice with the calcium measurement solution for each well, and then 50 µL of the calcium measurement solution was added to each well. Subsequently, 50 µL of a test compound or medium prepared at a concentration 3-fold higher than the final concentration was added, and the cells were pre-treated for about 15 minutes. The plates were subsequently placed on the Fluorescence Drug Screening System 6000 (Hamamatsu Photonics K.K.). The cells were stimulated by adding to each well 50 µL of an AMPA stimulating solution prepared to 3.3 µmol/L with the calcium measurement solution. Changes in calcium concentration were measured as the changes in fluorescence intensity at excitation wavelengths of 340 nm and 380 nm (measurement wavelength: 540 nm). The rate of change of the intracellular calcium concentration was calculated according to the following equation:

Rate of increase of the intracellular calcium concentration (% control)=$(T_{post}-T_{pre})/(C_{post}-C_{pre})\times 100$ wherein $T_{post}$: the proportion of fluorescence of sample wells after stimulation; $T_{pre}$: the proportion of fluorescence of sample wells before stimulation; $C_{post}$: the proportion of fluorescence of control wells after stimulation; and $C_{pre}$: the proportion of fluorescence of control wells before stimulation.

The IC$_{50}$ value of the test compound for AMPA inhibition was determined from the rates of increase of the intracellular calcium concentration at various concentrations.

The results are shown in Table 1. These results revealed that the compounds of Examples 1 to 22 have sufficient AMPA receptor inhibitory action.

TABLE 1

| Example | IC$_{50}$ (nM) |
| --- | --- |
| Control Compound | 20.00 |
| Example 1 | 33.54 |
| Example 2 | 16.00 |
| Example 3 | 10.40 |
| Example 4 | 28.30 |
| Example 5 | 31.84 |
| Example 6 | 34.60 |
| Example 7 | 15.50 |
| Example 8 | 70.10 |
| Example 9 | 50.89 |
| Example 10 | 18.80 |
| Example 11 | 26.30 |
| Example 12 | 32.97 |
| Example 13 | 67.55 |
| Example 14 | 19.40 |
| Example 15 | 8.20 |
| Example 16 | <8 |
| Example 17 | 17.70 |
| Example 18 | 29.00 |
| Example 19 | 23.40 |
| Example 20 | 8.26 |
| Example 21 | 44.26 |
| Example 22 | 53.30 |
| Referential Example 1 | 44.11 |

Rotarod Performance Test-1

A rotarod (MK-660C from Muromachi Kikai Co., Ltd.) was used for the measurement. The rod (bar) was controlled to be gradually accelerated from its stationary state to a speed of 40 rotations/minute after 180 seconds. As the animals, 5 or 6-week-old male ddY mice (Japan SLC, Inc.) were used. On the day on which the test was performed, the mice were trained under the above-described measurement conditions, and mice that were able to ride on the rod for 1 minute or longer with good reproducibility were selected and subjected to the test.

Each of the compounds was dissolved in a medium (a solution prepared by adding DMSO to a 0.5% methylcellulose solution to a final concentration of 10%. As required, 0.5 to 5% of 1 mol/L hydrochloric acid and 5% Cremophor™ were added), and then orally administered to the mice in optimum four doses between 0.5 to 10 mg/kg. As the control, only the medium was orally administered. After a lapse of 25 minutes from the oral administration of each compound, the mice were subjected to the rotarod performance test. Five to twenty-five mice were used for each compound group. The time until the mice fell from the rotarod was measured for each compound, and the dose at which the time was reduced to 50% of the average value of the time of fall for the medium control group ($TD_{50}$) was calculated.

The results are shown in Table 2.

Murine 6 Hz convulsion models (Matthew E. Barton et al. "Pharmacological characterization of the 6 Hz psychomotor seizure model of partial epilepsy" *Epilepsy Research* 47 (2001) pp. 217-227)

Immediately after the rotarod performance test-1 was completed, the cornea was stimulated by passing an electrical current (6 Hz, 44 mA, 0.2-millisecond pulse, for 3 seconds) from a copper electrode moistened with physiological saline, and the presence or absence of the development of a seizure was observed. The seizure was determined by the development of akinesia, jaw and forelimb clonus, whisker tremors, and Straub tail. For each compound, the dose at which 50% of the animals develop a seizure ($ED_{50}$) was calculated.

Further, for the purpose of evaluating the safety margin of each of the compounds of the present invention, the therapeutic index ($TD_{50}/ED_{50}$) was calculated by comparing the seizure inhibitory action ($ED_{50}$) in the 6 Hz convulsion models and the neurotoxic action ($TD_{50}$) in the rotarod performance test-1.

The results are shown in Table 2. From these results, the compounds of Examples 1 to 22 are believed to have potential applicability as AMFA inhibitors that exhibit high therapeutic indices, and have reduced central nervous system depressant action, compared to the control compound.

TABLE 2

| Example | $ED_{50}$ (mg/kg, p.o.) | $TD_{50}$ (mg/kg, p.o.) | Therapeutic Index |
|---|---|---|---|
| Control Compound | 3.96 | 2.73 | 0.69 |
| Example 1 | 2.08 | 3.09 | 1.49 |
| Example 2 | 1.91 | 4.50 | 2.36 |
| Example 3 | 1.21 | 2.47 | 2.04 |
| Example 4 | 2.33 | 3.90 | 1.67 |
| Example 5 | 3.23 | 6.53 | 2.02 |
| Example 6 | 2.86 | 4.44 | 1.55 |
| Example 7 | 0.97 | 1.70 | 1.75 |
| Example 8 | 4.85 | >8 | >1.65 |
| Example 9 | 3.38 | 9.55 | 2.83 |
| Example 10 | 2.08 | 3.37 | 1.62 |
| Example 11 | 1.69 | 5.05 | 2.99 |
| Example 12 | 1.66 | 3.06 | 1.84 |
| Example 13 | 2.25 | 3.89 | 1.73 |
| Example 14 | 2.09 | 4.76 | 2.27 |
| Example 15 | 1.41 | 2.67 | 1.89 |
| Example 16 | 1.05 | 1.73 | 1.65 |
| Example 17 | 2.00 | 4.27 | 2.14 |
| Example 18 | 2.00 | 4.03 | 2.02 |
| Example 19 | 2.00 | 3.25 | 1.63 |
| Example 20 | 2.47 | 4.74 | 1.91 |
| Example 21 | 2.50 | 5.30 | 2.12 |
| Example 22 | 3.23 | 6.19 | 1.91 |
| Referential Example 1 | 1.41 | 5.16 | 3.66 |

Rotarod Performance Test-2

A rotarod (MK-660C from Muromachi Kikai Co., Ltd.) was used for the measurement. The rod (bar) was controlled to be gradually accelerated from its stationary state to a speed of 40 rotations/minute after 180 seconds. As the animals, 5 or 6-week-old male ddY mice (Japan SLC, Inc.) were used. On the day on which the test was performed, the mice were trained under the above-described measurement conditions, and mice that were able to ride on the rod for 1 minute or longer with good reproducibility were selected and subjected to the test.

Each of the compounds was dissolved in a medium (a solution prepared by adding DMSO to a 0.5% methylcellulose solution to a final concentration of 10%. As required, 0.5 to 5% of 1 mol/L hydrochloric acid and 5% Cremophor™ were added), and then orally administered to the mice at the $ED_{50}$ dose calculated using the 6 Hz convulsion models. As the control, only the medium was orally administered. After a lapse of 25 minutes from the oral administration of each compound, the mice were subjected to the rotarod performance test. Five or six mice were used for each compound group. For each compound, the time until the mice fell from the rotarod was measured.

Figure 2:
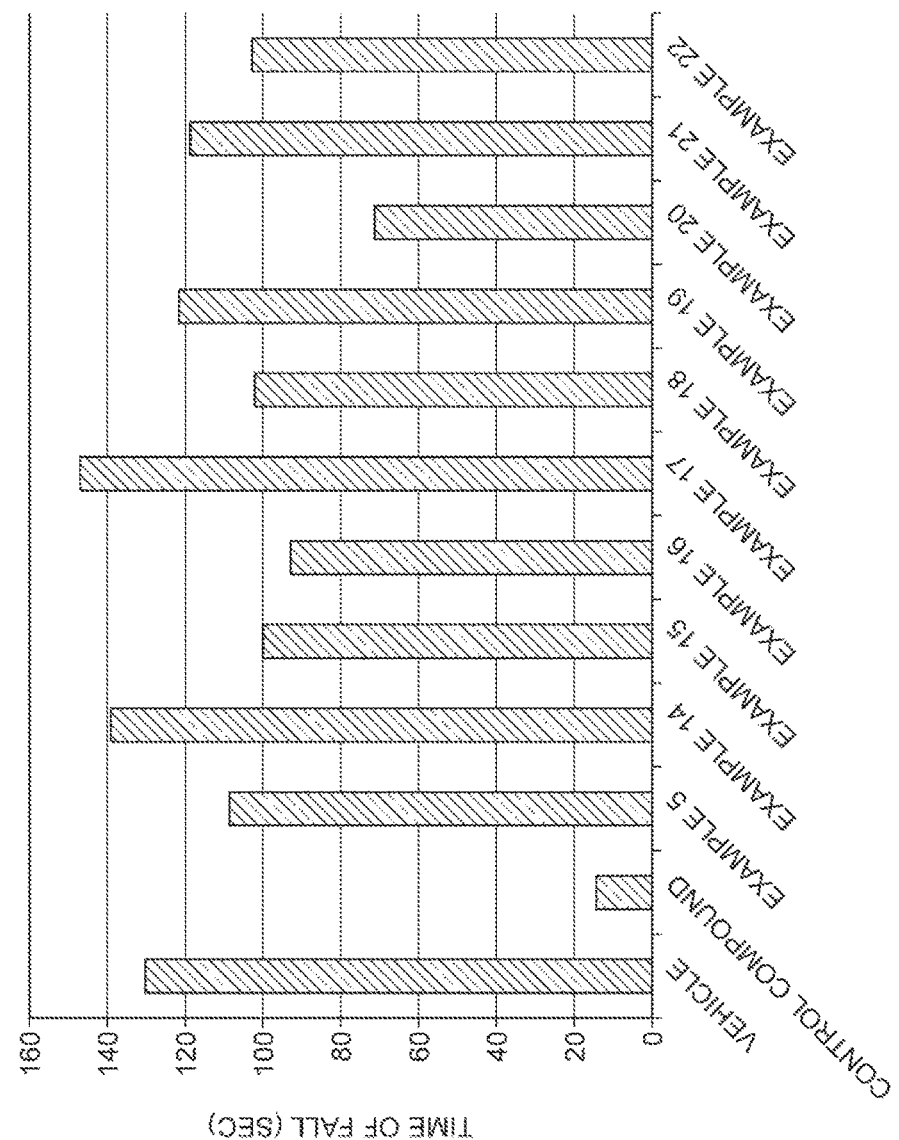
FIG. 2 is a diagram showing the results of rotarod performance tests on compounds of Examples 5 and 14 to 22 and a control compound.

The results are shown in Table 3, Table 4, FIG. 1 and FIG. 2. These results show that the compounds of Examples 1 to 22 at the $ED_{50}$ doses provide lengthened time during which the mice were riding on the rotarod, compared to the control compound, and are believed to further support the applicability of these compounds as AMPA inhibitors with reduced central nervous system depressant action.

TABLE 3

| Treatment | Dose (mg/kg, p.o.) | Rotarod Performance Test Results | |
|---|---|---|---|
| | | Time of Fall (Sec) | Ratio Relative to the Control Compound |
| Vehicle | — | 106.7 | 8.7 |
| Control Compound | 3.96 | 12.2 | 1.0 |
| Example 1 | 2.08 | 56.3 | 4.6 |
| Example 2 | 1.91 | 148.0 | 12.1 |
| Example 3 | 1.21 | 124.7 | 10.2 |
| Example 4 | 2.33 | 73.2 | 6.0 |
| Example 6 | 2.86 | 68.0 | 5.6 |
| Example 7 | 0.97 | 71.7 | 5.9 |
| Example 8 | 4.85 | 65.8 | 5.4 |
| Example 9 | 3.38 | 109.7 | 9.0 |
| Example 10 | 2.08 | 84.2 | 6.9 |
| Example 11 | 1.69 | 114.7 | 9.4 |
| Example 12 | 1.66 | 80.5 | 6.6 |
| Example 13 | 2.25 | 84.8 | 7.0 |
| Referential Example 1 | 1.41 | 110.7 | 9.1 |

TABLE 4

| Treatment | Dose (mg/kg, p.o.) | Rotarod Performance Test Results | |
|---|---|---|---|
| | | Time of Fall (Sec) | Ratio Relative to the Control Compound |
| Vehicle | — | 130.2 | 9.1 |
| Control Compound | 3.96 | 14.3 | 1.0 |
| Example 5 | 3.23 | 108.7 | 7.6 |
| Example 14 | 2.09 | 139.2 | 9.7 |
| Example 15 | 1.41 | 100.0 | 7.0 |
| Example 16 | 1.05 | 92.8 | 6.5 |
| Example 17 | 2.00 | 147.0 | 10.3 |
| Example 18 | 2.00 | 102.2 | 7.1 |
| Example 19 | 2.00 | 121.7 | 8.5 |
| Example 20 | 2.47 | 71.3 | 5.0 |
| Example 21 | 2.50 | 118.7 | 8.3 |
| Example 22 | 3.23 | 102.8 | 7.2 |

What is claimed is:

1. A compound selected from the group consisting of:

9-(2-chlorophenyl)-7-(pyridin-3-yl)-6H-pyrano[3,2-b:5,4-b']dipyridin-8(7H)-one:

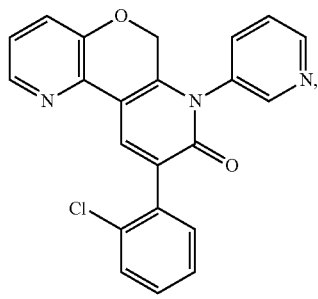

(I)

2-fluoro-6-(7-(5-methoxypyridin-3-yl)-8-oxo-7,8-dihydro-6H-pyrano[3,2-b:5,4-b']dipyridin-9-yl)benzonitrile:

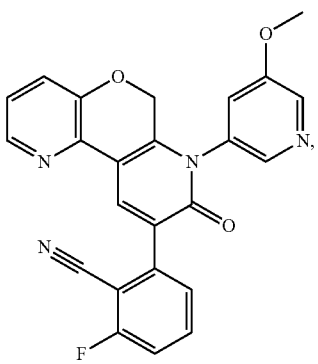

(II)

2-fluoro-6-(7-(6-methylpyridin-3-yl)-8-oxo-7,8-dihydro-6H-pyrano[3,2-b:5,4-b']dipyridin-9-yl)benzonitrile:

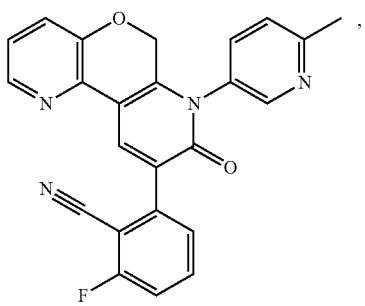

(III)

9-(2-chloro-3-fluorophenyl)-7-(6-methylpyridin-3-yl)-6H-pyrano[3,2-b:5,4-b']dipyridin-8(7H)-one:

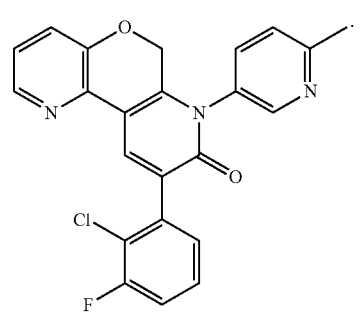

(IV)

2-fluoro-6-(7-(2-methoxypyrimidin-5-yl)-8-oxo-7,8-dihydro-6H-pyrano[3,2-b:5,4-b']dipyridin-9-yl)benzonitrile:

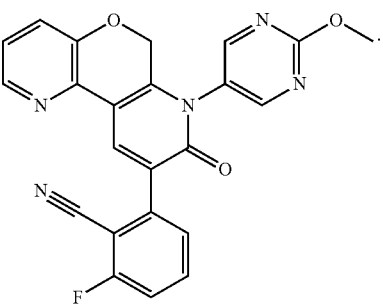

(V)

7-(pyridin-3-yl)-9-(2,3,5,6-tetrafluorophenyl)-6H-pyrano[3,2-b:5,4-b']dipyridin-8(7H)-one:

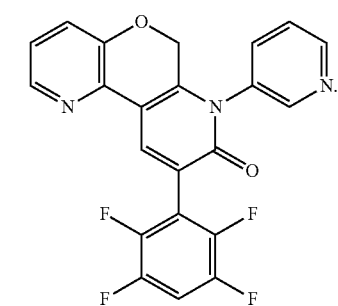

(VI)

3-(8-oxo-7-(thiophen-3-yl)-7,8-dihydro-6H-pyrano[3,2-b:5,4-b']dipyridin-9-yl)picolinonitrile:

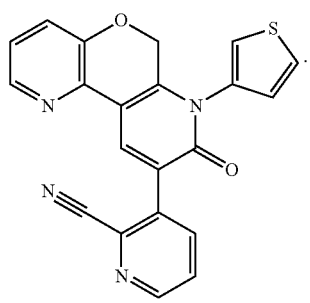

(VII)

3-(8-oxo-7-(thiophen-3-yl)-7,8-dihydro-6H-pyrano[3,2-b:5,4-b']dipyridin-9-yl)pyrazine-2-carbonitrile:

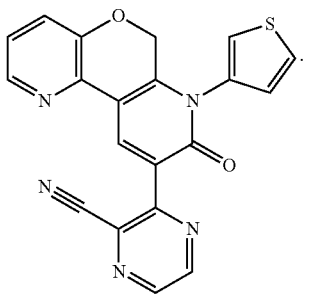

(VIII)

9-(2-fluorophenyl)-7-phenyl-6H-pyrano[3,2-b:5,4-b']dipyridin-8(7H)-one:

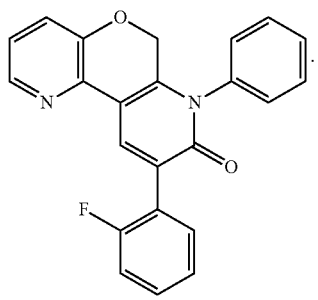

(IX)

2-(7-(4-fluorophenyl)-8-oxo-7,8-dihydro-6H-pyrano[3,2-b:5,4-b']dipyridin-9-yl)benzonitrile:

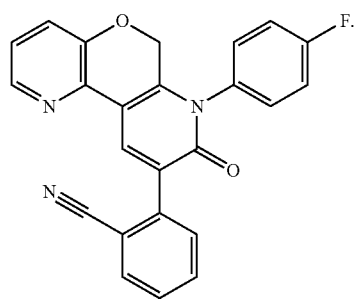

(X)

3-(7-(4-fluorophenyl)-8-oxo-7,8-dihydro-6H-pyrano[3,2-b:5,4-b']dipyridin-9-yl)picolinonitrile:

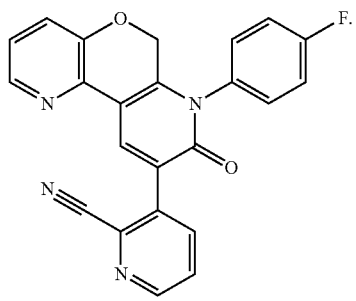

(XI)

3-(7-(2-fluorophenyl)-8-oxo-7,8-dihydro-6H-pyrano[3,2-b:5,4-b']dipyridin-9-yl)picolinonitrile:

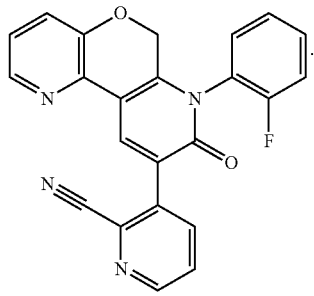

(XII)

3-(3-fluoro-8-oxo-7-phenyl-7,8-dihydro-6H-pyrano[3,2-b:5,4-b']dipyridin-9-yl)picolinonitrile:

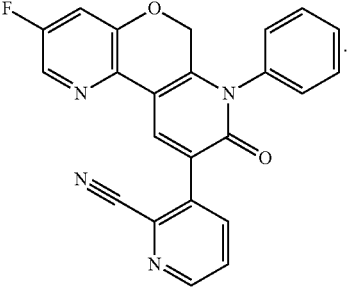

(XIII)

2-fluoro-6-(3-fluoro-8-oxo-7-(pyridin-3-yl)-7,8-dihydro-6H-pyrano[3,2-b:5,4-b']dipyridin-9-yl)benzonitrile:

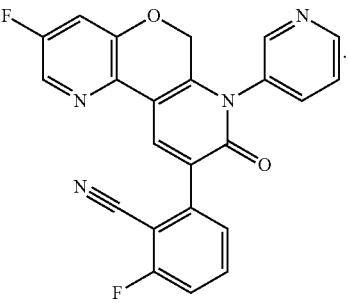

(XIV)

2-fluoro-6-(7-(5-fluoropyridin-3-yl)-8-oxo-7,8-dihydro-6H-pyrano[3,2-b:5,4-b']dipyridin-9-yl)benzonitrile:

(XV)

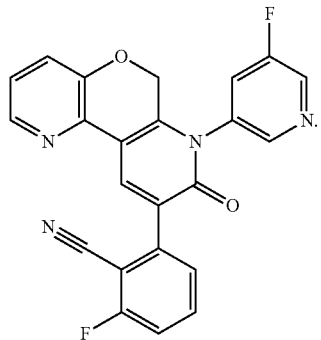

9-(2-chloro-3-fluorophenyl)-7-(5-fluoropyridin-3-yl)-6H-pyrano[3,2-b:5,4-b']dipyridin-8(7H)-one:

(XVII)

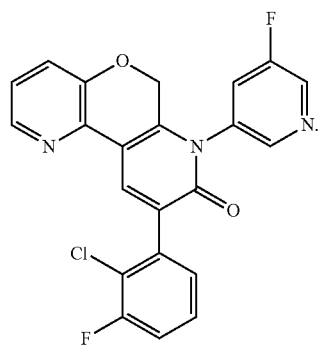

2-fluoro-6-(8-oxo-7-(pyrimidin-5-yl)-7,8-dihydro-6H-pyrano[3,2-b:5,4-b']dipyridin-9-yl)benzonitrile:

(XVIII)

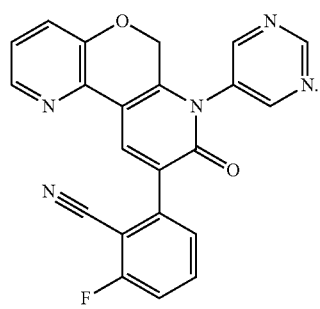

3,6-difluoro-2-(8-oxo-7-(pyridin-3-yl)-7,8-dihydro-6H-pyrano[3,2-b:5,4-b']dipyridin-9-yl)benzonitrile:

(XIX)

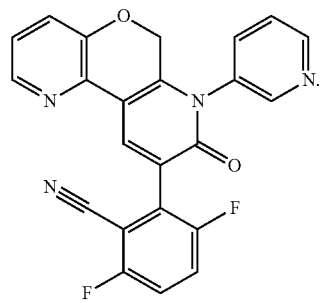

2-(7-(5-chloropyridin-3-yl)-8-oxo-7,8-dihydro-6H-pyrano[3,2-b:5,4-b']dipyridin-9-yl)-6-fluorobenzonitrile:

(XX)

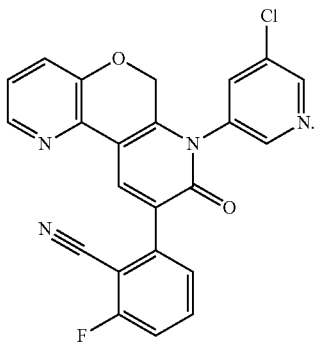

2-fluoro-6-(7-(2-methylpyrimidin-5-yl)-8-oxo-7,8-dihydro-6H-pyrano[3,2-b:5,4-b']dipyridin-9-yl)benzonitrile:

(XXI)

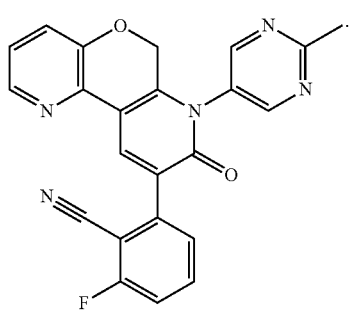

and 9-(3-fluoro-2-methylphenyl)-7-(pyridin-3-yl)-6H-pyrano[3,2-b:5,4-b']dipyridin-8(7H)-one:

(XXII)

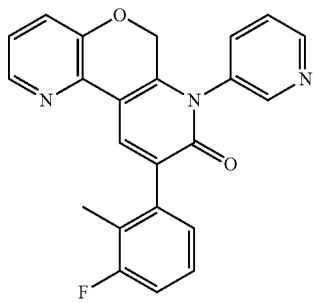

or a pharmaceutically acceptable salt thereof.

2. The compound or the pharmaceutically acceptable salt thereof according to claim 1, wherein the compound is 9-(2-Chlorophenyl)-7-(pyridin-3-yl)-6H-pyrano[3,2-b:5,4-b']dipyridin-8(7H)-one:

(I)

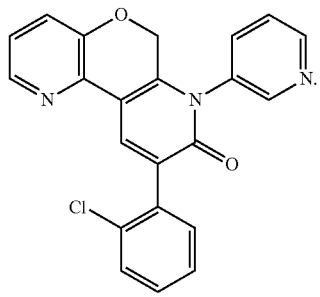

3. The compound or the pharmaceutically acceptable salt thereof according to claim 1, wherein the compound is 2-Fluoro-6-(7-(6-methylpyridin-3-yl)-8-oxo-7,8-dihydro-6H-pyrano[3,2-b:5,4-b'] dipyridin-9-yl)benzonitrile:

(III)

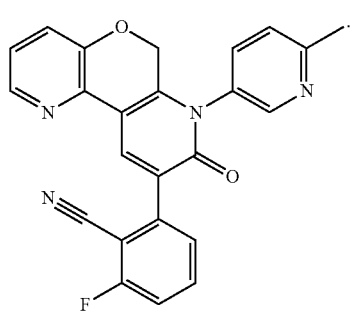

4. The compound or the pharmaceutically acceptable salt thereof according to claim 1, wherein the compound is 9-(2-Chloro-3-fluorophenyl)-7-(6-methylpyridin-3-yl)-6H-pyrano[3,2-b:5,4-b']dipyridin-8(7H)-one:

(IV)

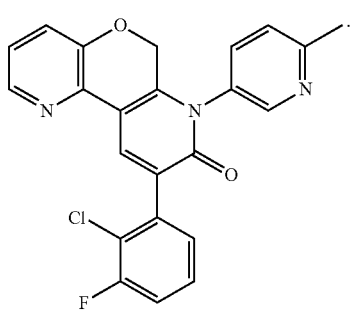

5. The compound or the pharmaceutically acceptable salt thereof according to claim 1, wherein the compound is 2-Fluoro-6-(7-(2-methoxypyrimidin-5-yl)-8-oxo-7,8-dihydro-6H-pyrano[3,2-b:5,4-b']dipyridin-9-yl)benzonitrile:

(V)

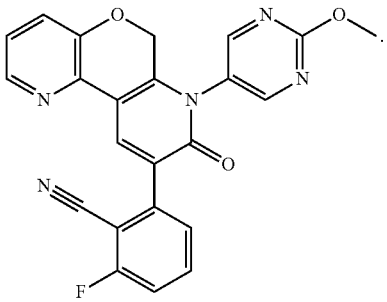

6. The compound or the pharmaceutically acceptable salt thereof according to claim 1, wherein the compound is 3-(7-(4-Fluorophenyl)-8-oxo-7,8-dihydro-6H-pyrano[3,2-b:5,4-b']dipyridin-9-yl)picolinonitrile:

(XI)

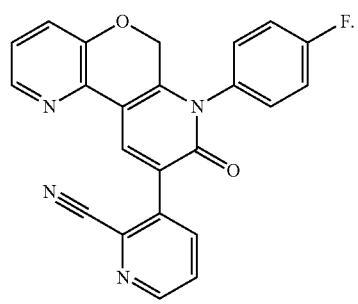

7. The compound or the pharmaceutically acceptable salt thereof according to claim 1, wherein the compound is 3-(3-Fluoro-8-oxo-7-phenyl-7,8-dihydro-6H-pyrano[3,2-b:5,4-b']dipyridin-9-yl)picolinonitrile:

(XIII)

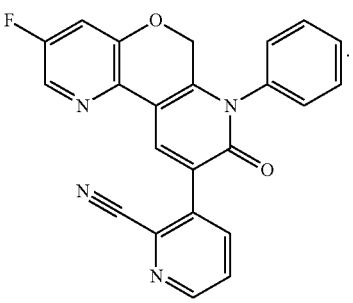

8. The compound or the pharmaceutically acceptable salt thereof according to claim 1, wherein the compound is 2-Fluoro-6-(3-fluoro-8-oxo-7-(pyridin-3-yl)-7,8-dihydro-6H-pyrano[3,2-b:5,4-b']dipyridin-9-yl)benzonitrile:

(XIV)

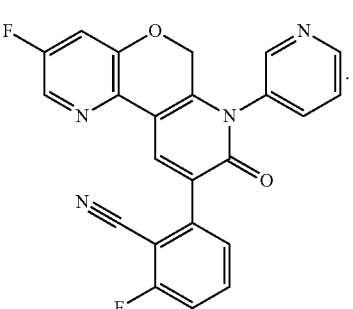

9. The compound or the pharmaceutically acceptable salt thereof according to claim 1, wherein the compound is 2-Fluoro-6-(8-oxo-7-(pyrimidin-5-yl)-7,8-dihydro-6H-pyrano[3,2-b:5,4-b']dipyridin-9-yl)benzonitrile:

(XVIII)

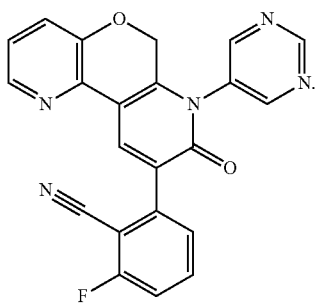

10. The compound or the pharmaceutically acceptable salt thereof according to claim 1, wherein the compound is 3,6-Difluoro-2-(8-oxo-7-(pyridin-3-yl)-7,8-dihydro-6H-pyrano[3,2-b:5,4-b']dipyridin-9-yl)benzonitrile:

(XIX)

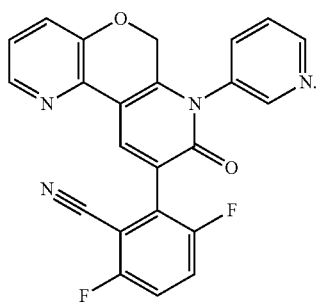

11. The compound or the pharmaceutically acceptable salt thereof according to claim 1, wherein the compound is 2-Fluoro-6-(7-(2-methylpyrimidin-5-yl)-8-oxo-7,8-dihydro-6H-pyrano[3,2-b:5,4-b']dipyridin-9-yl)benzonitrile:

(XXI)

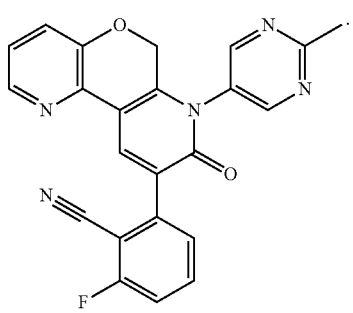

12. A pharmaceutical composition comprising, as an active ingredient, the compound according to claim 1 or a pharmaceutically acceptable salt thereof.

13. A method for treating epilepsy in a patient in need thereof, comprising administering to the patient the compound according to claim 1 or a pharmaceutically acceptable salt thereof.

14. The method for treating epilepsy according to claim 13 wherein epilepsy is partial epilepsy.

* * * * *